United States Patent
Levitt et al.

(10) Patent No.: US 11,911,450 B2
(45) Date of Patent: Feb. 27, 2024

(54) METHOD FOR MANAGING PAIN

(71) Applicant: UNIVERSITY OF MIAMI, Miami, FL (US)

(72) Inventors: Roy Levitt, Miami, FL (US); Gerald Z. Zhuang, Miami, FL (US)

(73) Assignee: UNIVERSITY OF MIAMI, Miami, FL (US)

( * ) Notice: Subject to any disclaimer, the term of this patent is extended or adjusted under 35 U.S.C. 154(b) by 949 days.

(21) Appl. No.: 16/629,477

(22) PCT Filed: Jul. 13, 2018

(86) PCT No.: PCT/US2018/042122
§ 371 (c)(1),
(2) Date: Jan. 8, 2020

(87) PCT Pub. No.: WO2019/014615
PCT Pub. Date: Jan. 17, 2019

(65) Prior Publication Data
US 2021/0128704 A1    May 6, 2021

Related U.S. Application Data

(60) Provisional application No. 62/532,182, filed on Jul. 13, 2017.

(51) Int. Cl.
| | | |
|---|---|---|
| A61K 38/51 | (2006.01) | |
| A61P 25/02 | (2006.01) | |
| A61P 29/00 | (2006.01) | |
| A61K 9/00 | (2006.01) | |
| C12N 9/88 | (2006.01) | |
| C12N 15/86 | (2006.01) | |

(52) U.S. Cl.
CPC ............ *A61K 38/51* (2013.01); *A61K 9/0019* (2013.01); *A61K 9/0085* (2013.01); *A61P 25/02* (2018.01); *A61P 29/00* (2018.01); *C12N 9/88* (2013.01); *C12N 15/86* (2013.01); *C12Y 402/01001* (2013.01); *C12N 2750/14143* (2013.01)

(58) Field of Classification Search
CPC .. C12Y 402/01001; A61K 38/51; C12N 9/88; C12N 15/86
See application file for complete search history.

(56) References Cited

U.S. PATENT DOCUMENTS

| 5,846,707 A | 12/1998 | Roizman | |
|---|---|---|---|
| 2008/0019975 A1* | 1/2008 | Gorman | A61P 37/00 514/13.2 |
| 2009/0324730 A1 | 12/2009 | Fallon | |

FOREIGN PATENT DOCUMENTS

WO    WO-2008010637 A1    1/2008

OTHER PUBLICATIONS

Weber-Adrian et al. Gene delivery to the spinal cord using MRI-guided focused ultrasound. Gene Therapy 2015, 22:568-577. (Year: 2015).*
Agilent Technologies. AAV Helper-Free System instruction manual. 2015, 1-48. (Year: 2015).*
Akkiraju et al., Role of Chondrocytes in Cartilage Formation, Progression of Osteoarthritis and Cartilage Regeneration, J. Dev. Biol., 3(4):177-192 (2015).
American Pain Society, NIH study shows prevalence of chronic or severe pain in U.S. adults, available online at <https://www.newswise.com/articles/nih-study-shows-prevalence-of-chronic-or-severe-pain-in-u-s-adults>, Aug. 19, 2015, 1 page.
Birnbaum et al., Societal costs of prescription opioid abuse, dependence, and misuse in the United States, Pain medicine, 12:657-67 (2011).
Boyce-Rustay et al., Animal models of acute and chronic inflammatory and nociceptive pain, Methods Mol. Biol., 617:41-55 (2010).
Chaplan et al., Quantitative assessment of tactile allodynia in the rat paw, J. Neurosci. Methods, 53(1):55-63 (1994).
Fehrenbacher et al., Models of inflammation: Carrageenan-or complete Freund's Adjuvant (CFA)-induced edema and hypersensitivity in the rat, Curr. Protoc. Pharmacol., Chapter 5, Unit 54 (2012).
Hargreaves et al., A new and sensitive method for measuring thermal nociception in cutaneous hyperalgesia, Pain, 32(1):77-88 (1988).
Hogan et al., Painful neuropathy decreases membrane calcium current in mammalian primary afferent neurons, Pain, 86(1-2):43-53 (2000).
Ikeuchi et al., A novel long and unstable CAG/CTG trinucleotide repeat on chromosome 17q, Genomics, 49(2):321-326 (1998).
International Application No. PCT/US18/42122, International Preliminary Report on Patentability, dated Jan. 23, 2020, 7 pages.
International Application No. PCT/US18/42122, International Search Report and Written Opinion, dated Sep. 13, 2018.
Kawano et al., Nitric oxide activates ATP-sensitive potassium channels in mammalian sensory neurons: action by direct S-nitrosylation, Mol. Pain, 5:12 (2009).

(Continued)

*Primary Examiner* — Allison M Fox
*Assistant Examiner* — Jennifer S Spence
(74) *Attorney, Agent, or Firm* — MARSHALL, GERSTEIN & BORUN LLP

(57) ABSTRACT

The invention provides a method of treating or preventing pain in a subject in need thereof. The method comprising administering to the subject an expression vector comprising a nucleic acid sequence encoding carbonic anhydrase (10) or carbonic anhydrase (11) such that the nucleic acid is expressed to produce carbonic anhydrase (10) or carbonic anhydrase (11). Alternatively, the method comprising administering to the subject an expression vector comprising a nucleic acid sequence encoding a carbonic anhydrase (8) fragment such that the nucleic acid is expressed to produce the carbonic anhydrase (8) fragment.

23 Claims, 45 Drawing Sheets

Specification includes a Sequence Listing.

(56) References Cited

OTHER PUBLICATIONS

Kim et al., An experimental model for peripheral neuropathy produced by segmental spinal nerve ligation in the rat, Pain, 50(3):355-363 (1992).
Moon et al., A genome-wide association study of copy-number variation identifies putative loci associated with osteoarthritis in Koreans, BMC Musculoskelet Disord., 16:76 (2015).
Mori et al., Nucleotide Variations in Genes Encoding Carbonic Anhydrase 8 and 10 Associated with Femoral Bone Mineral Density in Japanese Female with Osteoporosis, J. Bone Miner. Metab., 27(2):213-216 (2009).
Sarantopoulos et al., Beta-escin diminishes voltage-gated calcium current rundown in perforated patch-clamp recordings from rat primary afferent neurons, J. Neurosci. Methods, 139(1):61-8 (2004).
Sarantopoulos et al., Gabapentin decreases membrane calcium currents in injured as well as in control mammalian primary afferent neurons, Reg. Anesth. Pain Med., 27(1):47-57 (2002).
Sarantopoulos et al., Opposing effects of spinal nerve ligation on calcium-activated potassium currents in axotomized and adjacent mammalian primary afferent neurons, Brain Res., 1132(1):84-99 (2007).
Taniuchi et al., Developmental Expression of Carbonic Anhydrase-Related Proteins VIII, X, and XI in the Human Brain, Neuroscience, 112(1):93-99 (2002).
Vincent et al., Unstable repeat expansion in major psychiatric disorders: two decades on, is dynamic DNA back on the menu?, Psychiatr. Genet., 26(4):156-165 (2016).
Zhuang et al., Carbonic Anhydrase-8 Regulates Inflammatory Pain by Inhibiting the ITPR1-Cytosolic Free Calcium Pathway, PLoS One, 10(3):1-24 (2015).
Gerald Z. Zhuang et al: "Carbonic Anhydrase-8 Regulates Inflammatory Pain by Inhibiting the ITPR1-Cytosolic Free Calcium Pathway", PLOS ONE, vol. 10, No. 3, Mar. 3, 2015 (Mar. 3, 2015), p. e0118273, XP055574892, DOI: 10.1371/journal.pone.0118273.
Roy C Levitt et al: "Carbonic anhydrase-8 gene therapy inhibits the ITPR1-cytosolic free calcium pathway producing analgesia and anti-hyperalgesia", Molecular Pain, Biomed Central, London, GB, vol. 10, No. Suppl 1, Dec. 15, 2014 (Dec. 15, 2014), p. 07, XP021205142, ISSN: 1744-8069, DOI:10.1186/1744-8069-10-S1-07.
Levitt Roy C et al: "Car8dorsal root ganglion expression and genetic regulation of analgesic responses are associated with a cis-eQTL in mice", Mammalian Genome, Springer New York LLC, US, vol. 28, No. 9, May 25, 2017 (May 25, 2017), pp. 407-415, XP036330482, ISSN: 0938-8990, DOI:10.1007/S00335-017-9694-7 [retrieved on May 25, 2017].
Upadhyay U. et al.: "Effects of carbonic anhydrase VIII and its alternative transcripts on nociception and cytoplasmic Ca2+ release based on the genetic association", The Journal of Pain, vol. 18, No. 4, 101, Apr. 1, 2017 (Apr. 1, 2017), p. S2, XP055785768, Retrieved from the Internet: URL:https://www.jpain.org/article/S1526-5900(17)30040-8/pdf [retrieved on Mar. 15, 2021].

\* cited by examiner

```
         10          20          30          40          50
MEIVWEVLFL  LQANFIVCIS  AQQNSPKIHE  GWWAYKEVVQ  GSFVPVPSFW
         60          70          80          90         100
GLVNSAWNLC  SVGKRQSPVN  IETSHMIFDP  FLTPLRINTG  GRKVSGTMYN
        110         120         130         140         150
TGRHVSLRLD  KEHLVNISGG  PMTYSHRLEE  IRLHFGSEDS  QGSEHLLNGQ
        160         170         180         190         200
AFSGEVQLIH  YNHELYTNVT  EAAKSPNGLV  VVSIFIKVSD  SSNPFLNRML
        210         220         230         240         250
NRDTITRITY  KNDAYLLQGL  NIEELYPETS  SFITYDGSMT  IPPCYETASW
        260         270         280         290         300
IIMNKPVYIT  RMQMHSLRLL  SQNQPSQIFL  SMSDNFRPVQ  PLNNRCIRTN
        310         320
INFSLQGKDC  PNNRAQKLQY  RVNEWLLK
```

FIG. 8

```
  1 ATGGAAATAGTCTGGGAGGTGCTTTTTCTTCTTCAAGCCAATTTCATCGTCTGCATATCA  60
  1 ATGGAAATAGTCTGGGAGGTGCTTTTTCTTCTTCAAGCCAATTTCATCGTCTGCATATCA  60

61 GCTCAACAGAATTCACCAAAAATCCATGAAGGCTGGTGGGCATACAAGGAGGTGGTCCAG 120
 61 GCTCAACAGAATTCACCAAAAATCCATGAAGGCTGGTGGGCATACAAGGAGGTGGTCCAG 120

121 GGAAGCTTTGTTCCAGTTCCTTCTTTCTGGGGATTGGTGAACTCAGCTTGGAATCTTTGC 180
121 GGAAGCTTTGTTCCAGTTCCTTCTTTCTGGGGATTGGTGAACTCAGCTTGGAATCTTTGC 180

181 TCTGTGGGAAACGGCAGTCGCCAGTCAACATAGAGACCAGTCACATGATCTTCGACCCC 240
181 TCTGTGGGAAACGGCAGTCGCCAGTCAACATAGAGACCAGTCACATGATCTTCGACCCC 240

241 TTTCTGACACCTCTTCGCATCAACACGGGGGGCAGGAAGGTCAGTGGGACCATGTACAAC 300
241 TTTCTGACACCTCTTCGCATCAACACGGGGGGCAGGAAGGTCAGTGGGACCATGTACAAC 300

301 ACTGGAAGACACGTATCCCTTCGCCTGGACAAGGAGCACTTGGTCAACATATCTGGAGGG 360
301 ACTGGAAGACACGTATCCCTTCGCCTGGACAAGGAGCACTTGGTCAACATATCTGGAGGG 360

361 CCCATGACATACAGCCACCGGCTGGAGGAGATCCGACTACACTTTGGGAGTGAGGACAGC 420
361 CCCATGACATACAGCCACCGGCTGGAGGAGATCCGACTACACTTTGGGAGTGAGGACAGC 420

421 CAAGGGTCGGAGCACCTCCTCAATGGACAGGCCTTCTCTGGGGAGGTGCAGCTCATCCAC 480
421 CAAGGGTCGGAGCACCTCCTCAATGGACAGGCCTTCTCTGGGGAGGTGCAGCTCATCCAC 480

481 TATAACCATGAGCTATATACGAATGTCACAGAAGCTGCAAAGAGTCCAAATGGATTGGTG 540
481 TATAACCATGAGCTATATACGAATGTCACAGAAGCTGCAAAGAGTCCAAATGGATTGGTG 540

541 GTAGTTTCTATATTTATAAAAGTTTCTGATTCATCAAACCCATTTCTTAATCGAATGCTC 600
541 GTAGTTTCTATATTTATAAAAGTTTCTGATTCATCAAACCCATTTCTTAATCGAATGCTC 600

601 AACAGAGATACTATCACAAGAATAACATATAAAAATGATGCATATTTACTACAGGGGCTT 660
601 AACAGAGATACTATCACAAGAATAACATATAAAAATGATGCATATTTACTACAGGGGCTT 660

661 AATATAGAGGAACTATATCCAGAGACCTCTAGTTTCATCACTTACGATGGGTCGATGACT 720
661 AATATAGAGGAACTATATCCAGAGACCTCTAGTTTCATCACTTACGATGGGTCGATGACT 720

721 ATCCCACCCTGCTATGAGACAGCAAGTTGGATCATAATGAACAAACCTGTCTATATAACC 780
721 ATCCCACCCTGCTATGAGACAGCAAGTTGGATCATAATGAACAAACCTGTCTATATAACC 780

781 AGGATGCAGATGCATTCCTTGCGCCTGCTCAGCCAGAACCAGCCATCTCAGATCTTTCTG 840
781 AGGATGCAGATGCATTCCTTGCGCCTGCTCAGCCAGAACCAGCCATCTCAGATCTTTCTG 840

841 AGCATGAGTGACAACTTCAGGCCTGTCCAGCCACTCAACAACCGCTGCATCCGCACCAAT 900
841 AGCATGAGTGACAACTTCAGGCCTGTCCAGCCACTCAACAACCGCTGCATCCGCACCAAT 900

901 ATCAACTTCAGTTTACAGGGGAAGGACTGTCCAAACAACCGAGCCCAGAAGCTTCAGTAT 960
901 ATCAACTTCAGTTTACAGGGGAAGGACTGTCCAAACAACCGAGCCCAGAAGCTTCAGTAT 960

961 AGAGTAAATGAATGGCTCCTCAAGTAG                                  987
961 AGAGTAAATGAATGGCTCCTCAAGTAG                                  987
```

FIG. 9

```
AACGCACGCCTGCTTGCACTCACACTGCGGTTCACACCCGGAGGCGCTCTCGCACTCACA
CTGCCGCTCACGCGTGCTCACACTCCCCCACGCGCGCTCCGCTCCGGCTCCAGCCCCGCG
CCCAGCGAAGGCGCAGGCACTGCTGCCGAGAGCGCCGAGGGGCCCCGCGGCCTTCCCATG
GCGGACCTGAGCTTCATCGAAGATACCGTCGCCTTCCCCGAGAAGGAAGAGGATGAGGAG
GAAGAAGAGGAGGGTGTGGAGTGGGGCTACGAGGAAG

GTGTTGAGTGGGGTCTGGTGTTTCCTGATGCTAATGGGGAATACCAGTCTCCTATTAACC
TAAACTCAAGAGAGGCTAGGTATGACCCTCGCTGTTGGATGTCCGCCTCTCCCCAAATT
ATGTGGTGTGCCGAGACTGTGAAGTCACCAATGATGGACATACCATTCAGGTTATCCTGA
AGTCAAAATCAG

TTCTTTCGGGAGGACCATTGCCTCAAGGGCATGAATTTGAACTGTACGAAGTGAGATTTC
ACTGGGGAAGAGAAAACCAGCGTGGTTCTGAGCACACGGTTAATTTCAAAGCTTTTCCCA
TGGAGGTAAGAATAACAAATCATCTTGTAAAAATCTTGTTTTCTGAATAAAGTATTCAGC
GATTTACTGAAAATGATTTAGTTTAAAAGTAGATGCATAGCTCTTGAATTTATCAGTTT
ATACTAAAATTTAAAAAATGCTTAATGCAATGGAAGCCTAGGGCAGCACATGAAACCTCC
TGTCTACTCTCGTGGCTTGGCGTGTGCGCATGAGCACATGGCCAGAAAGGCAATCTACAG
TATTAAATTCACCCTAGTGTTACTATTCTTGTAAAAATTCTGCCTCTGCAAATTCAGTA
GGTCATTTTGTGGATGCTTTGGATAGGTGACGAGCTGAAGACAAGCAACCGTTGGAGAA
ACCTCAACAGTAATGAAAAGTGTAGGTTTGCTAGTTTAAAATTGGTGGGTTGGTTTTATT
CACCCCAAGCCACTTGGGGAGGGAGGGAGAAAGAGAGATTTTTGAGAGTGATTCTTTTG
TCCAAAGAATTCCCTCCCCGACTTACGTTCTTAGTTAACTTCTGCTGTTTCTTGATACG
CAGTTGAAATCTTATGTCTTCTGTGGACTTTTCTCTAGTTTTTCCCTAGGCAGAATTC
ATCTCTCTCTCTGCTCCCTGTATGCTTGATAGGGCACTGCCATGGCGCTGGCCCCATG
GGTTGTACCATTAGTCTCCACAGCGTCTTTCTTGCTGCCTGTGAGCTCCTGAGGACCGA
AGCTCCCTCTCACCCCCTTTTTACTCCATCATTTGCCCACTGCCAGGCACAGTGGAGAT
AGACAGTTCACACTGGTGAAAGTGAGGGGATGTTGGATTCAGTCCACGTCTTGATGTTAT
TTCTAGAAGGAACCTCAGTTACCCCAGAAAATAGCCCTTTGGTGTCATGTAAGAGTATG
TTCTGGGGCTGCTGGTCTTCCAGTCTTTTTTTTGACATTCACAACTGTGCATGTGCTT
AATATTAAATATAAAATTGCTCATGACCAGATGCAATATCCAGTACCACTTCAGTGGCTG
GAAATCATGGCTGTATAATTCTATGTCAGTGATACATGTATTTAGAGTATTCTGTTGAA
GTGTTTGACAGCATTACTGTAATTATAA
```

FIG. 10

\>HPRM36619
NM_001161772;name=HTR3A;Entrez_ID=3359;Genome=hg38;chr11+:113976187-113977531;TSS=113977500;Upstream=1313,Downstream=31;Length=1345;

TCCCGGGAGCGGTCGTTTGGGAGTGCTCCGTGGGTTAAGCAAACGCAAGCTGTAAGTGA
TGACTGTGGTCGAGGGCTTCCTTGACTGAGAAGAAACTCTGTCCCTCCTAGCAATGGTCCT
TTGCCCCGGGCCTGCTGGGATGAGTTCAGTGCTCTCCAAGCTGGTCAGGATCCCAGTCAAT
AGGACCCAGGCTCTTGCTGGTGTAGTAAAGACGCACACGGGTCTGCGTTTGAATCTCAGT
TCCTCCACTTGCAGAGCAAGGTGCTCACCTTTCTGGTGCTTGGGGATCCTTGTGTGCAAAT
AGCCACTCTGGTGGACTGTTCTAAAGTTAAATGAAGAATATGTTTATTGATGTTATTC
CAAAGGAGACACTTAAAAAATAGTTTGTGTGTGTGTGTGTGTGTGTGTGTGTGTGTGT
GTGTGTTCTCTCTGCTCTTCTCTGTCCTTCTGAGGGAAGCCAGTAGCTTATCAGGGAA
AAGGGGGTGAAAGGAGGGGGAATCTGCAGGAGTGATTTGTTGTACAGGTTGCACACTAG
ATGAGAGAAGACACAGTCTTGTTTAGCAAAAGCCAGGCCTTGCCAGCACCTGGTTAGTGA
AAGACCCTGGCTACCTGCCAGCTCCATCTCCCCTTTGCTGCCCGTATGCTGGCCCTCTAGGT
TGTACTCCCTTCACCGTCCCATGAATTTTCACTTTTGCATGTCAGGCCACCCTTCTGGA
AGTGCTCCTGCTGCTTCCAGTGTGAAAACTGAGCTGTGCATGAAATCTTCATAGAACAGC
ACCAGGGTCCAGGAGCTGGGCTGTCTCATTACTGGTTTGTCCCCATAGGCCACCTACCCC
GGAAGTCGTTTGATTTCTTCTCACTCCCTCCACACCTCGCCCCAACCACCTATCTAAGCC
CATCATGTTTGCCCATACAGCAACCCTAGGAGGTGGACTGGGCCAGCCCTCCACCCATAG
CTTGTGTGTGCCTGGGGCAGGGTGCGAGGATCCTCTTGGGGTGGCTTTTGCAGGATGTAG
AGGAAATGTCAGTTTTCACCAGATGCCCACACTTCCTTCTTTCTTTACCTGTTTCATACT
CAAAAAGGAGATGTTGTGTGCAGATGCTGAGGTTTGACCTTGGCTGAGGAAAACCCTGAT
GCAGACCCTTGGGCTTAGAAATTGTGCACTTGGGGTCATGCTTTCTTGCAACCCTCTTGC
TTTTAGTATCATACCCTGAGAGCCAGCTTCCTTGTTGCTCCCCAGAGGCCCTCGCTTAGG
CCCCGTGGGCCACCTGCTCCGACCTTCTTAGCCCTCAACCTGATTTGAATCTCAGCTGTC
TTGTGCCACTTGCTCTTCCAAGCCA

```
TTTTGATTTTAATTAGAAGAAAGACTGCCATTAGAATTGTTTTCTAATGA   -1037
AATCTTTATAAATTCTCTGGGCAGTGCCTGTATCTTTATTAGAAAGACTT   -987
                                        Oct-1
CTTATTTTTAACAATTTTATTTGGAAGAAGTTCTACTC[ATTTGCAT]CAGT  -937
TCATCGTCTACATAATTGTGTGTGTGTGTGTGTATGTGTGTGTTACAAC    -887
          AP-1
TTTGACTTT[TGAACTA]GAATAGAATCAGGTAAAACATCTAAGATCAGTG   -837
TGCCAGTAATTGGCCTGAATCATCGGGCACCATGATGGGTTTGGCCGCCT   -787
TCAACGGTACTCGTGTACATTCTATTTTTTCTTCATAATGTTCAGTACT    -737
GTAGTACTAATCACCGAGAAAATTGCATTGACTCTTTTCGACCACCAGGG   -687
AAATATTCAGCTCATGGTTCTCCCCAAAAAAACTAAAAAGCAGCTAAGCG   -637
CTGGAACAAATCTGACTTATTGCATTTTCTCAGTGGGCCAAAGAAAGGA    -587
GGGCCGATTGACTGCTTTGACTTTTTAAAGGTCTTCTCTTTGTTCACTTA   -537
TAAAGTGAGGAAAACAAATTCTCCGCACTGGCGTGAGAGTTGAGCGTCAC   -487
AAAAGAAAGCAAAAGAAAATATTAGTGCCATTATTGTGGCGAATTTCATG   -437
TTTCCCAGCGAGCCCTTTGATTCCTGGTTTGGGCTGGCGCTCGAGCTCTC   -387
CAGCCGGGTATGACTTCGGCCACAAGATGGCACTGACCTGCAAACAAAGA   -337
AAAGCACAGTGGCACCGACTTTTTCAAGCCTCGGGAAACTGCCCTGCCTT   -287
CCCCGGAGTCGAGGACTGTGGGGATTAGGCTTCCTTTCCCCTGCCGCGGG   -237
AGGTCTGTGTCGAATAATGTGTGGCTTCTGTTGGATTGCTTTTCTTTCCA   -187
AAATTCCTAGGCAATGCTTCCCCGAGGTGTGCACCTTTGTGAGGTGTTTG   -137
                                         CRE
TGGGGTTGGGGGAGCTTCAGGCGCTACTCGCGGGA[TGACGTCA]CGTGATC  -87
CGGGATGAGGTGGAGTTCGGCTTTAAGGAGGCGTCTCTTCCTAGCTTCAT   -37
CAATCTTTAGGATCTGAGCAGGAGAAATACCAGCGGATGTTGCCGACTGT   +14
GCTCCCTTCCATTCCCAGCCTTCCTTCTTTAATAAGCAGGAGCGAAAAAG   +64
ACAAATTCCAAAGAGGGTAAGTTGCGAGTTTATGCCTTTCCAGAGACTTC
TGCGAAATCTCT
```

```
GAGCAAAAGTGTGAAAATAAAGTCTTTATTAAACTATGGCAACTTATAAA    -950
                                 NFKB
AAATAATATCTTTTTAAAGGTTTACTGGAATTTCTATAAACTCTTCT       -900
ATATCTGACACCTAGACAAATGAAACCTTCTGAATAGATTTTAAGTATTT    -850
TAAGAAAGTAGATAGTTCTCAAGAATAATAGGAGGAACTGCAGGGAATTC    -800
AAAGGATATTAAAGTCTGACTTGTACATTTAAATAAGGTTTCTTTGTT      -750
AP-1
GAATAATTTTTGCTTTATGAAAATACACATCATTCTTTTCACAAAGGAT     -700
GACAATCACACAAAAGAATAAAATATATGTAATTCTTTTTCCTCCTGCAA    -650
TGATACAATATCAACTATTGTCTGTTTTGCTGTGATCGTGGAACAGCAGC    -600
              GR
ATGATTCCATGTTCTCAAATATTCCCATGGTTTTTTCTTAAAGCCAGAAT    -550
CTGGCACAATTTGAATTGGAAAGATAAATACAGCTCTGCTCAGCTGACAA    -500
ACACACAGGCATGCACCACCCTCCCTTCCAAATTCTAACAGCAGAGTTTC    -450
TCTTCCCTTGAGAAATCTGAAATCTAAAAATTGCATTCGGACTGCCAAAA    -400
ATTCTGCTGAAAGAGCCTTAGGCTATTTTCCATGGTGTAAGGTAAAATC     -350
GTTTTGGCTTTGGTCCAACACAACGCCTCAGTTCCTTTAAAAGATTAACT    -300
AAAGTCTGTGAACTTGGAAAAAGAATTCCTTGGAATTCGAGTTCTATG      -250
GATGTTTGTTATTGCTCGCATTTGTTATATGAAGACACCTCGCAAACAGG    -200
AGCGCAAACCTTAGAGCGCAGCTGCCTCCCGGGCTCGGGTCAGCGCTGGA    -150
                                        AP-2
CCGCGGCGGCAGCTGGACGGCCTGAGTGGCGCCCCGCGGGCGCCCCG       -100
                                               AP-2
GCCTCGCCAGAGACCCGCTAGGTTGAGCCCTGACCCGGGCACCCCGCGGG    -50
GCTGTTCCCAGCTCCGGATGCCAGCCGGGCTAGCGCCAGAGCGTGTCC      +1
AGCCGGGGGCAGCGCTTTGTCCATCCCCCGCCCCATCCCCAGGAGGCTCC    +51
TTCGCGGATCCCCGACACTCTCCTTCCGGGTTCGGCCCGCGCCTGCTCCA    +101
CCCCGTGAGTTGGGAACCGGAGGGACCTGCTCGGCACGAAAGAATTC
```

```
AAATATTCTTTAAAATTATTTAATAATGGAAATACAGATACCATTTAGAC    -1077
TTCACATTTTAGAATAGTTTTGATGTATATGAAAACAACTTTTATTGGTA    -1027
GTGTTTAATGTTGTATAATGAGTCTGGAAAGGATTTAAAATTCTTTATTT    -977
GGTAAATTACTTGTGTATTACTAGGACAGTGGAGTTAAATTGACAATTTG    -927
ACCAATTCTCAATAGGCAATAGCATTTTCCTACAGGACTTCCAAAACTGT    -877
AGTTAATGTTGAAGATTATAATCATAATTTGGGCATACATCTGTCATTTA    -827
GTTGTGATTTTCCAGGCATATTAAATTTTTTCTGTACTTCACAAACTAAA    -777
CATTAAGAAGCCTATGGAGTAGAAATGATATAGATAGCTGGTAGATATTC    -727
TTCAAGTTTGAAATTAAAGTTCCTCGAGAAAATTTTTTCTTATTATAT     -677
TTTGGACAAAAGTACTGAGTTGGTTAGATATAACTTTTACTTTCAACAA    -627
AAAATACAATTCATTTGTTTATAAGACAACATGGAAGTGGAAGGTAATAC    -577
AACCTTCTAAAGTGAAATTACAGATTGGATTGACACTGACTGCACAACTA    -527
AATAAATTAATCCTACTATAACACATAAAATTATCTTCCATATATTATGA    -477
ACTGACATTTGAATCCAGAACTCTTTCACATAAATTAAATTCCATGTTAA    -427
CAAAATTTCTATTTATTATATGTAAATAGTTATCATAAATATATTTTATA    -377
                     GR
TGACCCCAGCATTNNNNNNTTCCTTGGTAAACAGTGAGAATTATTACATA    -327
TGAAGACAGTGTATAAGGGACACTAAATCAGCTTTAATCCCATTATTAAG    -277
AAACCCATATAGAATTGGATTAAGACAACAGGACATCATGCCCACAATGA    -227
CAATGCAATACACCAACTTGAAATGCCTATTTGAAATAAGATTGTCATTA    -177
AAATCAGTTACCACATGGAAAAGGTGTAGTGGCATCCAACTAACAGCAAA    -127
TACTAATATCAGTATGGTCAGTCTGTAGAAAACACTTCGAGATCTCTTTT    -77
TTATTCTTGTAACAGAACGTTTTACTCTCAATTCATGAACATCTGAATTT    -27
            *   *  *
TCTTCAGGTTTTATCTCAAAGCAAGTGGGACCCCTGGTATGAACTTACT    +24
GGATGAAGAGAGCTGACTTCTTACAGAGCCAAAGTTTTCTGGAAGTATTC    +74
TGGAGTGGTTCTCTTGAGAAGGTGTTTCTGGAGCAGTAACACACATGCT
GTCTTCTTGCTATATCTTCTTCTGTGTTTTTTGATGAATGAATAACTCCA
TTTATGGC
```

FIG. 24

```
mouse  CGGAGAACATTTTTGTTTCAGCATTTCAT.CTGAAGCCACGGTTTCACATCATCAAGTC
rat    TTGAGAACATTTTTGTCTCAGCATTTCAT.CTGAAGCTATGGTTTTACATCACCAAGTC
human  TTTTTTTTTTTTTTGTAATTTCATTTCAAA......CTATTATTTTATAAGACCTGGCC
                                        -0.6kb                   Primer A
mouse  T...........GCAAAAAACCGTTCACAAACCACACCAAAACTTCTC.GGTAAAGAAC
rat    T...........GCAAAAAACAGTTCGCAAACGGAACCAAAACTTTTTCGACAAAGAAC
human  TATTACTGAGTATGCAGGCAGAATATGAAAATTACTCCAAAACTTTTTT..AAATGAAA
                        TCF1                                    TCF1
mouse  TCCT.AAGGCC..AAAGAGGGAGACTGGGTAGATTGTTTTTAATTTGTTTCTTTTTGTC
rat    TTTT.AAGGCG..AAAACGGGAGATAGAGTAGATTGTTTTTAATTTGTTTCTTTCTGGC
human  TTTCAAGATGCAAAAA................GTGAAACTTTAAAATTTCAGTGGA
         TCF1             TCF1    Primer B
mouse  AAAGGGGGACAAAACACGCTTTGCTGAGTGCGAGTGTTTATTCTGGGACACAAACCCAG
rat    AAAGGGGGACAAAACACACTTTGACGAGTGTGAGTGTTTATTCTGGGAC..AAACCCAG
human  AGAAGGGGAACAAAAACATTTTAATAAATGAGAGTGTTTATTCCAGAATGGGAATATAG
                                             AP2           AP2
mouse  AGT.CTGGAAGGGAGCAT.TCAACGGGTGCTGCTCTGCCACGCAGGGGCAGCGGTGGGA
rat    AGT.ATGAAAGGGAGCAT.TCGGTGGGTGCCGCTCTGCCATGCAGGGGC.GCGGTGGGG
human  AGACAAGGAAGGTACCATGTGAATGGGTGCACCTCG.CTCTCTGGGGTCAATGATAGGA
         SP1                  AP2                 AP2  -0.3kb  Primer C
mouse  CTCAGCCCATCCTGCTAAGGACGGGCAGCCTGAGCC.AGGCTTGGGACTCTGTCATGGC
rat    CTCAGCCCATCCTGCTCAGGAC..CCAGCCTGGCCCCAGGCTTGGGAGTCTGTCATGGC
human  AACAGCCTGTCCCA..CAGTCAAGGCAGCCTTGCCC.AGGCTAT.GAGTCTATTGTGGA
                 GATA1             TCF1
mouse  TGCCAGACGAATCATTATCTAATTGCAGCCTTTTCTCTTCCTTAGGTTTCAGCAGGTCC
rat    TGCCAGAGGAATCATTATCTAATTGCAGCCTTTTCTCTTCCTTAGGTTTCAGCGCGTCC
human  TGCTGGGGCATT.GTTATCTAAGTGCAGCCTCTTTGCTTCCTCAGGTTTCAGCATTTCC
              Brn2    GFI1                        Primer D
mouse  CGAGAGAGCATTTAAAATCACATTTACTACTTTACCATCTAATCACACATAAGCCTCTC
rat    CAGGAGAGCATTTAAAATCACATTTACTACTTTACCATCTAATCACACATAAGCCTCTC
human  CATGAGATCATTTAAAATCACATTTGCTATTTTACCATCTAATCACACATAAGCCTCTC
                             -0.2kb
mouse  CCTATA..CCCTCCACCCTCCTTCCATTCAG..AGTGTACTTTCTGGAGCACCATCCAG
rat    CCCATA..CCCTCCACCCTCCTTCCATTCAG..AGTGTACTTTCTGGAGCGCCATCCAG
human  CCCACACTCCCCCGCCCTGTTTCCATCCAAGGAGTGCACTTTCTGGAGCACCAGCAAC
         -122    -0.1kb CREB/AP1/ATF/TCF1  Primer E             -76
mouse  CAAGCAGGGTGGAACTCGTGACGGGAAATGGGAACGGCACCCACGAAGGCGTGATTCCT
rat    CAAGCAGGGTGGAATTCGTGACGGGAAATGGGAAACGGTACCCACGAAGGCGTGATTCCT
human  CAGGGTGGA....ACTCGTGACGGGAAATGGGAATGGCACCCAAGAAAGCATGATTTCT
         -0.06kb  CREB/AP1/ATF -0.2/0.04kb TCF1/CREB/AP1/ATF       AREB6
mouse  TGTAGATCCTTGAGTGACGGACGGGTGAGGTTTCCGTCAGGCAAGCCCAGCCACCTTCG
rat    CGTAGCTCCCTGAGTGA.Primer F....GGTTCCATCAGGCAAGCCCGGCCACCTTCG
human  .GTAGTTTCGTGAATGA.....TAGCAAGGCTCCCATCAGACAAGCTGAGCCACTGTCA
         NFKB
                          +1        Alt splice donor              +42
mouse  TGGAGGAGCCCCGGACaagtgtaagt.ttcgcagagctgggg.tctccagcttacttct
rat    TGGAGAAGCGC.GGACAAGTGTAAGT.TTTGCAGAGCTGGGG.TCTCTAGCTTGCTTCT
human  CTGAGGAGGAC..AAACGAGTGCAAGTCTTTGCAAAGCTTGGCATCTCAGACTTGCCTCT
                 Primer G
mouse  ......gctaatgctaccccaggcctttagacggagaacagatggcagatggag
rat    ......GCTAATGCTACCCCAGGCCTTTAGACAGAGAACAGATGGCAGATGGAGTTTCT
human  CATTTCTTGCTTCACACACTAGCCTCTTGGCTAGAGAACAGACATCAGATGGAGTTTCT rat    TATTGCCATGCGCAAACGCTGAGCCCACCTCATCGATCCCGGACCCCATGGTTTTCAGTA
human  TCTGGCTATGCCTGAATGTTAAGCTGAACGTATGTTCCAGGAGCTCGTGGTCTCCAGTA rat    GA..CAACCTGGGCTAAGAAGAGATCTCCGACCTTATAGAGC
human  GAGGCAATCTGGGAT.AGAAGAGAAGATATTTCTTACGTAGAAGACAAGCAA
```

FIG. 25A

>HPRM42377 NM_001293306;name=SCN10A;Entrez_ID=6336;Genome=hg38;chr3-
:38795460-38794009;TSS=38794010;Upstream=1450,Downstream=1;Length=1452;

GCTGAGGTGGGAGAATTGCTTGAGCCCAGGAGACAGAGGTTGCAGTGAGCAGAGATTGCA
CCACTGCACTCTAGTCCGGGTGACAGTGATACCCTGTCTCAAAAAAAAAAAAAGAAAAAG
AAAAAGAAAAAAACAAAAAAGACAAGAACTGAGAAGGGCCCCCTGACTTTAGCCACAAGG
CAATCTCTTGTATCCCTGCAAGGAAGCATTTTAGTGAGATAGGAGGGCAAAATCCAAGCT
TCAAAGACTGAAAAGTGACTGGAAACAGTGAGTAGAAGTAAGTCCTTTATTAAAAGCCAA
TAGAGAACAGGAGAGAGGAGGGAAGACCTGGATGGGCTCTGCATCAAGGGAAAGTTTTTA
AAGTTGGAGGAAAGTTAAGCATCTTTAAATGCTGATAGGAAAGAGCTGGCAGACAAGGAG
AGAGAAAAAATGAGGTAGATATGAGATAAGATCCTAAGCAGAGGGAAAGGAATGGTCCT
TAGAATGTAGGAAGATACCTCTCATGTTGTAAGAGAAGGGAAGGAGGAAAGAAGGCTGCA
GACACAGGTGAGTTGGAGGTTTGATGGTATGAAGTTGGCAGAGTTCTGTTTTTCTCCATG
AACTAGGAAATATGGTCATTGGCTTACTGCAAGGGAAGACAGGGAATAGTGAGAAAAGAG
TGTATTTGAAACCTCAGACTAGAAGAAACTGCTGACTAGGGATACCATATGATTCCCAGG
CAATACTGAGGTTCCCCATAACCCCTCAGCAGTTCAGGGGAACTGTTCTAGATTGACTTA
GCCTTGGGATTTAGGATAAGGGTGAGGGAGTGGCAAAATTGTGGACCACAGGTCTAATCT
GGTTATGGGGAAAAGTGTTCAGCCACAGACTGAACCTGGAGGTCCCAGAGAAATTGGAGG
TCCCAATGAAATTCTCCAATAATCTGGAGTTCTCCAGTAACTTGGAGGTCCAAATGAAAT
TCAAACAGGTGGAGAAATGTTGACAATGTCAATAAATAAAGATTGTGATAAGAAAGTAG
CATGAGACTTAAGATAAAGTAGACTATAAACCAAAGTCTTTGATGAATATGGGAGAGTGC
CTGGAACTCAGTGGTCCTGGAAATGAGGAGAGAGGGCAGCATGGCTAAATCTGGTGGTGG
TGGTAGGATGGTACAAAGTGGTGAAGAAGCAATGACATAGAAGCACATGGGGAGCAAAGA
CATAACCCTGAGGCACCTGGAGGAGGGTTGAATAAACAGCCTCCCCTGAATGCCTTGCAG
GGGAATGGGTTCCTGGGAGGAGCCAAGTGTGAGTTCAGGGAGGGGCCAGATATGAGGGTG
GGAGAAGGGCTGTTCTGACAATCAAGATGGGACAGATGAGAGGGACAGGGCCAGTGGGC
AAGCTGTCACCTCTCTGTGGTTATGTCCACTCTTATAAGAGTATAAATACTTCCTGAAGAA
GAATGAGAAGAT

FIG. 25B: Nav1.8 Promoter SCN10A

ACCACCAATCAGGGAAGAGAAGGCGATTTGTCCAGGATATGGCACTGAGAAT
TATCACAAGTGAGCTAGTTCACCTTCATTGCACAGTCTCAGTCACTGAAGTTT
CCTTCCTTCAATAGCACATCTTACAAGTCAAGAATGTAAGGTCCAAAGCCCCA
GGACAAATCTCAGAAGCAAAGAAAGCAGCAGGGAAAAGTAGACCCTGGGAT
TTGATTTCCTTCCGGTTATCTCTAAGCATCATTTCCATGATAGAAGGTGTGGAA
GCAAATAATAAAAGTGCCCGTCACTAGTGTTTATCCTGCAAAGTGGTCTGCCC
TTTTGAGAGGCACCCTGCCCTATGGCCATCCTTTGATTTCTTCCCTTGGTGGA
AATTTCCTGTTTCTCTTTGAGAAAGATAATTCAACCCTGTTTCCATTGTTCTTC
CTCCCAGGCTGCTGTAGGAAAGCGCACGCACACTCCACACAAAATGAATT
TTTAAAAATTTATTTTCACAGTCGCTCCTACCAGCTCTGAAATTCAGAACCCA
TATGACTGATGGCATATTCAGATAATCGGGTCCCAGGTCTGGAAAAGCAGCCT
TTTCCCCACGTTTCTTTCCCCACCTAGGACCTCCTCTGATTCTTCACTGCATC
TTCGAAAGAAATGTATTATTTGCTTGCCTGGAAGACGCTGCAATTCAATTGAT
TTTATATATACATATATATAAAGAAAACAGAAAACATAGCCTAGATACCGGTCTTG
AGCGTCACCGCCCCACTCGCGGTTGTGAGCAAAGCCCTACGGAAGAAACCA
ATTCCCAGCCTAGACTCTTCAGAGCCCAAGGTCGGGGAGGCGCTGGCCTGG
CGGTGTTGTCTGGCTCCCAGCCACTGCCCCAGACTCAGGGCTTTGCCATT
GGTCCCCACCTCCTCTGCTCCGGAGTTTTCTCCAGCTCCCCACCAAGCCAC
ACAAAGTGACTTCTCGGAAACATTAGCCGATTCTGCTGAGCAGGAAGGGAGG
AAAGGGATGATGGGGGCGGGGGTGAGATAAGGGAAGGGCTCTTCTGGCTG
CTGGACACACACACACACACACTCAAACACACACACGCCCCACCCAATGGGT
GGCCGTGGATGGCAGGTCGTGCAACCCCTCCTCCGCCTTCTATTAGCGCAT
GGTGCAGAGGCTACAGCGTCGCCACCACCGCGCCCTAGCTGGGTCCCCG
CCCTGCGCCGCCCGCAGGAGTGGAGAGAGGGAGGGAGGGAGGGAGCAAG
GGGTGGGGACCCGGGCGCGCTGGGAGGAGTGGAGGAGGCAAAGCGGCGC
AGCTGCCCTCGGGGAGGCGGGGCTGCTACCTCCACGGGCGCGCCCTGGCA
GGAGGGGCGCAGTCTGCTTGCAGGCGGTCGCCAGCGCTCCAGCGGCGGC
TGTCGGCTTTCCAATTCCGCCAGCTCGGCTGAGGCTGGGCTAGCCTGGGTG
CCAGTGGCTGCTAGCGGCAGGCGTCCCTGAGCAACAGGAGCCCAGAGAA
AAAGAAGCAGCCCTGAGAGAGCGCCGGGGA

>HPRM44637
NM_002977;name=SCN9A;Entrez_ID=6335;Genome=hg38;chr2-
:166377308-
166375775;TSS=166375987;Upstream=1321,Downstream=212;Length=15
34

FIG. 26

\>HPRM19294
NM_001012331;name=NTRK1;Entrez_ID=4914;Genome=hg18;chr1+:155095882-155097350;TSS=155097295;Upstream=1413,Downstream=55;Length=1469;

GACATCTGCGGGGTAACTTCTGGCAGCCTCGACCCGGGAGAACGTGGACAGCCCTTGGCCTC
TGGGAGCCCCTCTCAGCCTCCTAGGAGGCCTCCTTGTCCTCTTTGGAGACCCCTTAGCGCCAG
GCTCCGTCACCGCCTAGTCCCTTGGTTCTGACCAAGATCCCGAGGAAGAAGGCGATCACTGTG
TAGGGCTCTGCCTCCGTCTGGTCACCTTCTTGAGCTCAGGCTGCTCGGTCGGTCTGTGTGTCCC
TGTCTCGGGGACTTGGGGGGCCATCCGTGCTGGGGCCTTGGCGGAGAGAACCGTGAGCCTC
TAGGAGGTCGTCCTTCCCCGCTCCCTGGGGCCTTGCCTGTCTCCCGCCAAGAGACACCCCT
CTTCCCTTCGCTCTCCCCAGCTTGAGACGGATGGGTTAGTGCAGCCACGGAGGCTTGCGCGG
TGGGAGGGGTTGGGACCAGCCTTCTGCTGCCCTGGGTGCTGGGGATCCCGGGGCTTTCCAG
GTGCTCGGCCTCCAAGGTGCGCGGTCCTCAGCTCCACCCGCGGGCGGCTCCTGCGTCCGAGG
AGCTAAGAGAAGATCTATTAATTTCTTCACGAATAAATCGATGCTCTTGTCAGGGAGGCGATCG
ATGTCAGCCCTGCCCTGCCTTGCCCTATCCTGCCCCGGGGCCGGCGCTGGCTGGCCGGGGTCA
GGGACTGAAGCTGAGACCTGAGGCGTTGCTCACTGGGGGCTGCAGATCGCACCCCCAGGCA
CCCAGCGCGGGCGGGGAGCTCGCGCCTTTGCGCGCGGGCTTCTCGCGCCACCCTGTGGCTTC
TCTTGGAGGCGCGGTCTTGGCTCTCCGGACTCCCTTCGGCCGGATTAGGCGACCCCTTCCCTT
TCTCTGCCCCGTCTGTGTCTTCCTCCCCAGGTTCTGCGATTGATCCTTTGGTAGTCCTTTTCGTT
TTCTTCCTAGAGTTCGGAGAATGTTCTACCTAACTTACTCCAAGTGACATGCTCACTCCCCTAGG
CACGCGCGCCGCGAGGATGGAGCGCTGAGCCTGGGGCTGGCTAGGATGACCTGGACAGCAA
CCTTTCCTCAACGCAGTCATCTTCCCTCCTCCCCAAATGTAAAAATGCAGCTGCTTTAAGCTGA
GAGAAATAACGTATCAGCTTCCCACCTCCGGCCTCAGCAGACACCTCCGAGGCGTTCTGCTGC
GGCCCCTCAGCGTCTGCCGGAGCTGAGGCGGATCCTCGGGGAGAAGGCTGACGCTGGGGG
CCCCTAACAGGGGAGGGGGCAGAGGGGGGGGCGTCAGAGAGTAGGAAGCGGGTGGAGAA
GAGGGGCAAGGCGGGGCCGGGCGGGGCCGCTGGCTCCGCCCTTTCCTGGCGGCTGGGTC
TTTAACACCGCCCAGCGCACATGTCGGGGGAGGCCTGGCAGCTGCAGCTGGGAGCGCACAG
ACGGCTGCCCCGCCTGAGCGAGGCGGGCGCCGCCGCG

FIG. 27B

```
TAGATGGCGCATGCTCTCCAAACTTGGCTTTGTCCATCAAGGTTCAAGAA
AACAATGGTCAGACATGTTCCTCTTAACAAACAGTATGTCCCCAAACAGCA
AAAATGCATACAGTCCTTTCTGGGTGAATTTTAAATCTTACATAAATCCAT
CAACCCCATCCTTTTTCCTTTGCCTCTTGGGAGAAATTAATCTAGCTTTACA
TTAATTATGCATGTTATCAGATTTCAAGCTCCTTGAGAGCAGGTATTTTAAT
TCTATAAAGCCTCTACGTGGCCTTGGACATGGGAGGTGCTTAATTACCCAA
GATGCTCCTTGAATACAGATGGTACACGACCTACACAGACTTAGATCTTTA
CCACTTCCCCCCTCTCCCCACCCTGACTTGCTCAATCCTGAAGGAACTGGA
GACGTCTAAGTGTCTGAGGTTCACGCTTCCACACAGAAGCTTGGGTCTGT
GTGGGAGGGAAAAGGAAGCCATCTGTCCGCAGGCCAGACCAGGCCAC
ACCCTGCTAGCACCCAGAACCCTTTGTCCCAGGCCCAGCCCTGCCATTTTA
CTTTCCTTGCATCTGGAAAGCACAGGGAATATAGTAGTGACAAAAGAAG
GAAGGGTTGTTTGAGTTTAAGAATAGTTTACTCTAAAAAAAAAAAAAAAA
AAAAAAAAAGGACAAAGCCAAAGAGAAGGTCAAAGTTGACTGTGGAG
AAGGCCTTGCAAGCAGGGAACTTGGGAAGAATTGGAATGAGAGTGAGA
GAAGGCAACTGAGTTTGGAAATATTTTTCTGACTAGCTTTTCTTTCCAAA
TGCCACTGAACTTAGATTGGTTTAGGAAGGGTTGTAGTACATCAAAGTGG
CTAGAAGCACAGGTTTGGGGATCAGATAAGGATTTCATTCTAGAGTGTGA
TCTTGTACAAGTTATTCAGCCTTTGCAAACCTCAGATTCACACAATGTAAG
ATGAAGAAACTCACCTTCTGAAAATTAGAGATAACATATGCAAAGTGAATC
AATACAGGGCTTAACATATTTATCACCCCTTTGGTAAATAACCATGACGATT
ACCAGAGCTCTTAAGGGCAATGGCAGGTGGGAAGCAGAACTCATGGGT
GGTAATCCCCAGGCCAGCCAGGCTCACCATGTGCACTTGGACAAGTCCTT
GCCCCCATCATTGTGAAATGGTGCAGGGATGCACCATGAGGGTGTGGCA
GGATGGCTGACAACAGACTGGGAAGCAGCTCGGCAGAAAACTGGATT
GATGCCCACTATGGCAAGAGATATCATCTCCCTCTTGTTCTGTGATGTTTC
```

>HPRM11438 NM_006576;name=AVIL;Entrez_ID=10677;Genome=hg18;chr12-:56497418-56496112;TSS=56496119;Upstream=1299,Downstream=7;Length=1307;

FIG. 28

ACCGCCCGAGAGACTCGGAGGCAGGCTTGGGACACGTTTGAGTGAACACC
TCAGGATACTCTTCTGGCCAGTATCTGTTTTTTAGTGTCTGTGATTCAGAGTG
GGCACATGTTGGGAGACAGTAATGGGTTTGGGTGTGTGTAAATGAGTGTGA
CCGGAAGCGAGTGTGAGCTTGATCTAGGCAGGGACCACACAGCACTGTCA
CACCTGCCTGCTCTTTAGTAGAGGACTGAAGTGCGGGGGTGGGGGTACGG
GGCCGGAATAGAATGTCTCTGGGACATCTTGGCAAACAGCAGCCGGAAGCA
AAGGGGCAGCTGTGCAAACGGCTCAGGCAGGTGATGGATGGCAGGGTAG
GAAGGGGGAGGTCCAGAGGTCTGGATGGAGGCTTCCGCATCTGTACCTTG
CAACTCACCCCTCAGGCCCAGCAGGTCATCGGCCCCTCCTCACACATGTA
ATGGATCTGAAGAGTACCCCGGGACAGTCCGGGGAGATGGAGATTCGGAA
AGTATCCATGGAGATCTTACAGAATCCCTGTGCGGACCAGGAAACTCTTGT
AGATCCCTGCCTATCTGAGGCCCAGGCGCTGGGCTGTTTCTCACAATATTCC
TTCAAGATGAGATTGTGGTCCCCATTTCAAAGATGAGTACACTGAGCCTCTG
TGAAGTTACTTGCCCATGATCACACAACCAGGAATTGGGCCAACTGTAATTG
AACTCCTGTCTAACAAAGTTCTTGCTCCCAGCTCCGTCTCTTGTTTCCCACG
AGCCCTGGCCCTCTGTGGGTAATACCAGCTACTGGAGTCAGATTTCTTGGG
CCCAGAACCCACCCTTAGGGGCATTAACCTTTAAAATCTCACTTGGGCAGG
GGTCTGGGATCAGAGTTGGAAGAGTCCCTACAATCCTGGACCCTTTCCGCC
AAATCGTGAACCAGGGGTGGAGTGGGGCGAGGGTTCAAAACCAGGCCG
GACTGAGAGGTGAAATTCACCATGACGTCAAACTGCCCTCAAATTCCCGCT
CACTTAAGGGCGTTACTTGTTGGTGCCCCACCATCCCCCACCATTTCCATC
AATGACCTCAATGCAAATACAAGTGGGACGGTCCTGCTGGATCCTCCAGGT
TCTGGAAGCATGAGGGTGACGCAACCCAGGGGCAAAGGACCCCTCCGCCC
ATTGGTTGCTGTGCACTGGCGGAACTTTCCCGACCCACAGCGGCGGGAATA
AGAGCAGTCGCTGGCGCTGGGAGGCATCAGAGACACTGCCCAGCCCAAGT
GTCGCCGCCGCTTCCACAGGGCTCTGGCTGGACGCCGCCGCCGCCGCTG
CCACCGCCTCTGATCCAAGCCACCTCCGCCAGGTGAGCCCGAGATCCT
GGCTCAGGTATATGTCTCTCCCTCCCTCTCCCTCCATTCGTCATTTTCTCACT
CCCTTTCCTCCTCTCCCTCTCTCTCCGTTAGTCTCTTCATCAGATAGTCTCTG
TTAGTCCGCGATTTATACCAGGCTCGTGCCCTAGGTTGGATCGGACAGTCTC
AATCCCCGGCTCGCTCTTCCTGCT

>HPRM32750 NM_001033952;name=CALCA;Entrez_ID=796;Genome=hg38;chr11-:14973599-14972045;TSS=14972286;Upstream=1313,Downstream=241;Length=1555

FIG. 29

>HPRM18949
NM_133445;name=GRIN3A;Entrez_ID=116443;Genome=hg18;chr9-:103541815-103540519;TSS=103540683;Upstream=1132,Downstream=164;Length=1297;

GGCTGGGGAAAACAGCATTCACTTTGCAAGCTTCTTGGGATTTTTACTTAACTA
GAGTCTCTTCTTCCCAGGATTTAAAACATGATGGAAACTTTAGCTCATGAATCAA
AACAACCCTCCAGAGCTAAAAGCCAGCTGTATTTGCATAACAATTTAGCAGATC
CAAACAGCAGGGCAAGGTCGGGTGAAATAAGTTGCCAAGGTCATGGTCATGA
AGTAGTATTAGACTCAGAAAGGCTGATCCCCAGTGCTTGCTCCACCCCATGGAT
CTCTCCTACCCTCCTTCTAAACGATACTGTGGGATAAAATAAAATTAATCTACTGT
ATATGTGCAAACCACAGGCCTGCCCTTAACTCTTTCCTTACCTTCTAGTTTCAGAT
TATTCAAATCATGGAGGAAAAGATTAGATCACAACACGTTGACTTCACTGTATTA
CCATACAAATGAAATAACTTAGTACAAACTGTGATCTGGGGACTCTTGATCTAAA
CTGGGAACTGCTGTTGACTGCATTTTAAACTCTAAAAGTATTTTGAAACTCTTTA
ATTTCTTGAACTGAAAAAATTGCTTGAATTCACTTTGTTTAATTCTGAGAACC
TAAAAACAGGGATTCTTTAAAAAAAAAATGCAAAGGCTCACATGCCAGAAAGA
AAGAAGCTGAGGAGATAAAAATGTGTAAATAATTCTTACTTTAATACCCTTAGCT
AGAAAAACCTTAAAAGCGACACATCCAGAAGCTCGTTAAGTCACAGCCTCTTT
GAACCTATTTCAGTGAACCACCGAATTTCAGATCCCTCAGGTGCGACTCTGAAT
TCAGAATTCTCACCGGCTCATAGTCCTATTTTCCTTCTTAGGTTTTAGGGAATTTT
GCAAACTATGACGCCCAGCCTTTGAGGGGAGAGGACTTTCCAGGGGCGCGGG
ATGTGCCACTCGGGAATCTCACCAACAGTGGGCGTTTAGCGCAGCCAAGCGAC
AGGCAGGCGCCAGGGCTCAGCAACAGGGAGGCGCCGGCTGAGGCGGGGAG
AACTTTGGCGCTCGGAGCAGAGCCACCCTTTGCTGGCCAGTCGCGTTGCTCCT
CCGAGGAAGCAAGCGGCGGTGGCGACTCGGTGGAAAAATAACGAAAGAAAG
GCAGAGAGGAAGTAGCGAGAGAAGAGAGAAAATGAAGTCGGCGCTGGGGG
AGCCTGCAGGAGGGTGGCCAACAGTGGAGGAAGGTGGATTTGGCTTCTTTTC
CGCACCCCGGGCGTGAAAGCCCTCTCCAACGCGACCCCAGGAAATAAGTGGG
TCTCGCCTGGGC

FIG. 30

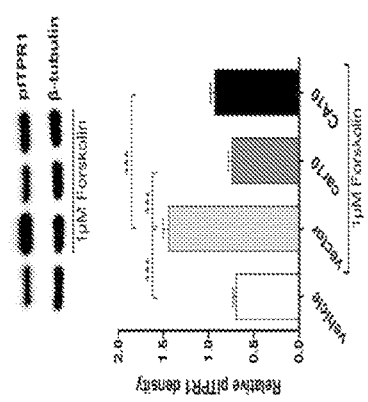
FIG. 34B
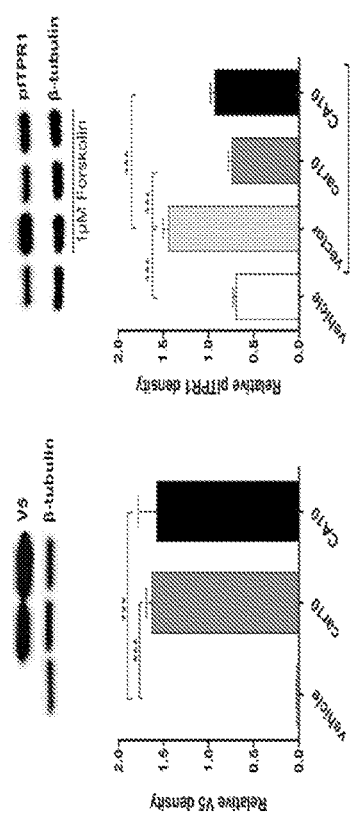
FIG. 34A
FIG. 36
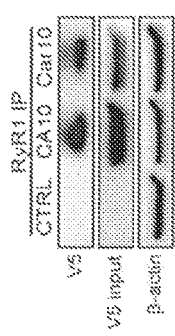
FIG. 33
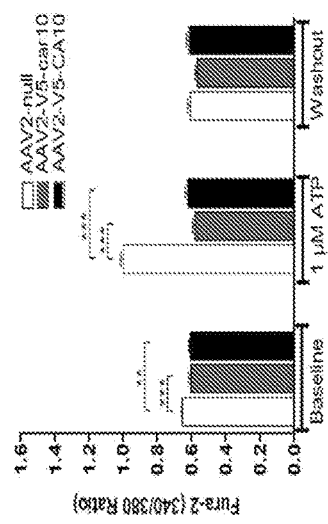
FIG. 35

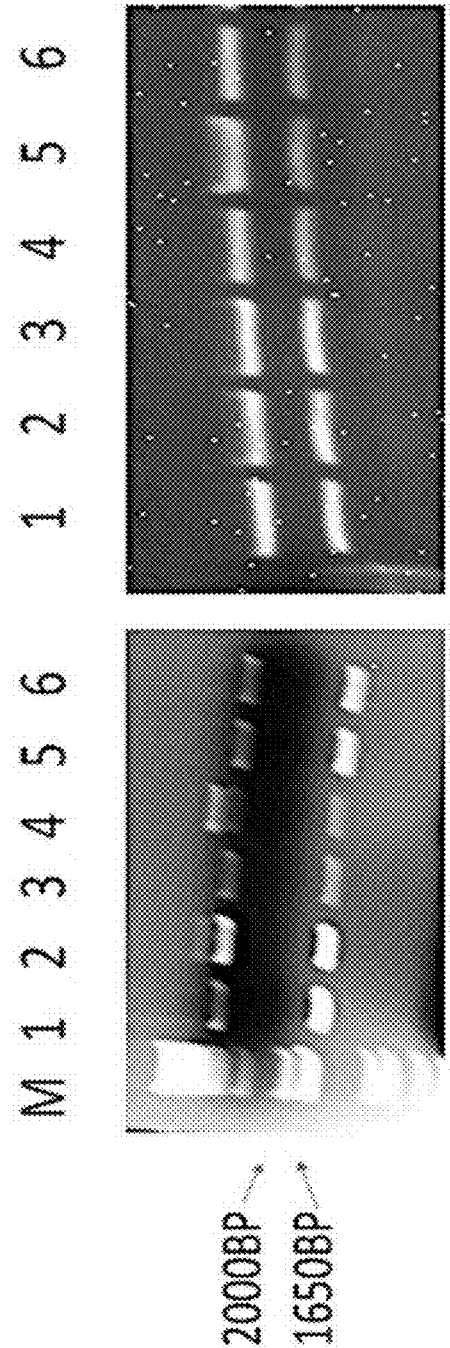
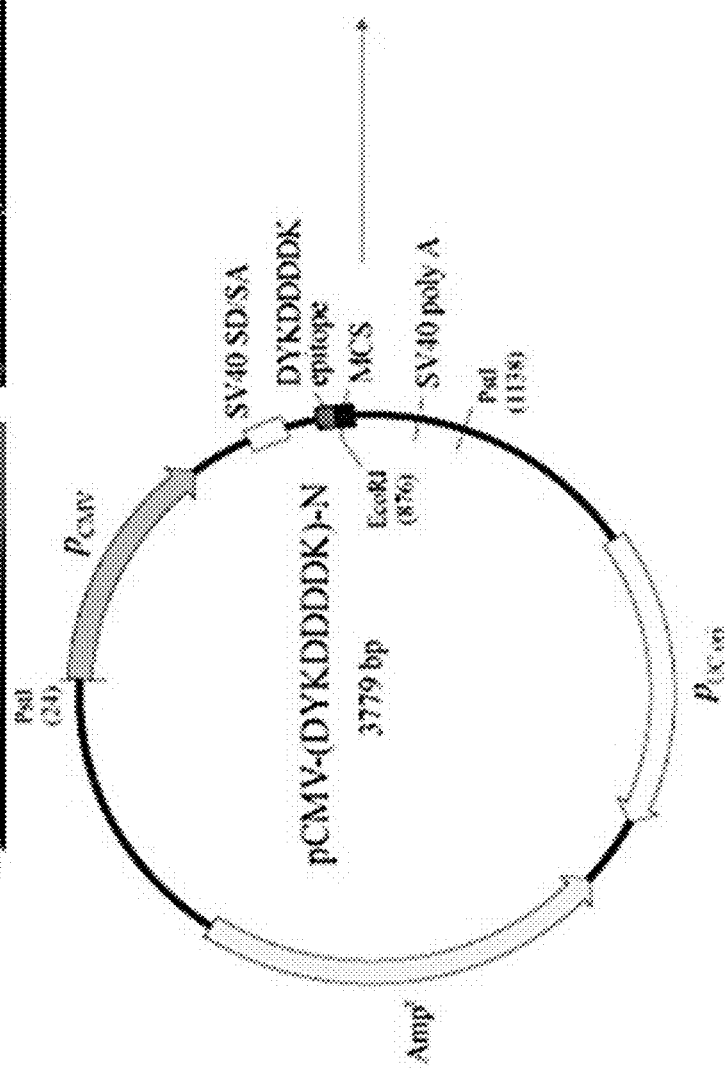
FIG. 38

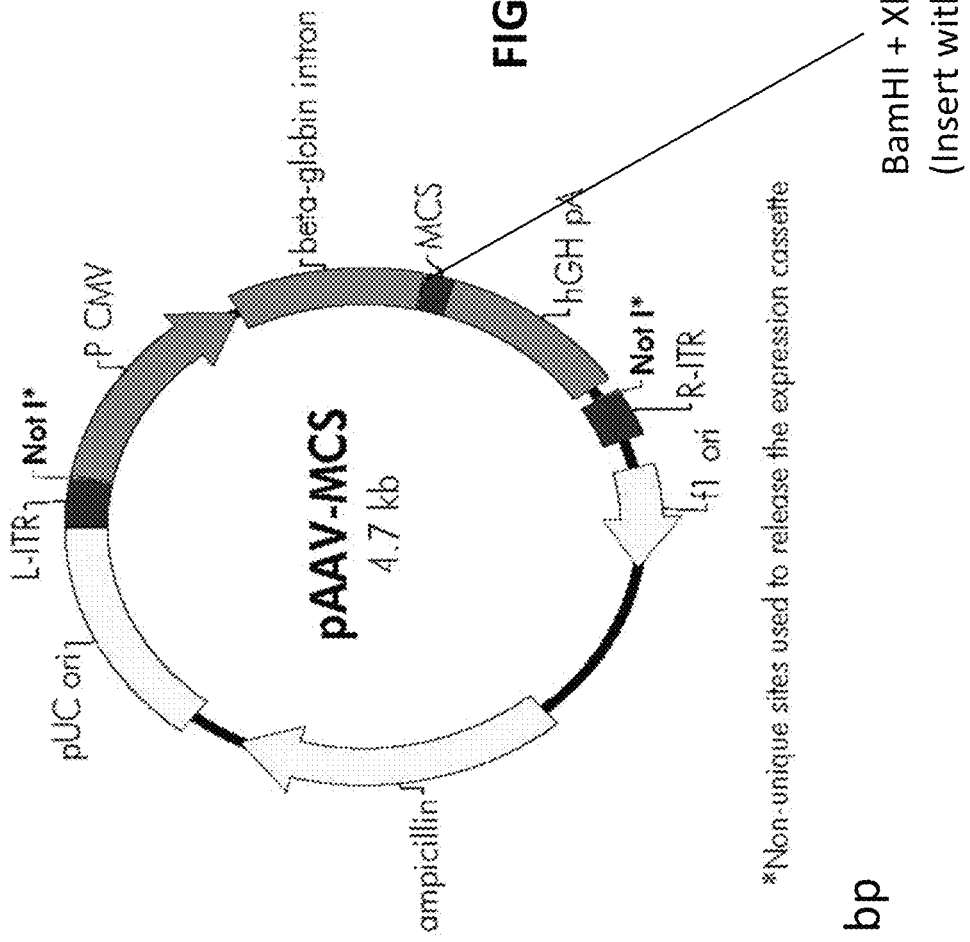
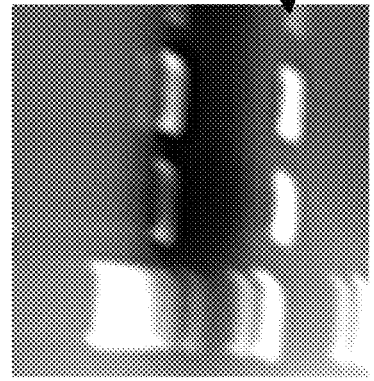
FIG. 39

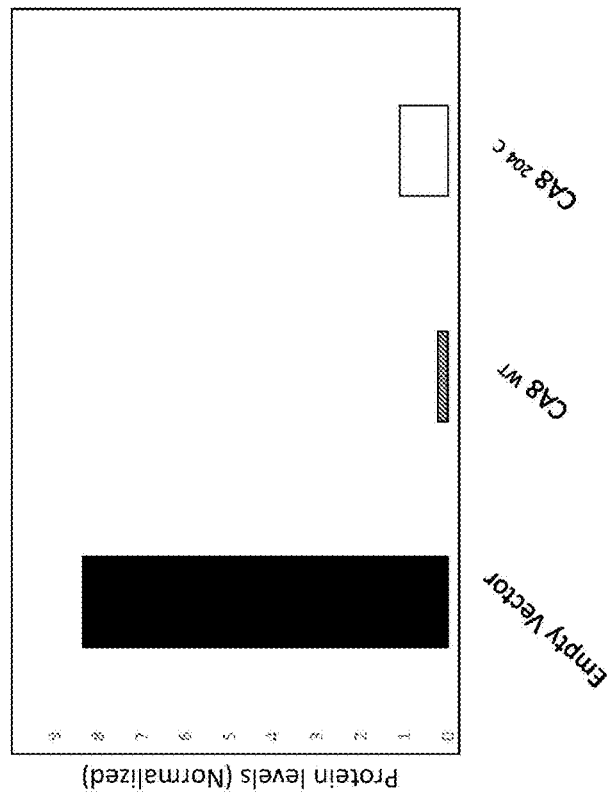
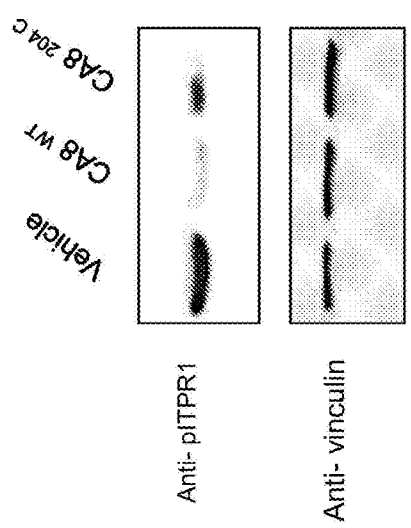
FIG. 45

SEQUENCE LISTING

<160> NUMBER OF SEQ ID NOS: 35

<210> SEQ ID NO 1
<211> LENGTH: 455
<212> TYPE: DNA
<213> ORGANISM: Homo sapiens

<400> SEQUENCE: 1

```
tgctgccgag agcgccgagg ggccccgcgg ccttcccatg gcggacctga gcttcatcga      60
agataccgtc gccttccccg agaaggaaga ggatgaggag gaagaagagg agggtgtgga     120
gtggggctac gaggaaggtg ttgagtgggg tctggtgttt cctgatgcta atggggaata     180
ccagtctcct attaacctaa actcaagaga ggctaggtat gaccccctcgc tgttggatgt    240 ccgcctctcc ccaaattatg tggtgtgccg agactgtgaa gtcaccaatg atggacatac     300
cattcaggtt atcctgaagt caaaatcagt tctttcggga ggaccattgc ctcaagggca     360
tgaatttgaa ctgtacgaag tgagatttca ctggggaaga gaaaaccagc gtggttctga     420
gcacacggtt aatttcaaag cttttcccat ggagg                                455

<210> SEQ ID NO 2
<211> LENGTH: 594
<212> TYPE: DNA
<213> ORGANISM: Homo sapiens

<400> SEQUENCE: 2
aacgcacgcc tgcttgcact cacactgcgg ttcacacccg caggcgctct cgcactcaca      60
ctgccgctcc gcgtgctcac actccccac gcgcgctccg ctccggctcc agccccgcgc     120
ccagcgaagg cgcaggcact gctgccgaga gcgccgaggg gccccgcggc cttcccatgg     180
cggacctgag cttcatcgaa gataccgtcg ccttccccga gaaggaagag gatgaggagg     240
aagaagagga gggtgtggag tggggctacg aggaaggtgt tgagtggggt ctggtgtttc     300
ctgatgctaa tggggaatac cagtctccta ttaacctaaa ctcaagagag gctaggtatg     360 accccctcgct gttggatgtc cgcctctccc caaattatgt ggtgtgccga gactgtgaag    420
tcaccaatga tggacatacc attcaggtta tcctgaagtc aaaatcagtt ctttcgggag     480
gaccattgcc tcaagggcat gaatttgaac tgtacgaagt gagatttcac tggggaagag     540
aaaaccagcg tggttctgag cacacggtta atttcaaagc ttttcccatg gagg           594

<210> SEQ ID NO 3
<211> LENGTH: 3260
<212> TYPE: DNA
<213> ORGANISM: Homo sapiens
<300> PUBLICATION INFORMATION:
<308> DATABASE ACCESSION NUMBER: NCBI / NM_020178.4
<309> DATABASE ENTRY DATE: 2014-06-25
<313> RELEVANT RESIDUES IN SEQ ID NO: (1)..(3260)

<400> SEQUENCE: 3
ctctctgagt tgggaagcgt agggatccgt aggcgaggaa ataacgaccc ctgcagttgt      60
attgcggaaa atctcgacag cggcgctagt tgcgggcgat ggaagccagg caactggggg    120
ttctggggag ttcaggaaaa tagcagagga gcaggaaggg cgcgcgcgac ctggagagtc    180
tgtgtgcccc caccgcgccc cagtccccgg gcccagccc ttcccctcgg cgccctggac     240
gcactgccga aacccggctg agaggctgca ggctgcgcgc ggacctgggg agcagggagg    300
gtcggcggag gctgccggcg gctggcggtt tcgggcaata atccctgcct ctctttctct    360
gtgtgtctgc tgtgtctgct ccttcccccgc cccccggaag caggagaaga actgccccgg   420
agcgcagcag ccaccctccg accatgcccc ggtgaggggg gcggacttcg agggcaactt    480
gccgcggact gcctgggctt agccagcgag ctacgcgctc ccgggagccc ggaattgcac    540
ggcgcagccc ggcgggggc tatcgtctat gtcttcttgg ggcgccagac gaatcggggt     600 ctcgttttg ctggaagagc ccagtgttgg tggcttcagg tggctgctgc cgccgccgcc     660
```

```
gccgccgccg ctgctagtgc ggtttccgcc gctggtgcga agagaagaga cacgcgagcg    720
gggagacctc caaggcagcg aggcatcgga catgtgtcag cacatctggg gcgcacatcc    780
gtcgagcccg aggggagatt tgccggaaca attcaaactg cgatattgat cttggggtg     840 actgtccctg gccggctgtc gggtgggagt gcgagtgtgc actcgctcgg aagtgtgtgc    900
gagtgtgtat gtgtgtgtgc cgtgtcgggc tcccccttc ccccgttttt cccgtcgagt     960
gatgcacttg gaatgagaat cagaggatgg aaatagtctg ggaggtgctt tttcttcttc    1020
aagccaattt catcgtctgc atatcagctc aacagaattc accaaaaatc catgaaggct    1080
ggtgggcata caaggaggtg gtccagggaa gctttgttcc agttccttct ttctggggat    1140
tggtgaactc agcttggaat cttgctctg tggggaaacg gcagtcgcca gtcaacatag    1200
agaccagtca catgatcttc gaccccttc tgacacctct tcgcatcaac acgggggca      1260 ggaaggtcag tgggaccatg tacaacactg gaagacacgt atcccttcgc ctggacaagg    1320
agcacttggt caacatatct ggagggccca tgcatacag ccaccggctg gaggagatcc     1380
gactacactt tgggagtgag gacagccaag ggtcggagca cctcctcaat ggacaggcct    1440
tctctgggga ggtgcagctc atccactata accatgagct atatacgaat gtcacagaag    1500
ctgcaaagag tccaaatgga ttggtggtag tttctatatt tataaaagtt tctgattcat    1560
caaacccatt tcttaatcga atgctcaaca gagatactat cacaagaata acatataaaa    1620
atgatgcata tttactacag gggcttaata tagaggaact atatccagag acctctagtt    1680
tcatcactta cgatgggtcg atgactatcc caccctgcta tgagacagca agttggatca    1740
taatgaacaa acctgtctat ataaccagga tgcagatgca ttccttgcgc ctgctcagcc    1800
agaaccagcc atctcagatc tttctgagca tgagtgacaa cttcaggcct gtccagccac    1860
tcaacaaccg ctgcatccgc accaatatca acttcagttt acaggggaag gactgtccaa    1920
acaaccgagc ccagaagctt cagtatagag taaatgaatg gctcctcaag tagggaacaa    1980
agccaagaag aatcccacct cagtgaaatg ctacaactgt gaattgacgt aacctagaat    2040 gtccccttc ttgcttctct ctccttcttt ccccaagcc tcattcattc ttgggattgg      2100
ccctttcttc atgaaaagtg tctgcaaaac catggcagag gaatacatct ctcacacata    2160
ctcacaaaca cacacacaag cacttgcaca tacatacaaa cacatgcaaa catacctaca    2220
cacacacaca ctcttacaac ctccatcatg ggaagtcaag tttcagaaac aaaagtctca    2280
ttcataagag gtcttagaag aaaataacca gttaacctga tttcaatttt gataccgttt    2340
tcctgaacta ataaatctac ccaatgagac ttttcagcct ttgtacatac aaaattcttc    2400
caaaagagag aggagaaaat acagctctga tggcatcaaa cggactttgc atcaagtaat    2460
ttcagatagt gtcctaggat cctttgaggg tgctggtagc aggtgagcag acaaagttg     2520 accaaggaca cttatttcta gattatgatt cttctgttta ctcaacaatt tacaaagaaa    2580
aaaaggacag acattgaaga gctacacatt gtatatatat caccacagac tataaggaaa    2640
tggaattatt tccctctttg tcacatatct gtagtaggat ttgccaagat cagaaatgat    2700
ccatttgctg tttcttgttt tccaaaggtc atacattgtg tttggttatt gttaccagct    2760
caataaatgt gtttaacgag ttaatttcat ttttctggct ttggtctgtt ctccttcctt    2820
acaggctaag ccctggctcc atgcaactgc attctttgat ttcacttgtt ccttcatcta    2880
catgttttgt tcatttgcag ccagtttta ctgagtttgt ggcaatcagg aatgcatttg     2940
ctaagcaagt atgactttaa ttccactcca tggctcaatc attcacatga ggtgagcttc    3000
agcctgagat agcaggcgac agacttcttg cgtttcaaaa ctgccatgcc ccctgtgat     3060
```

-continued

```
gctcccgtga aggaatgcac tttgccttgt aagttcctgg gaaagggta tgttttctct    3120 ccaggtgcag ccagatctca caaagtacaa acgaatgcc tttcttttct tgtttataat    3180
ggtcactcac tgtgtttggt tactgtcaag aaatcaataa atgtgtttaa caagttaccc    3240
agtaaaaaaa aaaaaaaaaa                                                3260
```

<210> SEQ ID NO 4
<211> LENGTH: 328
<212> TYPE: PRT
<213> ORGANISM: Homo sapiens
<300> PUBLICATION INFORMATION:
<308> DATABASE ACCESSION NUMBER: NCBI / NP_064563.1
<309> DATABASE ENTRY DATE: 2014-06-25
<313> RELEVANT RESIDUES IN SEQ ID NO: (1)..(328)

<400> SEQUENCE: 4

```
Met Glu Ile Val Trp Glu Val Leu Phe Leu Leu Gln Ala Asn Phe Ile
1               5                   10                  15

Val Cys Ile Ser Ala Gln Gln Asn Ser Pro Lys Ile His Glu Gly Trp
            20                  25                  30

Trp Ala Tyr Lys Glu Val Val Gln Gly Ser Phe Val Pro Val Pro Ser
        35                  40                  45

Phe Trp Gly Leu Val Asn Ser Ala Trp Asn Leu Cys Ser Val Gly Lys
    50                  55                  60

Arg Gln Ser Pro Val Asn Ile Glu Thr Ser His Met Ile Phe Asp Pro
65                  70                  75                  80

Phe Leu Thr Pro Leu Arg Ile Asn Thr Gly Gly Arg Lys Val Ser Gly
                85                  90                  95

Thr Met Tyr Asn Thr Gly Arg His Val Ser Leu Arg Leu Asp Lys Glu
            100                 105                 110

His Leu Val Asn Ile Ser Gly Gly Pro Met Thr Tyr Ser His Arg Leu
        115                 120                 125

Glu Glu Ile Arg Leu His Phe Gly Ser Glu Asp Ser Gln Gly Ser Glu
    130                 135                 140

His Leu Leu Asn Gly Gln Ala Phe Ser Gly Glu Val Gln Leu Ile His
145                 150                 155                 160

Tyr Asn His Glu Leu Tyr Thr Asn Val Thr Glu Ala Ala Lys Ser Pro
                165                 170                 175

Asn Gly Leu Val Val Val Ser Ile Phe Ile Lys Val Ser Asp Ser Ser
            180                 185                 190

Asn Pro Phe Leu Asn Arg Met Leu Asn Arg Asp Thr Ile Thr Arg Ile
        195                 200                 205

Thr Tyr Lys Asn Asp Ala Tyr Leu Leu Gln Gly Leu Asn Ile Glu Glu
    210                 215                 220

Leu Tyr Pro Glu Thr Ser Ser Phe Ile Thr Tyr Asp Gly Ser Met Thr
225                 230                 235                 240

Ile Pro Pro Cys Tyr Glu Thr Ala Ser Trp Ile Ile Met Asn Lys Pro
                245                 250                 255

Val Tyr Ile Thr Arg Met Gln Met His Ser Leu Arg Leu Leu Ser Gln
            260                 265                 270

Asn Gln Pro Ser Gln Ile Phe Leu Ser Met Ser Asp Asn Phe Arg Pro
        275                 280                 285

Val Gln Pro Leu Asn Asn Arg Cys Ile Arg Thr Asn Ile Asn Phe Ser
    290                 295                 300

Leu Gln Gly Lys Asp Cys Pro Asn Asn Arg Ala Gln Lys Leu Gln Tyr
```

| | | | | |
|---|---|---|---|---|
| 305 | 310 | 315 | 320 | |

Arg Val Asn Glu Trp Leu Leu Lys
            325

<210> SEQ ID NO 5
<211> LENGTH: 2951
<212> TYPE: DNA
<213> ORGANISM: Homo sapiens
<300> PUBLICATION INFORMATION:
<308> DATABASE ACCESSION NUMBER: NCBI / NM_001082534.1
<309> DATABASE ENTRY DATE: 2017-06-25
<313> RELEVANT RESIDUES IN SEQ ID NO: (1)..(2951)

<400> SEQUENCE: 5

| | |
|---|---|
| acagttccca atcgggacaa gcgcgccgag aaatcctgga tcttcccagg gattccctct | 60 |
| acgctccctc ctcttcttca ataacccaa agaggagaag aactgccccg gagcgcagca | 120 |
| gccaccctcc gaccatgccc cggtgagggg ggcggacttc gagggcaact tgccgcggac | 180 |
| tgcctgggct tagccagcga gctacgcgct cccgggagcc cggaattgca cggcgcagcc | 240 |
| cggcgggggg ctatcgtcta tgtcttcttg gggcgccaga cgaatcgggg tctcgttttt | 300 |
| gctggaagag cccagtgttg gtggcttcag gtggctgctg ccgccgccgc cgccgccgcc | 360 |
| gctgctagtg cggtttccgc cgctggtgcg aagagaagag acacgcgagc ggggagacct | 420 |
| ccaaggcagc gaggcatcgg acatgtgtca gcacatctgg ggcgcacatc cgtcgagccc | 480 |
| gaggggagat ttgccggaac aattcaaact gcgatattga tcttgggggt gactgtccct | 540 |
| ggccggctgt cgggtgggag tgcgagtgtg cactcgctcg gaagtgtgtg cgagtgtgta | 600 |
| tgtgtgtgtg ccgtgtcggg ctccccctt ccccccgttt tcccgtcgag tgatgcactt | 660 |
| ggaatgagaa tcagaggatg gaaatagtct gggaggtgct tttcttctt caagccaatt | 720 |
| tcatcgtctg catatcagct caacagaatt caccaaaaat ccatgaaggc tggtgggcat | 780 |
| acaaggaggt ggtccaggga agctttgttc cagttcctc tttctgggga ttggtgaact | 840 |
| cagcttggaa tctttgctct gtggggaaac ggcagtcgcc agtcaacata gagaccagtc | 900 |
| acatgatctt cgacccctt ctgacacctc ttcgcatcaa cacgggggc aggaaggtca | 960 |
| gtgggaccat gtacaacact ggaagacacg tatcccttcg cctggacaag gagcacttgg | 1020 |
| tcaacatatc tggagggccc atgacataca gccaccggct ggaggagatc cgactacact | 1080 |
| ttgggagtga ggacagccaa gggtcggagc acctcctcaa tggacaggcc ttctctgggg | 1140 |
| aggtgcagct catccactat aaccatgagc tatatacgaa tgtcacagaa gctgcaaaga | 1200 |
| gtccaaatgg attggtggta gtttctatat ttataaaagt ttctgattca tcaaacccat | 1260 |
| ttcttaatcg aatgctcaac agagatacta tcacaagaat aacatataaa aatgatgcat | 1320 |
| atttactaca ggggcttaat atagaggaac tatatccaga gacctctagt ttcatcactt | 1380 |
| acgatgggtc gatgactatc ccaccctgct atgagacagc aagttggatc ataatgaaca | 1440 |
| aacctgtcta tataaccagg atgcagatgc attccttgcg cctgctcagc cagaaccagc | 1500 |
| catctcagat cttctgagc atgagtgaca acttcaggcc tgtccagcca ctcaacaacc | 1560 |
| gctgcatccg caccaatatc aacttcagtt tacagggggaa ggactgtcca aacaaccgag | 1620 |
| cccagaagct tcagtataga gtaaatgaat ggctcctcaa gtagggaaca aagccaagaa | 1680 |
| gaatcccacc tcagtgaaat gctacaactg tgaattgacg taacctagaa tgtcccccttc | 1740 |
| cttgcttctc tctccttctt tccccccaagc ctcattcatt cttgggattg gcccctttctt | 1800 |
| catgaaaagt gtctgcaaaa ccatggcaga ggaatacatc tctcacacat actcacaaac | 1860 |

-continued

```
acacacacaa gcacttgcac atacatacaa acacatgcaa acatacctac acacacacac      1920
actcttacaa cctccatcat gggaagtcaa gtttcagaaa caaaagtctc attcataaga      1980
ggtcttagaa gaaaataacc agttaacctg atttcaattt tgataccgtt ttcctgaact      2040
aataaatcta cccaatgaga cttttcagcc tttgtacata caaaattctt ccaaaagaga      2100
gaggagaaaa tacagctctg atggcatcaa acggactttg catcaagtaa tttcagatag      2160
tgtcctagga tcctttgagg gtgctggtag caggtgagca ggacaaagtt gaccaaggac      2220
acttatttct agattatgat tcttctgttt actcaacaat ttacaaagaa aaaaaggaca      2280
gacattgaag agctacacat tgtatatata tcaccacaga ctataaggaa atggaattat      2340
ttccctcttt gtcacatatc tgtagtagga tttgccaaga tcagaaatga tccatttgct      2400
gtttcttgtt ttccaaaggt catacattgt gtttggttat tgttaccagc tcaataaatg      2460
tgtttaacga gttaatttca tttttctggc tttggtctgt tctccttcct tacaggctaa      2520
gccctggctc catgcaactg cattctttga tttcacttgt tccttcatct acatgttttg      2580
ttcatttgca gccagttttt actgagtttg tggcaatcag gaatgcattt gctaagcaag      2640
tatgacttta attccactcc atggctcaat cattcacatg aggtgagctt cagcctgaga      2700
tagcaggcga cagacttctt gcgtttcaaa actgccatgc ccccctgtga tgctcccgtg      2760
aaggaatgca ctttgccttg taagttcctg ggaaggggt atgttttctc tccaggtgca      2820
gccagatctc acaagtaca aaacgaatgc ctttctttc ttgtttataa tggtcactca      2880
ctgtgtttgg ttactgtcaa gaaatcaata aatgtgttta acaagttacc cagtaaaaaa      2940 aaaaaaaaa a                                                             2951
```

<210> SEQ ID NO 6
<211> LENGTH: 328
<212> TYPE: PRT
<213> ORGANISM: Homo sapiens
<300> PUBLICATION INFORMATION:
<308> DATABASE ACCESSION NUMBER: NCBI / NP_001076003.1
<309> DATABASE ENTRY DATE: 2017-06-25
<313> RELEVANT RESIDUES IN SEQ ID NO: (1)..(328)

<400> SEQUENCE: 6

```
Met Glu Ile Val Trp Glu Val Leu Phe Leu Leu Gln Ala Asn Phe Ile
1               5                   10                  15

Val Cys Ile Ser Ala Gln Gln Asn Ser Pro Lys Ile His Glu Gly Trp
            20                  25                  30

Trp Ala Tyr Lys Glu Val Val Gln Gly Ser Phe Val Pro Val Pro Ser
        35                  40                  45

Phe Trp Gly Leu Val Asn Ser Ala Trp Asn Leu Cys Ser Val Gly Lys
    50                  55                  60

Arg Gln Ser Pro Val Asn Ile Glu Thr Ser His Met Ile Phe Asp Pro
65                  70                  75                  80

Phe Leu Thr Pro Leu Arg Ile Asn Thr Gly Gly Arg Lys Val Ser Gly
                85                  90                  95

Thr Met Tyr Asn Thr Gly Arg His Val Ser Leu Arg Leu Asp Lys Glu
            100                 105                 110

His Leu Val Asn Ile Ser Gly Gly Pro Met Thr Tyr Ser His Arg Leu
        115                 120                 125

Glu Glu Ile Arg Leu His Phe Gly Ser Glu Asp Ser Gln Gly Ser Glu
    130                 135                 140

His Leu Leu Asn Gly Gln Ala Phe Ser Gly Glu Val Gln Leu Ile His
145                 150                 155                 160
```

```
Tyr Asn His Glu Leu Tyr Thr Asn Val Thr Glu Ala Ala Lys Ser Pro
                165                 170                 175

Asn Gly Leu Val Val Ser Ile Phe Ile Lys Val Ser Asp Ser Ser
            180                 185                 190

Asn Pro Phe Leu Asn Arg Met Leu Asn Arg Asp Thr Ile Thr Arg Ile
        195                 200                 205

Thr Tyr Lys Asn Asp Ala Tyr Leu Leu Gln Gly Leu Asn Ile Glu Glu
    210                 215                 220

Leu Tyr Pro Glu Thr Ser Ser Phe Ile Thr Tyr Asp Gly Ser Met Thr
225                 230                 235                 240

Ile Pro Pro Cys Tyr Glu Thr Ala Ser Trp Ile Ile Met Asn Lys Pro
                245                 250                 255

Val Tyr Ile Thr Arg Met Gln Met His Ser Leu Arg Leu Leu Ser Gln
            260                 265                 270

Asn Gln Pro Ser Gln Ile Phe Leu Ser Met Ser Asp Asn Phe Arg Pro
        275                 280                 285

Val Gln Pro Leu Asn Asn Arg Cys Ile Arg Thr Asn Ile Asn Phe Ser
    290                 295                 300

Leu Gln Gly Lys Asp Cys Pro Asn Asn Arg Ala Gln Lys Leu Gln Tyr
305                 310                 315                 320

Arg Val Asn Glu Trp Leu Leu Lys
                325

<210> SEQ ID NO 7
<211> LENGTH: 3386
<212> TYPE: DNA
<213> ORGANISM: Homo sapiens
<300> PUBLICATION INFORMATION:
<308> DATABASE ACCESSION NUMBER: NCBI / NM_001082533.1
<309> DATABASE ENTRY DATE: 2017-06-25
<313> RELEVANT RESIDUES IN SEQ ID NO: (1)..(3386)

<400> SEQUENCE: 7
ttcaattccc ctgcatccac actgcaaccg ggtgcaagtc tttcctaggt tatagacagc      60
ccgcctcccc acgagacctt ctgcggactg gctgccccctg gcctcggcct gggtgggtgg     120
gtggtgctcg cgccgccccct actttcccct ggggccctgg agagccgcgc gctgggtgtg    180
tgtgtgtgtg cgcgcgcggg tttggtgggg aaatctcctt cagtggaagc tgctgagtgt    240
cgttggcgga agtatcctg gagcccagca aaagcctcca agcactaga gcttccctaa       300 agaaaagcag aataaaagaa agacaagaag ggaagcccgt tcctctaaag cccgggtttc     360
caatagtccc ggatcctcct ggagttgggc gaaggcgcag ttggcagcag ccgctgctgg    420
cacccggact tggaaaggcg gtgttccccc ttttcgggag gagggaggca gggacttgca    480
ggcaagagtt gcacctggtc taggaacctg cagagaaaag aactctgggg agaagaactg    540
ccccggagcg cagcagccac cctccgacca tgccccggtg agggggggcgg acttcgaggg    600 caacttgccg cggactgcct gggcttagcc agcgagctac gcgctcccgg gagcccggaa    660
ttgcacggcg cagcccggcg gggggctatc gtctatgtct tcttggggcg ccagacgaat    720
cggggtctcg ttttgctgg aagagcccag tgttggtggc ttcaggtggc tgctgccgcc    780
gccgccgccg ccgccgctgc tagtgcggtt ccgccgctg gtgcgaagag aagagacacg    840
cgagcgggga gacctccaag gcagcgagga atcggacatg tgtcagcaca tctgggcgc    900 acatccgtcg agcccgaggg gagatttgcc ggaacaattc aaactgcgat attgatcttg    960
ggggtgactg tccctggccg gctgtcgggt gggagtgcga gtgtgcactc gctcggaagt   1020
```

```
gtgtgcgagt gtgtatgtgt gtgtgccgtg tcgggctccc cccttccccc cgttttcccg    1080
tcgagtgatg cacttggaat gagaatcaga ggatggaaat agtctgggag gtgcttttc     1140 ttcttcaagc caatttcatc gtctgcatat cagctcaaca gaattcacca aaaatccatg    1200
aaggctggtg ggcatacaag gaggtggtcc agggaagctt tgttccagtt ccttctttct    1260
ggggattggt gaactcagct tggaatcttt gctctgtggg gaaacggcag tcgccagtca    1320
acatagagac cagtcacatg atcttcgacc cctttctgac acctcttcgc atcaacacgg    1380
ggggcaggaa ggtcagtggg accatgtaca acactggaag acacgtatcc cttcgcctgg    1440
acaaggagca cttggtcaac atatctggag ggcccatgac atacagccac cggctggagg    1500
agatccgact acactttggg agtgaggaca gccaagggtc ggagcacctc ctcaatggac    1560
aggccttctc tggggaggtg cagctcatcc actataacca tgagctatat acgaatgtca    1620
cagaagctgc aaagagtcca aatggattgg tggtagtttc tatatttata aaagtttctg    1680
attcatcaaa cccatttctt aatcgaatgc tcaacagaga tactatcaca agaataacat    1740
ataaaaatga tgcatattta ctacaggggc ttaatataga ggaactatat ccagagacct    1800
ctagtttcat cacttacgat gggtcgatga ctatcccacc ctgctatgag acagcaagtt    1860
ggatcataat gaacaaacct gtctatataa ccaggatgca gatgcattcc ttgcgcctgc    1920
tcagccagaa ccagccatct cagatctttc tgagcatgag tgacaacttc aggcctgtcc    1980
agccactcaa caaccgctgc atccgcacca atatcaactt cagtttacag gggaaggact    2040
gtccaaacaa ccgagcccag aagcttcagt atagagtaaa tgaatggctc ctcaagtagg    2100
gaacaaagcc aagaagaatc ccacctcagt gaaatgctac aactgtgaat tgacgtaacc    2160
tagaatgtcc cccttcttgc ttctctctcc ttctttcccc caagcctcat tcattcttgg    2220
gattggccct ttcttcatga aaagtgtctg caaaaccatg gcagaggaat acatctctca    2280
cacatactca caaacacaca cacaagcact tgcacataca tacaaacaca tgcaaacata    2340
cctacacaca cacacactct tacaacctcc atcatgggaa gtcaagtttc agaaacaaaa    2400
gtctcattca taagaggtct tagaagaaaa taaccagtta acctgatttc aattttgata    2460
ccgttttcct gaactaataa atctacccaa tgagactttt cagcctttgt acatacaaaa    2520
ttcttccaaa agagagagga gaaaatacag ctctgatggc atcaaacgga ctttgcatca    2580
agtaatttca gatagtgtcc taggatcctt tgagggtgct ggtagcaggt gagcaggaca    2640
aagttgacca aggacactta tttctagatt atgattcttc tgtttactca acaatttaca    2700
aagaaaaaaa ggacagacat tgaagagcta cacattgtat atatatcacc acagactata    2760
aggaaatgga attatttccc tctttgtcac atatctgtag taggatttgc caagatcaga    2820
aatgatccat ttgctgtttc ttgttttcca aaggtcatac attgtgtttg gttattgtta    2880
ccagctcaat aaatgtgttt aacgagttaa tttcattttt ctggctttgg tctgttctcc    2940
ttccttacag gctaagccct ggctccatgc aactgcattc tttgatttca cttgttcctt    3000
catctacatg ttttgttcat ttgcagccag ttttttactga gtttgtggca atcaggaatg    3060
catttgctaa gcaagtatga ctttaattcc actccatggc tcaatcattc acatgaggtg    3120
agcttcagcc tgagatagca ggcgacagac ttcttgcgtt tcaaaactgc catgccccc     3180 tgtgatgctc ccgtgaagga atgcactttg ccttgtaagt tcctgggaaa ggggtatgtt    3240
ttctctccag gtgcagccag atctcacaaa gtacaaaacg aatgcctttc ttttcttgtt    3300
tataatggtc actcactgtg tttggttact gtcaagaaat caataaatgt gtttaacaag    3360
```

```
ttacccagta aaaaaaaaaa aaaaaa                                          3386
```

<210> SEQ ID NO 8
<211> LENGTH: 328
<212> TYPE: PRT
<213> ORGANISM: Homo sapiens
<300> PUBLICATION INFORMATION:
<308> DATABASE ACCESSION NUMBER: NCBI / NP_001076002.1
<309> DATABASE ENTRY DATE: 2017-06-25
<313> RELEVANT RESIDUES IN SEQ ID NO: (1)..(328)

<400> SEQUENCE: 8

```
Met Glu Ile Val Trp Glu Val Leu Phe Leu Leu Gln Ala Asn Phe Ile
1               5                   10                  15

Val Cys Ile Ser Ala Gln Gln Asn Ser Pro Lys Ile His Glu Gly Trp
            20                  25                  30

Trp Ala Tyr Lys Glu Val Gln Gly Ser Phe Val Pro Val Pro Ser
        35                  40                  45

Phe Trp Gly Leu Val Asn Ser Ala Trp Asn Leu Cys Ser Val Gly Lys
    50                  55                  60

Arg Gln Ser Pro Val Asn Ile Glu Thr Ser His Met Ile Phe Asp Pro
65                  70                  75                  80

Phe Leu Thr Pro Leu Arg Ile Asn Thr Gly Gly Arg Lys Val Ser Gly
                85                  90                  95

Thr Met Tyr Asn Thr Gly Arg His Val Ser Leu Arg Leu Asp Lys Glu
            100                 105                 110

His Leu Val Asn Ile Ser Gly Gly Pro Met Thr Tyr Ser His Arg Leu
        115                 120                 125

Glu Glu Ile Arg Leu His Phe Gly Ser Glu Asp Ser Gln Gly Ser Glu
    130                 135                 140

His Leu Leu Asn Gly Gln Ala Phe Ser Gly Glu Val Gln Leu Ile His
145                 150                 155                 160

Tyr Asn His Glu Leu Tyr Thr Asn Val Thr Glu Ala Ala Lys Ser Pro
                165                 170                 175

Asn Gly Leu Val Val Val Ser Ile Phe Ile Lys Val Ser Asp Ser Ser
            180                 185                 190

Asn Pro Phe Leu Asn Arg Met Leu Asn Arg Asp Thr Ile Thr Arg Ile
        195                 200                 205

Thr Tyr Lys Asn Asp Ala Tyr Leu Leu Gln Gly Leu Asn Ile Glu Glu
    210                 215                 220

Leu Tyr Pro Glu Thr Ser Ser Phe Ile Thr Tyr Asp Gly Ser Met Thr
225                 230                 235                 240

Ile Pro Pro Cys Tyr Glu Thr Ala Ser Trp Ile Ile Met Asn Lys Pro
                245                 250                 255

Val Tyr Ile Thr Arg Met Gln Met His Ser Leu Arg Leu Leu Ser Gln
            260                 265                 270

Asn Gln Pro Ser Gln Ile Phe Leu Ser Met Ser Asp Asn Phe Arg Pro
        275                 280                 285

Val Gln Pro Leu Asn Asn Arg Cys Ile Arg Thr Asn Ile Asn Phe Ser
    290                 295                 300

Leu Gln Gly Lys Asp Cys Pro Asn Asn Arg Ala Gln Lys Leu Gln Tyr
305                 310                 315                 320

Arg Val Asn Glu Trp Leu Leu Lys
                325
```

<210> SEQ ID NO 9

```
<211> LENGTH: 328
<212> TYPE: PRT
<213> ORGANISM: Homo sapiens
<300> PUBLICATION INFORMATION:
<308> DATABASE ACCESSION NUMBER: UniProt / Q9NS85.1
<309> DATABASE ENTRY DATE: 2017-06-07
<313> RELEVANT RESIDUES IN SEQ ID NO: (1)..(328)

<400> SEQUENCE: 9
```

| | | | | | | | | | | | | | | | |
|---|---|---|---|---|---|---|---|---|---|---|---|---|---|---|---|
| Met | Glu | Ile | Val | Trp | Glu | Val | Leu | Phe | Leu | Leu | Gln | Ala | Asn | Phe | Ile |
| 1 | | | | 5 | | | | | 10 | | | | | 15 | |
| Val | Cys | Ile | Ser | Ala | Gln | Gln | Asn | Ser | Pro | Lys | Ile | His | Glu | Gly | Trp |
| | | | 20 | | | | | 25 | | | | | 30 | | |
| Trp | Ala | Tyr | Lys | Glu | Val | Val | Gln | Gly | Ser | Phe | Val | Pro | Val | Pro | Ser |
| | | | 35 | | | | 40 | | | | | 45 | | | |
| Phe | Trp | Gly | Leu | Val | Asn | Ser | Ala | Trp | Asn | Leu | Cys | Ser | Val | Gly | Lys |
| | 50 | | | | | 55 | | | | | 60 | | | | |
| Arg | Gln | Ser | Pro | Val | Asn | Ile | Glu | Thr | Ser | His | Met | Ile | Phe | Asp | Pro |
| 65 | | | | 70 | | | | | 75 | | | | | 80 | |
| Phe | Leu | Thr | Pro | Leu | Arg | Ile | Asn | Thr | Gly | Gly | Arg | Lys | Val | Ser | Gly |
| | | | | 85 | | | | | 90 | | | | | 95 | |
| Thr | Met | Tyr | Asn | Thr | Gly | Arg | His | Val | Ser | Leu | Arg | Leu | Asp | Lys | Glu |
| | | | 100 | | | | | 105 | | | | | 110 | | |
| His | Leu | Val | Asn | Ile | Ser | Gly | Gly | Pro | Met | Thr | Tyr | Ser | His | Arg | Leu |
| | | | 115 | | | | | 120 | | | | | 125 | | |
| Glu | Glu | Ile | Arg | Leu | His | Phe | Gly | Ser | Glu | Asp | Ser | Gln | Gly | Ser | Glu |
| | 130 | | | | | 135 | | | | | 140 | | | | |
| His | Leu | Leu | Asn | Gly | Gln | Ala | Phe | Ser | Gly | Glu | Val | Gln | Leu | Ile | His |
| 145 | | | | | 150 | | | | | 155 | | | | | 160 |
| Tyr | Asn | His | Glu | Leu | Tyr | Thr | Asn | Val | Thr | Glu | Ala | Ala | Lys | Ser | Pro |
| | | | | 165 | | | | | 170 | | | | | 175 | |
| Asn | Gly | Leu | Val | Val | Ser | Ile | Phe | Ile | Lys | Val | Ser | Asp | Ser | Ser | |
| | | | 180 | | | | | 185 | | | | | 190 | | |
| Asn | Pro | Phe | Leu | Asn | Arg | Met | Leu | Asn | Arg | Asp | Thr | Ile | Thr | Arg | Ile |
| | | | 195 | | | | | 200 | | | | | 205 | | |
| Thr | Tyr | Lys | Asn | Asp | Ala | Tyr | Leu | Leu | Gln | Gly | Leu | Asn | Ile | Glu | Glu |
| | 210 | | | | | 215 | | | | | 220 | | | | |
| Leu | Tyr | Pro | Glu | Thr | Ser | Ser | Phe | Ile | Thr | Tyr | Asp | Gly | Ser | Met | Thr |
| 225 | | | | | 230 | | | | | 235 | | | | | 240 |
| Ile | Pro | Pro | Cys | Tyr | Glu | Thr | Ala | Ser | Trp | Ile | Ile | Met | Asn | Lys | Pro |
| | | | | 245 | | | | | 250 | | | | | 255 | |
| Val | Tyr | Ile | Thr | Arg | Met | Gln | Met | His | Ser | Leu | Arg | Leu | Leu | Ser | Gln |
| | | | 260 | | | | | 265 | | | | | 270 | | |
| Asn | Gln | Pro | Ser | Gln | Ile | Phe | Leu | Ser | Met | Ser | Asp | Asn | Phe | Arg | Pro |
| | | | 275 | | | | | 280 | | | | | 285 | | |
| Val | Gln | Pro | Leu | Asn | Asn | Arg | Cys | Ile | Arg | Thr | Asn | Ile | Asn | Phe | Ser |
| | 290 | | | | | 295 | | | | | 300 | | | | |
| Leu | Gln | Gly | Lys | Asp | Cys | Pro | Asn | Asn | Arg | Ala | Gln | Lys | Leu | Gln | Tyr |
| 305 | | | | | 310 | | | | | 315 | | | | | 320 |
| Arg | Val | Asn | Glu | Trp | Leu | Leu | Lys | | | | | | | | |
| | | | | 325 | | | | | | | | | | | |

```
<210> SEQ ID NO 10
<211> LENGTH: 1870
<212> TYPE: DNA
<213> ORGANISM: Homo sapiens
<300> PUBLICATION INFORMATION:
```

<308> DATABASE ACCESSION NUMBER: NCBI / NM_001217.4
<309> DATABASE ENTRY DATE: 2017-06-10
<313> RELEVANT RESIDUES IN SEQ ID NO: (1)..(1870)

<400> SEQUENCE: 10

| | | | | | |
|---|---|---|---|---|---|
| atcccacccc | aagccaaccc | gaggagtgtt | tgccgctatg | agatcacctg | ctcccccagc | 60 |
| ccaacaacaa | aattaaataa | caccacggga | gaggagagag | ggaggggag | gagggaggaa | 120 |
| gggacaagag | agaagagaga | ctgaaacagg | gagaagaggc | aggagaggag | gaggtgggga | 180 |
| gagcacgaag | ctggaggccg | acactgaggg | agggcgggag | gaggtgaaga | aggagagagg | 240 |
| ggagaagagg | caggagctgg | aaaggagaga | gggaggagga | ggaggagatg | cgggatggag | 300 |
| acctggagtt | aggtggcttg | ggagagctta | atgaaaagag | aacggagagg | aggtgtgggt | 360 |
| taggaaccaa | gaggtagccc | tgggggcagc | agaaggctga | gaggagtagg | aagatcagga | 420 |
| gctagaggga | gactggaggg | ttccgggaaa | agagcagagg | aaagaggaaa | gacacagaga | 480 |
| gacgggagag | agaagaagag | tgggtttgaa | gggcggatct | cagtccctgg | ctgctttggc | 540 |
| atttggggaa | ctgggactcc | ctgtggggag | gagaggaaag | ctggaagtcc | tggagggaca | 600 |
| gggtcccaga | aggaggggac | agaggagctg | agagagggg | gcagggcgtt | gggcaggggt | 660 |
| ccctcggagg | cctcctgggg | atgggggctg | cagctcgtct | gagcgcccct | cgagcgctgg | 720 |
| tactctgggc | tgcactgggg | gcagcagctc | acatcggacc | agcacctgac | cccgaggact | 780 |
| ggtggagcta | caaggataat | ctccagggaa | acttcgtgcc | agggcctcct | ttctggggcc | 840 |
| tggtgaatgc | agcgtggagt | ctgtgtgctg | tggggaagcg | gcagagcccc | gtggatgtgg | 900 |
| agctgaagag | ggttctttat | gacccctttc | tgccccatt | aaggctcagc | actggaggag | 960 |
| agaagctccg | ggaaccttg | tacaacaccg | gccgacatgt | ctccttcctg | cctgcacccc | 1020 |
| gacctgtggt | caatgtgtct | ggaggtcccc | tcctttacag | ccaccgactc | agtgaactgc | 1080 |
| ggctgctgtt | tggagctcgc | gacggagccg | gctcggaaca | tcagatcaac | caccagggct | 1140 |
| tctctgctga | ggtgcagctc | attcacttca | accaggaact | ctacgggaat | tcagcgctg | 1200 |
| cctcccgcgg | ccccaatggc | ctggccattc | tcagcctctt | tgtcaacgtt | gccagtacct | 1260 |
| ctaacccatt | cctcagtcgc | ctccttaacc | gcgacaccat | cactcgcatc | tcctacaaga | 1320 |
| atgatgccta | ctttcttcaa | gacctgagcc | tggagctcct | gttccctgaa | tccttcggct | 1380 |
| tcatcaccta | tcagggctct | ctcagcaccc | cgccctgctc | cgagactgtc | acctggatcc | 1440 |
| tcattgaccg | ggccctcaat | atcacctccc | ttcagatgca | ctccctgaga | ctcctgagcc | 1500 |
| agaatcctcc | atctcagatc | ttccagagcc | tcagcggtaa | cagccggccc | ctgcagcct | 1560 |
| tggcccacag | ggcactgagg | ggcaacaggg | accccggca | cccgagagg | cgctgccgag | 1620 |
| gccccaacta | ccgcctgcat | gtggatggtg | tcccccatgg | tcgctgagac | tccccttcga | 1680 |
| ggattgcacc | cgcccgtcct | aagcctcccc | acaaggcgag | gggagttacc | cctaaaacaa | 1740 |
| agctattaaa | gggacagaat | acttcctgtt | ttctcagtgg | tctgattcta | ggcgcggtgg | 1800 |
| ggaaacattt | gggtattaaa | gaacagactt | cttccggaaa | ccaaaaaaaa | aaaaaaaaa | 1860 |
| aaaaaaaaa | | | | | | 1870 |

<210> SEQ ID NO 11
<211> LENGTH: 328
<212> TYPE: PRT
<213> ORGANISM: Homo sapiens
<300> PUBLICATION INFORMATION:
<308> DATABASE ACCESSION NUMBER: NCBI / NP_001208.2
<309> DATABASE ENTRY DATE: 2017-06-10
<313> RELEVANT RESIDUES IN SEQ ID NO: (1)..(328)

<400> SEQUENCE: 11

Met Gly Ala Ala Ala Arg Leu Ser Ala Pro Arg Ala Leu Val Leu Trp
1               5                   10                  15

Ala Ala Leu Gly Ala Ala His Ile Gly Pro Ala Pro Asp Pro Glu
            20                  25                  30

Asp Trp Trp Ser Tyr Lys Asp Asn Leu Gln Gly Asn Phe Val Pro Gly
                35                  40                  45

Pro Pro Phe Trp Gly Leu Val Asn Ala Ala Trp Ser Leu Cys Ala Val
        50                  55                  60

Gly Lys Arg Gln Ser Pro Val Asp Val Glu Leu Lys Arg Val Leu Tyr
65                  70                  75                  80

Asp Pro Phe Leu Pro Pro Leu Arg Leu Ser Thr Gly Gly Glu Lys Leu
                85                  90                  95

Arg Gly Thr Leu Tyr Asn Thr Gly Arg His Val Ser Phe Leu Pro Ala
            100                 105                 110

Pro Arg Pro Val Val Asn Val Ser Gly Gly Pro Leu Leu Tyr Ser His
        115                 120                 125

Arg Leu Ser Glu Leu Arg Leu Leu Phe Gly Ala Arg Asp Gly Ala Gly
    130                 135                 140

Ser Glu His Gln Ile Asn His Gln Gly Phe Ser Ala Glu Val Gln Leu
145                 150                 155                 160

Ile His Phe Asn Gln Glu Leu Tyr Gly Asn Phe Ser Ala Ala Ser Arg
                165                 170                 175

Gly Pro Asn Gly Leu Ala Ile Leu Ser Leu Phe Val Asn Val Ala Ser
            180                 185                 190

Thr Ser Asn Pro Phe Leu Ser Arg Leu Leu Asn Arg Asp Thr Ile Thr
        195                 200                 205

Arg Ile Ser Tyr Lys Asn Asp Ala Tyr Phe Leu Gln Asp Leu Ser Leu
    210                 215                 220

Glu Leu Leu Phe Pro Glu Ser Phe Gly Phe Ile Thr Tyr Gln Gly Ser
225                 230                 235                 240

Leu Ser Thr Pro Pro Cys Ser Glu Thr Val Thr Trp Ile Leu Ile Asp
                245                 250                 255

Arg Ala Leu Asn Ile Thr Ser Leu Gln Met His Ser Leu Arg Leu Leu
            260                 265                 270

Ser Gln Asn Pro Pro Ser Gln Ile Phe Gln Ser Leu Ser Gly Asn Ser
        275                 280                 285

Arg Pro Leu Gln Pro Leu Ala His Arg Ala Leu Arg Gly Asn Arg Asp
    290                 295                 300

Pro Arg His Pro Glu Arg Arg Cys Arg Gly Pro Asn Tyr Arg Leu His
305                 310                 315                 320

Val Asp Gly Val Pro His Gly Arg
                325

<210> SEQ ID NO 12
<211> LENGTH: 987
<212> TYPE: DNA
<213> ORGANISM: Homo sapiens
<220> FEATURE:
<221> NAME/KEY: exon
<222> LOCATION: (62)..(136)
<220> FEATURE:
<221> NAME/KEY: exon
<222> LOCATION: (280)..(465)
<220> FEATURE:
<221> NAME/KEY: exon

```
<222> LOCATION: (562)..(634)
<220> FEATURE:
<221> NAME/KEY: exon
<222> LOCATION: (790)..(964)

<400> SEQUENCE: 12
atggaaatag tctgggaggt gcttttctt cttcaagcca atttcatcgt ctgcatatca      60 g ctc aac aga att cac caa aaa tcc atg aag gct ggt ggg cat aca agg    109
  Leu Asn Arg Ile His Gln Lys Ser Met Lys Ala Gly Gly His Thr Arg
  1               5                  10                  15 agg tgg tcc agg gaa gct ttg ttc cag ttccttcttt ctggggattg            156
Arg Trp Ser Arg Glu Ala Leu Phe Gln
            20                  25 gtgaactcag cttggaatct ttgctctgtg gggaaacggc agtcgccagt caacatagag    216
accagtcaca tgatcttcga ccccttctg acacctcttc gcatcaacac ggggggcagg     276 aag gtc agt ggg acc atg tac aac act gga aga cac gta tcc ctt cgc     324
    Val Ser Gly Thr Met Tyr Asn Thr Gly Arg His Val Ser Leu Arg
                30                  35                  40 ctg gac aag gag cac ttg gtc aac ata tct gga ggg ccc atg aca tac     372
Leu Asp Lys Glu His Leu Val Asn Ile Ser Gly Gly Pro Met Thr Tyr
                45                  50                  55 agc cac cgg ctg gag gag atc cga cta cac ttt ggg agt gag gac agc     420
Ser His Arg Leu Glu Glu Ile Arg Leu His Phe Gly Ser Glu Asp Ser
                60                  65                  70 caa ggg tcg gag cac ctc ctc aat gga cag gcc ttc tct ggg gag         465
Gln Gly Ser Glu His Leu Leu Asn Gly Gln Ala Phe Ser Gly Glu
    75                  80                  85 gtgcagctca tccactataa ccatgagcta tatacgaatg tcacagaagc tgcaaagagt    525
ccaaatggat tggtggtagt ttctatattt ataaaa gtt tct gat tca tca aac     579
                                        Val Ser Asp Ser Ser Asn
                                                    90 cca ttt ctt aat cga atg ctc aac aga gat act atc aca aga ata aca    627
Pro Phe Leu Asn Arg Met Leu Asn Arg Asp Thr Ile Thr Arg Ile Thr
    95                  100                 105 tat aaa a atgatgcata tttactacag ggcttaata tagaggaact atatccagag    684
Tyr Lys
110 acctctagtt tcatcactta cgatgggtcg atgactatcc caccctgcta tgagacagca   744 agttggatca taatgaacaa acctgtctat ataaccagga tgcag at  gca ttc ctt   800
                                                    Asn Ala Phe Leu
                                                                115 gcg cct gct cag cca gaa cca gcc atc tca gat ctt tct gag cat gag    848
Ala Pro Ala Gln Pro Glu Pro Ala Ile Ser Asp Leu Ser Glu His Glu
                120                 125                 130 tga caa ctt cag gcc tgt cca gcc act caa caa ccg ctg cat ccg cac    896
    Gln Leu Gln Ala Cys Pro Ala Thr Gln Gln Pro Leu His Pro His
        135                 140                 145 caa tat caa ctt cag ttt aca ggg gaa gga ctg tcc aaa caa ccg agc    944
Gln Tyr Gln Leu Gln Phe Thr Gly Glu Gly Leu Ser Lys Gln Pro Ser
        150                 155                 160 cca gaa gct tca gta tag ag taaatgaatg gctcctcaag tag              987
Pro Glu Ala Ser Val
        165

<210> SEQ ID NO 13
<211> LENGTH: 1697
<212> TYPE: DNA
<213> ORGANISM: Homo sapiens
```

<400> SEQUENCE: 13

```
aacgcacgcc tgcttgcact cacactgcgg ttcacacccg gaggcgctct cgcactcaca      60
ctgccgctca cgcgtgctca cactccccca cgcgcgctcc gctccggctc cagcccgcg     120
cccagcgaag gcgcaggcac tgctgccgag agcgccgagg ggccccgcgg ccttcccatg     180
gcggacctga gcttcatcga agataccgtc gccttccccg agaaggaaga ggatgaggag     240
gaagaagagg agggtgtgga gtggggctac gaggaaggtg ttgagtgggg tctggtgttt     300
cctgatgcta atggggaata ccagtctcct attaacctaa actcaagaga ggctaggtat     360
gacccctcgc tgttggatgt ccgcctctcc ccaaattatg tggtgtgccg agactgtgaa     420
gtcaccaatg atggacatac cattcaggtt atcctgaagt caaaatcagt tctttcggga     480
ggaccattgc ctcaagggca tgaatttgaa ctgtacgaag tgagatttca ctggggaaga     540
gaaaaccagc gtggttctga gcacacggtt aatttcaaag cttttcccat ggaggtaaga     600
ataacaaatc atcttgtaaa aatcttgttt tctgaataaa gtattcagcg atttactgaa     660
aatgatttag ttaaaagta gatgcatagc tcttgaattt tatcagttta tactaaaatt     720
taaaaatgc ttaatgcaat ggaagcctag ggcagcacat gaaacctcct gtctactctc     780
gtggcttggc gtgtgcgcat gagcacatgg ccagaaaggc aatctacagt attaaatttc     840
accctagtgt tactattctt gtaaaaattc tgcctctgca aattcagtag gtcattttg     900
tggatgcttt ggataggtga cgagctgaag acaagcaacc gttggagaaa cctcaacagt     960
aatgaaaagt gtaggtttgc tagtttaaaa ttggtgggtt ggttttattc accccaagcc    1020
acttggggag ggagggagaa agagagattt tttgagagtg attcttttgt ccaaagaatt    1080
ccctccccga cttacgttct tagttaactt ctgctgtttc tttgatacgc agttgaaatc    1140
ttatgtcttc tgtgggactt ttctctagtt ttttccctag gcagaattca tctctctctc    1200
tctgctccct gtatgcttga tagggcactg ccatggcgct ggccccatgg gttgtaccat    1260
ttagtctcca cagcgtcttt cttgctgcct gtgagctcct gaggaccgaa gctccctctc    1320
accccttttt tactcccatc atttgcccac tgccaggcac agtggagata gacagttcac    1380
actggtgaaa gtgagggat gttggattca gtccacgtct tgatgttatt ctagaagga     1440
acctcagttt accccagaaa atagccttt ggtgtcatgt aagagtatgt tctggggct     1500
gctggtcttc cagtcttttt tttgacatt cacaactgtg catgtgctta atattaaata     1560
taaaattgct catgaccaga tgcaatatcc agtaccactt cagtggctgg aaatcatggc    1620
tgtataattc tatgtcagtg atacatgtat tttagagtat tctgttgaag tgtttgacag    1680
cattactgta attataa                                                   1697
```

<210> SEQ ID NO 14
<211> LENGTH: 617
<212> TYPE: DNA
<213> ORGANISM: Mus musculus

<400> SEQUENCE: 14

```
aaaaaagaaa cttaaattga atgaggatga agaagcagac ctttagtgtg accctgtta      60
acttctctgt ctgcagaaca catccagtca cctgcttcac tagggacatc acattacctt    120
gggaagccaa agtatacttc ttgttgcccc tgtttaagcc aaccccagcc catactatac    180
ttgtggaggg acagtgctga cactgacagc ccagtgtaca gcccacagct gtcaggctgc    240
atctttgctt cacagatcct gtaggccctt cccttcccca acatttttt ttttggggca    300
agatgtgacc aagccaccta tttggatggg tgggctggcc tccctctcct gacatctgcc    360
```

```
agtagactcc cctcccttc ctcccgccct gaaacctgat ccagctgaaa agctgcttgc    420
tagaaaactt ggcggctccc caactctggt ggccgggaag tgccaggctg cagcctcaca    480
aggtgcaggc gtgcagttgg aaaagcagtc tgcctgggac atgaggttgg cagcgggtgg    540
cgtgcaggct ggcagtctgg gggactcatc ctgagtggct gctctgaggc cctcccacat    600
ctgggaagct tgccatg                                                   617
```

```
<210> SEQ ID NO 15
<211> LENGTH: 611
<212> TYPE: DNA
<213> ORGANISM: Homo sapiens
<220> FEATURE:
<221> NAME/KEY: misc_feature
<222> LOCATION: (104)..(104)
<223> OTHER INFORMATION: n is a, c, g, or t
<220> FEATURE:
<221> NAME/KEY: misc_feature
<222> LOCATION: (352)..(352)
<223> OTHER INFORMATION: n is a, c, g, or t
<220> FEATURE:
<221> NAME/KEY: misc_feature
<222> LOCATION: (356)..(356)
<223> OTHER INFORMATION: n is a, c, g, or t
<220> FEATURE:
<221> NAME/KEY: misc_feature
<222> LOCATION: (370)..(370)
<223> OTHER INFORMATION: n is a, c, g, or t
<220> FEATURE:
<221> NAME/KEY: misc_feature
<222> LOCATION: (375)..(375)
<223> OTHER INFORMATION: n is a, c, g, or t

<400> SEQUENCE: 15
gatgaggaca aaagggcaga cctgtggaga ctccagttac ccttcccgta actacagagg    60
tgcccagtca cctgcttggt tatgtcaccc tggggagtaa gagnatggtc ttcctgctcc    120
tgcctgactc accctatcct gccccagccc agtgccacag aaacatactt gccaagggac    180
atcaatgaaa gcagcagcgt ggtgcacctc ccaggggtca ggctgcaccc ttgtctcatg    240
ggcttctgca gccctgtcc ccacctaagt tactccttgg ggaaacatgg ccaagccccc    300
tggctgaatg ggtggactga gctcccacag catgacatca gctagggcgg gnctcncctc    360
tcagctgtcn cctcnccttt cctcccgcct gaaacatgat ccagctgaag gactgattgc    420
aggaaaactt ggcagctccc caaccttggt ggcccaggga gtgtgaggct gcagcctcag    480
aaggtgtgag cagtggccac gagaggcagg ctggctggga catgaggttg cagagggca    540 ggcaagctgg cccttggtgg gcctcgccct gagcactcgg aggcactcct atgcttggaa    600
agctcgctat g                                                        611
```

```
<210> SEQ ID NO 16
<211> LENGTH: 1345
<212> TYPE: DNA
<213> ORGANISM: Homo sapiens

<400> SEQUENCE: 16
tcccgggagc ggtcgtttgg gagtgctccg tgggttaagc aaacgcaagc tgtaagtgat    60
gactgtggtc gagggcttcc ttgactgaga agaaactctg tccctcctag caatggtcct    120
ttgccccggg cctgctggga tgagttcagt gctctccaag ctggtcagga tcccagtcaa    180
taggacccag gctcttgctg gtgtagtaaa gacgcacacg ggtctgcgtt tgaatctcag    240
ttcctccact tgcagagcaa ggtgctcacc tttctggtgc ttggggatcc ttgtgtgcaa    300
```

| | |
|---|---|
| atagccactc tggtggactg ttctaaagtt aaatgaagaa tatgtttatt gatgttattc | 360 |
| caaaggagac acttaaaaaa tagtttgtgt gtgtgtgtgt gtgtgtgtgt gtgtgtgtgt | 420 |
| gtgtgtgttc tctctgctct tctctgtcct tctgagggaa gccagtagct tatcagggaa | 480 |
| aaggggggtga aaggaggggg aatctgcagg agtgatttgt tgtacaggtt gcacactaga | 540 |
| tgagagaaga cacagtcttg tttagcaaaa gccaggcctt gccagcacct ggttagtgaa | 600 |
| agaccctggc tacctgccag ctccatctcc cctttgctgc ccgtatgctg gccctctagg | 660 |
| ttgtactccc ttcaccgtcc catgaatttt cacttttgca tgtcaggcca cccttctgga | 720 |
| agtgctcctg ctgcttccag tgtgaaaact gagctgtgca tgaaatcttc atagaacagc | 780 |
| accagggtcc aggagctggg ctgtctcatt actggtttgt ccccataggc cacctacccc | 840 |
| ggaagtcgtt tgatttcttc tcactccctc cacacctcgc cccaaccacc tatctaagcc | 900 |
| catcatgttt gcccatacag caaccctagg aggtggactg ggccagccct ccacccatag | 960 |
| cttgtgtgtg cctggggcag ggtgcgagga tcctcttggg gtggcttttg caggatgtag | 1020 |
| aggaaatgtc agttttcacc agatgcccac acttccttct ttctttacct gtttcatact | 1080 |
| caaaaaggag atgttgtgtg cagatgctga ggtttgacct tggctgagga aaaccctgat | 1140 |
| gcagacccctt gggcttagaa attgtgcact tggggtcatg ctttcttgca accctcttgc | 1200 |
| ttttagtatc ataccctgag agccagcttc cttgttgctc cccagaggcc ctcgcttagg | 1260 |
| ccccgtgggc cacctgctcc gaccttctta gccctcaacc tgatttgaat ctcagctgtc | 1320 |
| ttgtgccact tgctcttcca agcca | 1345 |

<210> SEQ ID NO 17
<211> LENGTH: 1212
<212> TYPE: DNA
<213> ORGANISM: Homo sapiens

<400> SEQUENCE: 17

| | |
|---|---|
| ttttgatttt aattagaaga aagactgcca ttagaattgt tttctaatga aatctttata | 60 |
| aattctctgg gcagtgcctg tatctttatt agaaagactt cttatttta acaatttat | 120 |
| ttggaagaag ttctactcat ttgcatcagt tcatcgtcta cataatttgt gtgtgtgtgt | 180 |
| gtgtatgtgt gtgttacaac tttgactttt gaaactagaa tagaatcagg taaaacatct | 240 |
| aagatcagtg tgccagtaat tggcctgaat catcgggcac catgatgggt ttggccgcct | 300 |
| tcaacggtac tcgtgtacat tctatttttt tcttcataat gttcagtact gtagtactaa | 360 |
| tcaccgagaa aattgcattg actcttttcg accaccaggg aaatattcag ctcatggttc | 420 |
| tccccaaaaa aactaaaaag cagctaagcg ctgggaacaa atctgactta ttgcattttc | 480 |
| tcagtgggcc aaagaaagga gggccgattg actgctttga ctttttaaag gtcttctctt | 540 |
| tgttcactta taaagtgagg aaaacaaatt ctcggcactg gcgtgagagt tgagcgtcac | 600 |
| aaaagaaagc aaaagaaaat attagtgcca ttattgtggc gaatttcatg tttcccagcg | 660 |
| agccctttga ttcctggttt gggctggcgc tcgagctctc cagccgggta tgacttcggc | 720 |
| cacaagatgg cactgaccctg caaacaaaga aaagcacagt ggcaccgact ttttcaagcc | 780 |
| tcgggaaact gccctgcctt ccccggagtc gaggactgtg gggattaggg cttccttttcc | 840 |
| cctgcgcggg aggtctgtgt cgaataatgt gtggcttctg ttggattgct tttctttcca | 900 |
| aaattcctag gcaatgcttc cccgaggtgt gcacctttgt gaggtgtttg tggggttggg | 960 |
| ggagcttcag gcgctactcg cgggacgacg tcacgtgatc cgggatgagg tggagttcgg | 1020 |
| cttttaaggag gcgtctcttc ctagcttcat caatctttag gatctgagca ggagaaatac | 1080 |

```
cagcggatct tccccactct gctcccttcc attcccaccc ttccttcttt aataagcagg    1140
agcgaaaaag acaaattcca aagagggtaa gttgcgagtt tatgcctttc cagagacttc    1200
tgcgaaatct ct                                                        1212
```

<210> SEQ ID NO 18
<211> LENGTH: 1148
<212> TYPE: DNA
<213> ORGANISM: Homo sapiens

<400> SEQUENCE: 18

```
gagcaaaagt gtgaaaataa agtctttatt aaactatggc aacttataaa aaataatatc     60 ttttaaagg tttactggga attttcttat aaactcttct atatctgaca cctagacaaa     120
tgaaaccttc tgaatagatt ttaagtattt taagaaagta gatagttctc aagaataata    180
ggaggaactg cagggaattc aaaggatatt aaagtctga cttgtacatt taaataaggt    240
ttctttgttt gaataatttt ttgctttatg aaaatacaca tcattctttt cacaaaggat    300
gacaatcaca caaaagaata aaatatatgt aattcttttt cctcctgcaa tgatacaata    360
tcaactattg tctgttttgc tgtgatcgtg gaacagcagc atgattccat gttctcaaat    420
attcccatgg ttttttctta aagccagaat ctggcacaat ttgaattgga agataaata    480 cagctctgct cagctgacaa acacacaggc atgcaccacc ctcccttcca aattctaaca    540
gcagagtttc tcttcccttg agaaatctga atctaaaaa ttgcattcgg actgccaaaa    600
attctgctga aaagagcctt aggctatttt ccatggtgta aggtaaaatc gttttggctt    660
tggtccaaca caacgcctca gttcctttaa aagattaact aaaggtctgt gaacttggaa    720
aaaagaattc cttggaattc gagttctatg gatgtttgtt attgctcgca tttgttatat    780
gaagacacct cgcaaacagg agcgcaaacc ttagagcgca gctgcctccc gggctcgggt    840
cagcgctgga ccgcgcggca gctggacggc ctgagtggcg ccccgcgggc tgcgcccccg    900
gcctcgccag agaccgcta ggttgagccc tgacccgggc accccgcggg ctgctgttcc    960
cagctccgga tgccagccgg gctagcgcca gagcgtgtcc agccggggc agcgcttgtt   1020 ccatcccccg cccatcccc aggaggctcc ttcgcggatc cccgacactc tcctcccggg   1080
ttcggcccgc gcctgctcca cccgggtgag ttgggaaccg gagggacctg ctcggcacga   1140
aagaattc                                                            1148
```

<210> SEQ ID NO 19
<211> LENGTH: 1308
<212> TYPE: DNA
<213> ORGANISM: Homo sapiens

<400> SEQUENCE: 19

```
aaatattctt taaaattatt taataatgga aatacagata ccatttagac ttcacatttt     60
agaatagttt tgatgtatat gaaaacaact tttattggta gtgtttaatg ttgtataatg    120
agtctggaaa ggatttaaaa ttcttttattt ggtaaattac ttgtgtatta ctaggacagt    180
ggagttaaat tgacaatttg accaattctc aataggcaat agcatttcc tacaggactt    240 ccaaaactgt agttaatgtt gaagattata atcataattt gggcatacat ctgtcattta    300
gttgtgattt tccaggcata ttaaatttt tctgtacttc acaaactaaa cattaagaag    360
cctatggagt agaaatgata tagatagctg gtagatattc ttcaagtttg aaattaaaag    420
ttcctcgaga aaaattttttt cttattatat ttttggacaa agtactgag ttggttagat    480
```

| | |
|---|---|
| ataactttta ctttcaacaa aaaatacaat tcatttgttt ataagacaac atggaagtgg | 540 |
| aaggtaatac aaccttctaa agtgaaatta cagattggat tgacactgac tgcacaacta | 600 |
| aataaattaa tcctactata acacataaaa ttatcttcca tatattatga actgacattt | 660 |
| gaatccagaa ctcttcaca taaattaaat tccatgttaa caaaatttct atttattata | 720 |
| tgtaaatagt tatcataaat atattttata tgaccccagc atttgttctt tccttggtaa | 780 |
| acagtgagaa ttattacata tgaagacagt gtataaggga cactaaatca gcttaatcc | 840 |
| cattattaag aaacccatat agaattggat taagacaaca ggacatcatg cccacaatga | 900 |
| caatgcaata caccaacttg aaatgcctat ttgaaataag attgtcatta aaatcactta | 960 |
| ccacatggaa aaggtgtagt ggcatccaac taacagcaaa tactaatatc agtatggtca | 1020 |
| gtctgtagaa aacacttcga gatctctttt ttattcttgt aacagaacgt tttactctca | 1080 |
| attcatgaac atctgaattt tcttcaggtt ttatctcaaa gcaagtgggg acccctggta | 1140 |
| tgaacttact ggatgaagag agctgacttc ttacagagcc aaagttttct ggaagtattc | 1200 |
| tggagtggtt ctcttgagaa ggtctttctg gagcaggtaa cacacatgct gtcttcttgc | 1260 |
| tatatcttct tctgtgtttt ttgatgaatg aataactcca tttatggc | 1308 |

<210> SEQ ID NO 20
<211> LENGTH: 731
<212> TYPE: DNA
<213> ORGANISM: Mus musculus

<400> SEQUENCE: 20

| | |
|---|---|
| cggagaacat ttttgtttca gcatttcatc tgaagccacg gtttcacatc atcaagtctg | 60 |
| caaaaaccg ttcacaaacc acccaaaac ttctcggtaa agaactccta aggccaaaga | 120 |
| gggagactgg gtagattgtt tttaatttgt ttctttttgt caaggggga caaaacacgc | 180 |
| tttggtgagt gcgagtgttt attctgggac acaaacccag agtctggaag ggagcattca | 240 |
| acgggtgctg ctctgccacg caggggcagc ggtgggactc agcccatcct gctaaggacg | 300 |
| ggcagcctga gccaggcttg ggagtctgtc atggctgcca gacgaatcat tatctaattg | 360 |
| cagcctttc tcttccttag gtttcagcag gtcccgagag agcatttaaa atcactttta | 420 |
| ctactttacc atctaatcac acataagcct ctccctatac cctccaccct ccttccattc | 480 |
| agagtgtact ttctggagca ccatccagca agcagggtgg aactcgtgac gggaaatggg | 540 |
| aacggcaccc acgaaggcgt gattccttgt agatccttga gtgacggacg ggtgaggttt | 600 |
| ccgtcaggca agcccagcca ccttcgtgga ggagccccgg acaagtgtaa gtttcgcaga | 660 |
| gctggggtct ccagcttact tctgctaatg ctaccccagg cctttagacg agaacagat | 720 |
| ggcagatgga g | 731 |

<210> SEQ ID NO 21
<211> LENGTH: 820
<212> TYPE: DNA
<213> ORGANISM: Rattus rattus

<400> SEQUENCE: 21

| | |
|---|---|
| ttgagaacat ttttgtctca gcatttcatc tgaagctatg gttttacatc accaagtctg | 60 |
| caaaaaacag ttcgcaaacg gaaccaaaac tttttcgaca aagaactttt aaggcgaaaa | 120 |
| cgggagatag agtagattgt ttttaatttg tttctttctg gcaaggggg acaaaacaca | 180 |
| cttttgacgag tgtgagtgtt tattctggga caaacccaga gtatgaaagg gagcattcgg | 240 |
| tgggtgccgc tctgccatgc aggggcgcgg tggggctcag cccatcctgc tcaggaccca | 300 |

```
gcctggcccc aggcttggga gtctgtcatg gctgccagag gaatcattat ctaattgcag      360 cctttctct  tccttaggtt tcagcgcgtc ccaggagagc atttaaaatc acatttacta      420
ctttaccatc taatcacaca taagcctctc cccatacccct ccaccctcct tccattcaga     480
gtgtactttc tggagcgcca tccagcaagc tgggtgaat  tcgtgacggg aaatggaaac      540
ggtacccacg aaggcgtgat tcctcgtagc tccctgagtg aggttcccat caggcaagcc      600
cggccacctt cgtggagaag cgcggacaag tgtaagtttt gcagagctgg ggtctctagc      660
ttgcttctgc taatgctacc ccaggccttt agacagagaa cagatggcag atggagtttc      720
ttattgccat gcgcaaacgc tgagcccacc tcatgatccc ggaccccatg gttttcagta      780
gacaacctgg gctaagaaga gatctccgac cttatagagc                            820

<210> SEQ ID NO 22
<211> LENGTH: 834
<212> TYPE: DNA
<213> ORGANISM: Homo sapiens

<400> SEQUENCE: 22 ttttttttt  ttttgtaatt tcatttcaaa ctattatttt ataagacctg gcctattact       60
gagtatgcag gcagaatatg aaaattactc caaaactttt ttaaatgaaa ttttcaagat      120
gcaaaaagtg aaactttaaa atttcagtgg aagaagggga acaaaaacat tttaataaat      180
gagagtgttt attccagaat gggaatatag agacaaggaa ggtaccatgt gaatgggtgc      240
acctcgctct ctggggtcaa tgataggaaa cagcctgtcc cacagtcaag gcagccttgc      300
ccaggctatg agtctattgt ggatgctggg gcattgttat ctaagtgcag cctctttgct      360
tcctcaggtt tcagcatttc ccatgagatc atttaaaatc acatttgcta ttttaccatc      420
taatcacaca taagcctctc cccacactcc ccccgccctg tttccatcca aggagtgcac      480
tttctggagc accagcaacc agggtggaac tcgtgacggg aaatgggaat ggcacccaag      540
aaagcatgat ttctgtagtt tcgtgaatga tagcaaggct cccatcagac aagctgagcc      600
actgtcactg aggaggacaa acgagtgcaa gtctttgcaa agcttggcat ctcagacttg      660
cctctcattt cttgcttcac acactagcct cttggctaga aacagacat  cagatggagt      720 ttcttctggc tatgcctgaa tgttaagctg aacgtatgtt ccaggagctc gtggtctcca      780
gtagaggcaa tctgggatag aagagaagat atttcttacg tagaagacaa gcaa           834

<210> SEQ ID NO 23
<211> LENGTH: 1452
<212> TYPE: DNA
<213> ORGANISM: Homo sapiens

<400> SEQUENCE: 23
gctgaggtgg gagaattgct tgagcccagg agacagaggt tgcagtgagc agagattgca       60
ccactgcact ctagtccggg tgacagtgat accctgtctc aaaaaaaaaa aaagaaaaag      120
aaaaagaaaa aaacaaaaaa gacaagaact gagaagggcc ccctgacttt agccacaagg      180
caatctcttg tatccctgca aggaagcatt ttagtgagat aggagggcaa aatccaagct      240
tcaaagactg aaaagtgact ggaaacagtg agtagaagta agtcctttat taaaagccaa      300
tagagaacag gagagaggag ggaagacctg gatgggctct gcatcaaggg aaagttttta      360
aagttggagg aaagttaagc atctttaaat gctgatagga aagagctggc agacaaggag      420
agagaaaaaa atgaggtaga tatgagataa gatcctaagc agagggaaag gaatggtcct      480
```

```
tagaatgtag gaagatacct ctcatgttgt aagagaaggg aaggaggaaa gaaggctgca      540
gacacaggtg agttggaggt ttgatggtat gaagttggca gagttctgtt tttctccatg      600
aactaggaaa tatggtcatt ggcttactgc aagggaagac agggaatagt gagaaaagag      660
tgtatttgaa acctcagact agaagaaact gctgactagg gataccatat gattcccagg      720
caatactgag gttccccata acccctcagc agttcagggg aactgttcta gattgactta      780
gccttgggat ttaggataag ggtgagggag tggcaaaatt gtggaccaca ggtctaatct      840
ggttatgggg aaaagtgttc agccacagac tgaacctgga ggtcccagag aaattggagg      900
tcccaatgaa attctccaat aatctggagt tctccagtaa cttggaggtc caaatgaaat      960
tcaaacaggt ggagaaatgt tgacaatgtc aataaataaa agattgtgat aagaaagtag     1020
catgagactt aagataaagt agactataaa ccaaagtctt tgatgaatat gggagagtgc     1080
ctggaactca gtggtcctgg aaatgaggag agagggcagc atggctaaat ctggtggtgg     1140
tggtaggatg gtacaaagtg gtgaagaagc aatgacatag aagcacatgg ggagcaaaga     1200
cataaccctg aggcacctgg aggagggttg aataaacagc ctcccctgaa tgccttgcag     1260
gggaatgggt tcctggggag agccaagtgt gagttcaggg aggggccaga tatgagggtg     1320
ggagaagggc tgttctgaca atcaagatgg gacagatgag agggacaggg ccagtgggca     1380
agctgtcacc tctctgtggt tatgtccact cttataagag tataaatact tcctgaagaa     1440
gaatgagaag at                                                          1452

<210> SEQ ID NO 24
<211> LENGTH: 1534
<212> TYPE: DNA
<213> ORGANISM: Homo sapiens

<400> SEQUENCE: 24
accaccaatc agggaagaga aggcgatttg tccaggatat ggcactgaga attatcacaa       60
gtgagctagt tcaccttcat tgcacagtct cagtcactga agtttccttc cttcaatagc      120
acatcttaca agtcaagaat gtaaggtcca agccccagg acaaatctca gaagcaaaga      180
aagcagcagg gaaagtagaa ccctgggatt tgatttcctt ccggttatct ctaagcatca      240
tttccatgat agaaggtgtg gaagcaaata ataaagtgc ccgtcactag tgtttatcct      300
gcaaagtggt ctgccctttt gagaggcacc ctgccctatg ccatcctttt gatttcttcc      360
cttggtggaa atttcctgtt tctctttgag aaagataatt caaccctgtt tccattgttc      420
ttcctcccag gctgctgtag gaaagcgcac gcacacactc cacacaaaat gaattttaa      480 aaaatttatt ttcacagtcg ctcctaccag ctctgaaatt cagaacccat atgactgatg      540
gcatattcag ataatcgggt cccaggtctg gaaaagcagc cttttcccca cgtttctttc      600
cccacctagg acctcctctg attcttcact gcatcttcga aagaaaatgt attatttgct      660
tgcctggaag acgctgcaat tcaattgatt ttatatatac atatatataa agaaaacaga      720
aaacatagcc tagataccgg tcttgagcgt caccgcccca ctcgcggttg tgagcaaagc      780
cctacggaag aaaccaattc ccagcctaga ctcttcagag cccaaggtcg gggaggcgct      840 ggcctggcg tgttgtctgg ctccccagcc actgccccag actcagggct ttgccattgg      900
tccccacctc ctctgctccg gagttttct ccagctcccc accaagccac acaaagtgac      960
ttctcggaaa cattagccga ttctgctgag caggaaggga ggaaagggat gatggggcg     1020 gggggtgagat aagggaaggg ctcttctggc tgctggacac acacacacac acactcaaac     1080
acacacacgc cccacccaat gggtggccgt ggatggcagg tcgtgcaacc ccctcctccg     1140
```

| | |
|---|---:|
| ccttctatta gcgcatggtg cagaggctac agcgtcgcca ccaccgcgcc cctagctggg | 1200 |
| tccccgccct gcgccgcccg caggagtgga gagaggagg gagggaggga gcaagggtg | 1260 |
| gggacccggg cgcgctggga ggagtggagg aggcaaagcg gcgcagctgc cctcggggag | 1320 |
| gcggggctgc tacctccacg ggcgcgccct ggcaggaggg gcgcagtctg cttgcaggcg | 1380 |
| gtcgccagcg ctccagcggc ggctgtcggc tttccaattc cgccagctcg gctgaggctg | 1440 |
| ggctagcctg ggtgccagtg gctgctagcg gcaggcgtcc cctgagcaac aggagcccag | 1500 |
| agaaaaagaa gcagccctga gagagcgccg ggga | 1534 |

<210> SEQ ID NO 25
<211> LENGTH: 138
<212> TYPE: DNA
<213> ORGANISM: Homo sapiens

<400> SEQUENCE: 25

| | |
|---|---:|
| cctaacaggg gaggggcag aggggggggc gtcagagagt aggaagcggg tggagaagag | 60 |
| gggcaaggcg gggccgggcg ggggccgctg gctccgccct ttcctggcgg ctgggtcttt | 120 |
| aacaccgccc agcgcaca | 138 |

<210> SEQ ID NO 26
<211> LENGTH: 1469
<212> TYPE: DNA
<213> ORGANISM: Homo sapiens

<400> SEQUENCE: 26

| | |
|---|---:|
| gacatctgcg gggtaacttc tggcagcctc gacccgggag aacgtggaca gcccttggcc | 60 |
| tctgggagcc cctctcagcc tcctaggagg cctccttgtc ctctttggag acccttagc | 120 |
| gccaggctcc gtcaccgcct agtccctggg ttctgaccaa gatcccgagg aagaaggcga | 180 |
| tcactgtgta gggctctgcc tccgtctggt caccttcttg agctcaggct gctcggtcgg | 240 |
| tctgtgtgtc cctgtctcgg ggacttgggg ggccatccgt gctggggcct tggcggagag | 300 |
| aaccgtgagc ctctaggagg tcgtccttcc cccgctccct ggggccttgc ctgtctcccc | 360 |
| gccaagagac accctcttc ccttcgctct ccccagcttg agacggatgg gttagtgcag | 420 |
| ccacggaggc ttgcgcggtg ggaggggttg ggaccagcct tctgctgccc tgggtgctgg | 480 |
| ggatcccggg gctttccagg tgctcggcct ccaaggtgcg cggtcctcag ctccacccgc | 540 |
| gggcggctcc tgcgtccgag gagctaagag aagatctatt aatttcttca cgaataaatc | 600 |
| gatgctcttg tcagggaggc gatcgatgtc agccctgccc tgccttgccc tatcctgccc | 660 |
| cggggccggc gctggctggc cggggtcagg gactgaagct gagacctgag gcgttgctca | 720 |
| ctggggctg cagatcgcac ccccaggcac ccagcgcggg cggggagctc gcgcctttgc | 780 |
| gcgcgggctt ctcgcgccac cctgtggctt ctcttggagg cgcggtcttg gctctccgga | 840 |
| ctcccttcgg ccggattagg cgaccccttc cctttctctg ccccgtctgt gtcttcctcc | 900 |
| ccaggttctg cgattgatcc tttggtagtc cttttcgttt tcttcctaga gttcggagaa | 960 |
| tgttctacct aacttactcc aagtgacatg ctcactcccc taggcacgcg cgccgcgagg | 1020 |
| atggagcgct gagcctgggg ctggctagga tgacctggac agcaaccttt cctcaacgca | 1080 |
| gtcatcttcc ctcctcccca aatgtaaaaa tgcagctgct ttaagctgag agaaataacg | 1140 |
| tatcagcttc ccacctccgg cctcagcaga cacctccgag gcgttctgct gcggcccctc | 1200 |
| agcgtctgcc ggagctgagg cggatcctcg gggagaaggc tgacgctggg ggcccctaac | 1260 |

| | | |
|---|---|---|
| aggggaggggg gcagagggggg gggcgtcaga gagtaggaag cgggtggaga agaggggcaa | 1320 |
| ggcggggccg ggcgggggcc gctggctccg cccttttcctg gcggctgggt ctttaacacc | 1380 |
| gcccagcgca catgtcgggg gaggcctggc agctgcagct gggagcgcac agacggctgc | 1440 |
| cccgcctgag cgaggcgggc gccgccgcg | 1469 |

<210> SEQ ID NO 27
<211> LENGTH: 1306
<212> TYPE: DNA
<213> ORGANISM: Homo sapiens

<400> SEQUENCE: 27

| | |
|---|---|
| tagatggcgc atgctctcca aacttggctt tgtccatcaa ggttcaagaa aacaatggtc | 60 |
| agacatgttc ctcttaacaa acagtatgtc cccaaacagc aaaaatgcat acagtccttt | 120 |
| ctgggtgaat ttttaaatct tacataaatc catcaacccc atcctttttc ctttgcctct | 180 |
| tgggagaaat taatctagct ttacattaat tatgcatgtt atcagatttc aagctccttg | 240 |
| agagcaggta ttttaattct ataaagcctc tacgtggcct tggacatggg aggtgcttaa | 300 |
| ttacccaaga tgctccttga atacagatgg tacacgacct acacagactt agatctttac | 360 |
| cacttccccc ctctccccac cctgacttgc tcaatcctga aggaactgga gacgtctaag | 420 |
| tgtctgaggt tcacgcttcc acacagaagc ttgggtctgt gtgggaggga aaaggaagc | 480 |
| catctgtccg caggccagac caggccacac cctgctagca cccagaaccc tttgtcccag | 540 |
| gcccagccct gccatttttac tttccttgca tctggaaagc acagggaata tagtagtgac | 600 |
| aaagaaggga agggttgttt gagtttaaga atagtttact ctaaaaaaaa aaaaaaaaaa | 660 |
| aaaaaaagga caaaagccaa agagaaggtc aaagttgact gtggagaagg ccttgcaagc | 720 |
| agggaacttg ggaagaattg gaatgagagt gagagaaggc aactgagttt ggaaatattt | 780 |
| tttctgacta gcttttcttt ccaaatgcca ctgaacttag attggtttag aagggttgt | 840 |
| agtacatcaa agtggctaga agcacaggtt tggggatcag ataaggattt cattctagag | 900 |
| tgtgatcttg tacaagttat tcagccttttg caaacctcag attcacacaa tgtaagatga | 960 |
| agaaactcac cttctgaaaa ttagagataa catatgcaaa gtgaatcaat acagggctta | 1020 |
| acatatttat cacccctttg gtaaataacc atgacgatta ccagagctct taagggcaat | 1080 |
| ggcaggtggg aagcagaact catggtggt aatccccagg ccagccaggc tcaccatgtg | 1140 |
| cacttggaca agtccttgcc cccatcattg tgaaatggtg cagggatgca ccatgagggt | 1200 |
| gtggcaggat ggctgacaac agactgggaa gcagctcggc agaaaaactg gattgatgcc | 1260 |
| cactatggca agagatatca tctcccctct tgttctgtga tgtttc | 1306 |

<210> SEQ ID NO 28
<211> LENGTH: 1554
<212> TYPE: DNA
<213> ORGANISM: Homo sapiens

<400> SEQUENCE: 28

| | |
|---|---|
| accgcccgag agactcggag gcaggcttgg gacacgtttg agtgaacacc tcaggatact | 60 |
| cttctggcca gtatctgttt tttagtgtct gtgattcaga gtgggcacat gttgggagac | 120 |
| agtaatgggt ttgggtgtgt gtaaatgagt gtgaccggaa gcgagtgtga gcttgatcta | 180 |
| ggcagggacc acacagcact gtcacacctg cctgctcttt agtagaggac tgaagtgcgg | 240 |
| gggtgggggt acgggccgg aatagaatgt ctctgggaca tcttggcaaa cagcagccgg | 300 |
| aagcaaaggg gcagctgtgc aaacggctca ggcaggtgat ggatggcagg gtaggaaggg | 360 |

```
ggaggtccag aggtctggat ggaggcttcc gcatctgtac cttgcaactc acccctcagg    420
cccagcaggt catcggcccc ctcctcacac atgtaatgga tctgaagagt accccgggac    480
agtccgggga gatggagatt cggaaagtat ccatggagat cttacagaat cccctgtgcg    540
gaccaggaaa ctcttgtaga tccctgccta tctgaggccc aggcgctggg ctgtttctca    600
caatattcct tcaagatgag attgtggtcc ccatttcaaa gatgagtaca ctgagcctct    660
gtgaagttac ttgcccatga tcacacaacc aggaattggg ccaactgtaa ttgaactcct    720
gtctaacaaa gttcttgctc ccagctccgt ctcttgtttc ccacgagccc tggccctctg    780
tgggtaatac cagctactgg agtcagattt cttgggccca gaacccaccc ttaggggcat    840
taacctttaa aatctcactt gggcaggggt ctgggatcag agttggaaga gtccctacaa    900
tcctggaccc tttccgccaa atcgtgaaac caggggtgga gtgggcgag ggttcaaaac    960 caggccggac tgagaggtga aattcaccat gacgtcaaac tgccctcaaa ttcccgctca   1020
cttaagggcg ttacttgttg gtgccccac catccccac catttccatc aatgacctca   1080
atgcaaatac aagtgggacg gtcctgctgg atcctccagg ttctggaagc atgagggtga   1140
cgcaacccag gggcaaagga cccctccgcc cattggttgc tgtgcactgg cggaactttc   1200
ccgacccaca gcggcgggaa taagagcagt cgctggcgct gggaggcatc agagacactg   1260
cccagcccaa gtgtcgccgc cgcttccaca gggctctggc tggacgccgc cgccgccgct   1320
gccaccgcct ctgatccaag ccacctcccg ccaggtgagc cccgagatcc tggctcaggt   1380
atatgtctct ccctccctct ccctccattc gtcattttct cactccctt cctcctctcc   1440 ctctctctcc gttagtctct tcatcagata gtctctgtta gtccgcgatt tataccaggc   1500
tcgtgcccta ggttggatcg gacagtctca atccccggc tcgctcttcc tgct   1554

<210> SEQ ID NO 29
<211> LENGTH: 1297
<212> TYPE: DNA
<213> ORGANISM: Homo sapiens

<400> SEQUENCE: 29
ggctggggaa aacagcattc actttgcaag cttcttggga tttttactta actagagtct     60
cttcttccca ggatttaaaa catgatggaa actttagctc atgaatcaaa caaccctcc    120 agagctaaaa gccagctgta tttgcataac aatttagcag atccaaacag cagggcaagg    180
tcgggtgaaa taagttgcca aggtcatggt catgaagtag tattagactc agaaaggctg    240
atccccagtg cttgctccac cccatggatc tctcctaccc tccttctaaa cgatactgtg    300
ggataaaata aaattaatct actgtatatg tgcaaaccac aggcctgccc ttaactcttt    360
ccttaccttc tagtttcaga ttattcaaat catggaggaa aagattagat cacaacacgt    420
tgacttcact gtattaccat acaaatgaaa taacttagta caaactgtga tctgggact    480 cttgatctaa actgggaact gctgttgact gcattttaaa ctctaaagt attttgaaac    540 tctttaattt cttgaactga aaaaattgct ttgaattcac tttgttttaa ttctgagaac    600
ctaaaaacag ggattcttta aaaaaaaat gcaaaggctc acatgccaga agaaagaag    660 ctgaggagat aaaaatgtgt aaataattct tactttaata cccttagcta gaaaaacctt    720
aaaagcgaca catccagaag ctcgttaagt cacagcctct tgaacctat ttcagtgaac    780 caccgaattt cagatccctc aggtgcgact ctgaattcag aattctcacc ggctcatagt    840 cctatttttcc ttcttaggtt ttagggaatt ttgcaaacta tgacgccag cctttgaggg    900
```

-continued

```
gagaggactt tccaggggcg cgggatgtgc cactcgggaa tctcaccaac agtgggcgtt    960
tagcgcagcc aagcgacagg caggcgccag ggctcagcaa cagggaggcg ccggctgagg   1020
cggggagaac tttggcgctc ggagcagagc caccctttgc tggccagtcg cgttgctcct   1080
ccgaggaagc aagcggcggt ggcgactcgg tggaaaaata acgaaagaaa ggcagagagg   1140
aagtagcgag agaagagaga aaatgaagtc ggcgctgggg gagcctgcag gagggtggcc   1200
aacagtggag gaaggtggat ttggcttctt ttccgcaccc cgggcgtgaa agccctctcc   1260
aacgcgaccc caggaaataa gtgggtctcg cctgggc                           1297
```

<210> SEQ ID NO 30
<211> LENGTH: 139
<212> TYPE: PRT
<213> ORGANISM: Homo sapiens

<400> SEQUENCE: 30

```
Met Ala Asp Leu Ser Phe Ile Glu Asp Thr Val Ala Phe Pro Glu Lys
1               5                   10                  15

Glu Glu Asp Glu Glu Glu Glu Glu Gly Val Glu Trp Gly Tyr Glu
            20                  25                  30

Glu Gly Val Glu Trp Gly Leu Val Phe Pro Asp Ala Asn Gly Glu Tyr
        35                  40                  45

Gln Ser Pro Ile Asn Leu Asn Ser Arg Glu Ala Arg Tyr Asp Pro Ser
    50                  55                  60

Leu Leu Asp Val Arg Leu Ser Pro Asn Tyr Val Val Cys Arg Asp Cys
65                  70                  75                  80

Glu Val Thr Asn Asp Gly His Thr Ile Gln Val Ile Leu Lys Ser Lys
                85                  90                  95

Ser Val Leu Ser Gly Gly Pro Leu Pro Gln Gly His Glu Phe Glu Leu
            100                 105                 110

Tyr Glu Val Arg Phe His Trp Gly Arg Glu Asn Gln Arg Gly Ser Glu
        115                 120                 125

His Thr Val Asn Phe Lys Ala Phe Pro Met Glu
    130                 135
```

<210> SEQ ID NO 31
<211> LENGTH: 153
<212> TYPE: PRT
<213> ORGANISM: Homo sapiens

<400> SEQUENCE: 31

```
Met Ala Asp Leu Ser Phe Ile Glu Asp Thr Val Ala Phe Pro Glu Lys
1               5                   10                  15

Glu Glu Asp Glu Glu Glu Glu Glu Gly Val Glu Trp Gly Tyr Glu
            20                  25                  30

Glu Gly Val Glu Trp Gly Leu Val Phe Pro Asp Ala Asn Gly Glu Tyr
        35                  40                  45

Gln Ser Pro Ile Asn Leu Asn Ser Arg Glu Ala Arg Tyr Asp Pro Ser
    50                  55                  60

Leu Leu Asp Val Arg Leu Ser Pro Asn Tyr Val Val Cys Arg Asp Cys
65                  70                  75                  80

Glu Val Thr Asn Asp Gly His Thr Ile Gln Val Ile Leu Lys Ser Lys
                85                  90                  95

Ser Val Leu Ser Gly Gly Pro Leu Pro Gln Gly His Glu Phe Glu Leu
            100                 105                 110

Tyr Glu Val Arg Phe His Trp Gly Arg Glu Asn Gln Arg Gly Ser Glu
```

|   |   | 115 |   |   | 120 |   |   |   | 125 |   |
|---|---|---|---|---|---|---|---|---|---|---|

His Thr Val Asn Phe Lys Ala Phe Pro Met Glu Val Arg Ile Thr Asn
130 135 140

His Leu Val Lys Ile Leu Phe Ser Glu
145 150

<210> SEQ ID NO 32
<211> LENGTH: 1710
<212> TYPE: DNA
<213> ORGANISM: Homo sapiens

<400> SEQUENCE: 32

```
aacgcacgcc tgcttgcact cacactgcgg ttcacacccg caggcgctct cgcacacaca      60
ctgccgctcc gcgggctcac actccccccac gcgcgctccg ctccggctcc agccccgcgc    120
ccagcgaagg cgcaggcact gctgccgaga gcgccgaggg gccccgcggc cttcccatgg    180
cggacctgag ctgcatcgaa gataccgtcg ccttccccga aaggaagag atgaggagg       240
aagaagagga gggtgtggag tggggctacg aggaaggtgt tgagtggggt ctggtgtttc    300
ctgatgctaa tggggaatac cagtctccta ttaacctaaa ctcaagagag ctaggtatg     360
accccctcgct gttggatgtc cgcctctccc caaattatgt ggtgtgccga gactgtgaag    420
tcaccaatga tggacatacc attcaggtta tcctgaagtc aaaatcagtt ctttcgggag    480
gaccattgcc tcaagggcat gattttgaac tgtacgaagt gagatttcac tggggaagag   540
aaaaccagcg tggttctgag cacacggtta atttcaaagc ttttcccatg gaggtaagaa    600
taacaaatca tcttgtaaaa atcttgtttt ctgaataaag tattcagcga tttactgaaa    660
atgatttagt ttaaaagtag atgcatagct cttgaattt atcagtttat actaaaattt    720
aaaaaatgct taatgcaatg gaagcctagg gcagcacatg aaacctcctg tctactctcg    780
tggcttggcg tgtgcgcatg agcacatggc cagaaaggca atctacagta ttaaatttca   840
ccctagtgtt actattcttg taaaaattct gcctctgcaa attcagtagg tcatttttgt    900
ggatgctttg ataggtgac gagctgaaga caagcaaccg ttggagaaac ctcaacagta    960
atgaaaagtg taggtttgct agtttaaaat tggtgggttg gtttattca cccaagcca    1020
cttggggagg gagggagaaa gagagatttt ttgagagtga ttctttttgtc caagaattc   1080
cctccccgac ttacgttctt agttaacttc tgctgtttct ttgatacgca gttgaaatct   1140
tatgtcttct gtgggacttt tctctagttt tttccctagg cagaattcat ctctctctct   1200
ctgctccctg tatgcttgat agggcactgc catggcgctg gccccatggg ttgtaccatt   1260
tagtctccac agcgtctttc ttgctgcctg tgagctcctg aggaccgaag ctccctctca   1320
ccccctttt actcccatca tttgcccact gccaggcaca gtggagatag acagttcaca   1380
ctggtgaaag tgagggatg ttggattcag tccacgtctt gatgttattt ctagaaggaa    1440
cctcagttta ccccagaaaa tagccctttg gtgtcatgta agagtatgtt ctggggctg    1500
ctggtcttcc agtcttttt ttttgacatt cacaactgtg catgtgctta atattaaata   1560
taaaattgct catgaccaga tgcaatatcc agtaccactt cagtggctgg aaatcatggc    1620
tgtataattc tatgtcagtg atacatgtat tttagagtat tctgttgaag tgtttgacag    1680
cattactgta attataaaaa aaaaaaaaaa                                    1710
```

<210> SEQ ID NO 33
<211> LENGTH: 1710
<212> TYPE: DNA
<213> ORGANISM: Homo sapiens

<400> SEQUENCE: 33

```
aacgcacgcc tgcttgcact cacactgcgg ttcacacccg caggcgctct cgcacacaca    60
ctgccgctcc gcgggctcac actccccac gcgcgctccg ctccggctcc agccccgcgc    120
ccagcgaagg cgcaggcact gctgccgaga gcgccgaggg gccccgcggc cttcccatgg   180
cggacctgag ctgcatcgaa gataccgtcg ccttccccga aaggaagag gatgaggagg    240
aagaagagga gggtgtggag tgggctacg aggaaggtgt tgagtggggt ctggtgtttc    300
ctgatgctaa tgggaatac cagtctccta ttaacctaaa ctcaagagag gctaggtatg   360
accctcgct gttggatgtc cgcctctccc caaattatgt ggtgtgccga gactgtgaag   420
tcaccaatga tggacatacc attcaggtta tcctgaagtc aaaatcagtt ctttcgggag   480
gaccattgcc tcaagggcat gattttgaac tgtacgaagt gagatttcac tggggaagag   540
aaaaccagcg tggttctgag cacacggtta atttcaaagc ttttcccatg gaggtaagaa   600
taacaaatca tcttgtaaaa atcttgtttt ctgaataaag tattcagcga tttactgaaa   660
atgatttagt ttaaaagtag atgcatagct cttgaatttt atcagtttat actaaaattt   720
aaaaaatgct taatgcaatg gaagcctagg gcagcacatg aaacctcctg tctactctcg   780
tggcttggcg tgtgcgcatg agcacatggc cagaaaggca atctacagta ttaaatttca   840
ccctagtgtt actattcttg taaaaattct gcctctgcaa attcagtagg tcattttgt    900
ggatgctttg gataggtgac gagctgaaga caagcaaccg ttggagaaac ctcaacagta   960
atgaaaagtg taggttttgct agtttaaaat tggtgggttg gttttattca ccccaagcca  1020
cttggggagg gagggagaaa gagagatttt ttgagagtga ttcttttgtc caaagaattc   1080
cctcccgac ttacgttctt agttaacttc tgctgtttct ttgatacgca gttgaaatct   1140
tatgtcttct gtgggacttt tctctagttt ttttccctagg cagaattcat ctctctctct  1200
ctgctcctg tatgcttgat agggcactgc catggcgctg ccccatgggt tgtaccatt    1260
tagtctccac agcgtctttc ttgctgcctg tgagctcctg aggaccgaag ctccctctca  1320
cccccttttt actcccatca tttgcccact gccaggcaca gtggagatag acagttcaca  1380
ctggtgaaag tgagggggatg ttggattcag tccaggtctt gatgttattt ctagaaggaa   1440
cctcagttta ccccagaaaa tagcccttttg gtgtcatgta agagtatgtt ctggggggctg  1500
ctggtcttcc agtctttttt ttttgacatt cacaactgtg catgtgctta atattaaata   1560
taaaattgct catgaccaga tgcaatatcc agtaccactt cagtggctgg aaatcatggc   1620
tgtataattc tatgtcagtg atacatgtat tttagagtat tctgttgaag tgtttgacag   1680
cattactgta attataaaaa aaaaaaaaaa                                    1710
```

<210> SEQ ID NO 34
<211> LENGTH: 1825
<212> TYPE: DNA
<213> ORGANISM: Homo sapiens

<400> SEQUENCE: 34

```
cctcgctctg ctggggcctc cggacgcgct tcccacgcgg gtctctggaa cactcggtcc    60
gaacgcacgc ctgcttgcac tcacactgcg gttcacaccc ggaggcgctc tcgcactcac   120
actgccgctc acgcgtgctc acactccccc acgcgcgctc cgctccggct ccagccccgc   180
gcccagcgaa ggcgcaggca ctgctgccga gagcgccgag gggccccgcg gccttcccat   240
ggcggacctg agcttcatcg aagataccgt cgccttcccc gagaaggaag aggatgagga   300
```

```
ggaagaagag gagggtgtgg agtggggcta cgaggaaggt gttgagtggg gtctggtgtt      360
tcctgatgct aatggggaat accagtctcc tattaaccta aactcaagag aggctaggta      420
tgacccctcg ctgttggatg tccgcctctc cccaaattat gtggtgtgcc gagactgtga      480
agtcaccaat gatggacata ccattccaggt tatcctgaag tcaaaatcag ttctttcggg      540
aggaccattg cctcaagggc atgaatttga actgtacgaa gtgagatttc actggggaag      600
agaaaaccag cgtggttctg agcacacggt taatttcaaa gcttttccca tggagctcca      660
tctgatccac tggaactcca ctctgtttgg cagcattgat gaggctgtgg ggaagccgca      720
cggaatcgcc atcattgctc tgtttgttca gataggaaag gaacatgttg gcttgaaggc      780
tgtgactgaa atcctccaag atattcagta aaggggaag tccaaaacaa taccttgctt       840
taatcctaac actttattac cagaccctct gctgcgggat tactgggtgt atgaaggctc      900
tctcaccatc ccaccttgca gtgaaggtgt cacctggata ttattccgat acctttaac      960
tatatcccag ctacagatag aagaatttcg aaggctgagg acacatgtta aggggggcaga    1020
acttgtggaa ggctgtgatg ggattttggg agacaacttt cggcccactc agcctcttag    1080
tgacagagtc attagagctg catttcagta gccaaagagg acaggaacaa gtctgtcttc    1140
atgagggtat gtccagatta agtaaggaaa atgaggtgca cagctactta aacctagcgt    1200
accaaaggta cacttattgt gatcctggta atttagtaat aaaagcgtat gtacttcatc    1260
ttgataaaat ttatgacaca ttcttgagct ctgttaatta caggtcaagt aggtatttta    1320
attttatgca gtattgaaga aaaactatga ttatattttc ctatcagagt agcctttaat    1380
tccaagtttt ggtggctttc ataagaacag acaccctcag gcccagaaaa agtgacatgc    1440
atgcatacct ctttagtaac ttaccatgtt gtccccgtga agcagcacca gtcatgtccc    1500
agtgaccaag gagcacatag gaggggactt ggggagcgtg tgagcctcag tgtggaccct    1560
tctcgtctcc tgcagaattg atcctcttgt ttctcagggg agggagcata tctggcatgc    1620
attgaaatac ttcttctatg gaagtgcctt ttatatgata aattgagaag cacttattaa    1680
ttatctgaat atgatacact attgattgaa acataatcta tgtattttaa tatatagaat    1740
tcaatgtatg tattccttac tcttaaggaa ctaacaaaat aaaatatcac aaacacggaa    1800
gagataaaat ataaaacaaa ctata                                          1825

<210> SEQ ID NO 35
<211> LENGTH: 510
<212> TYPE: DNA
<213> ORGANISM: Homo sapiens

<400> SEQUENCE: 35
gaaagataac tgaatcaatg tgaagtctgt gagtccctcc agttgtcttc ctcctcatca       60
ggactaaaac tggacttaag aggcagtgat ccactaagca ctgcttctgt tcagaaataa      120
gaaggaagga attcatacag agaactcgta ttaagccagt agtttgtgtc tacttgtgat      180
cctcttgtgc tccatctgat ccactggaac tccactctgt ttggcagcat tgatgaggct      240
gtggggaagc cgcacggaat cgccatcatt gctctgtttg ttcagatagg aaaggaacat      300
gttggcttga aggctgtgac tgaaatcctc caagatattc agtataaggg gaagtccaaa      360
acaataccct tgctttaatc ctaacacttt attaccagacc ctctgctgcg ggattactgg     420
gtgtatgaag gctctctcac catcccacct tgcagtgaag gtgtcacctg gatattattc      480
cgatacccctt taactatatc ccagctacag                                      510
```

METHOD FOR MANAGING PAIN

GRANT FUNDING DISCLOSURE

This invention was made with government support under grant number DE022903, awarded by the National Institutes of Health. The government has certain rights in the invention.

FIELD OF DISCLOSURE

The invention relates to materials and methods for treating or preventing pain.

INCORPORATION BY REFERENCE OF MATERIALS SUBMITTED ELECTRONICALLY

This application contains, as a separate part of the disclosure, a Sequence Listing in computer readable form (Filename: 51774A_Seqlisting.txt; Size: 73,7002 bytes; Created: Jul. 13, 2018), which is incorporated by reference in its entirety.

BACKGROUND

Persistent pain costs about $650 billion annually in health care costs and lost productivity. A National Health Interview Survey conducted in 2012 estimated that nearly 50 million American adults suffer from significant chronic pain or severe pain. Press release, American Pain Society, Aug. 18, 2015, found at americanpainsociety.org/about-us/pressroom/nih-study-shows-prevalence-of-chronic-or-severe-pain-in-u-s-adults. Other studies suggest the burden of pain is higher.

Currently available treatments for chronic pain are associated with disadvantages that leave most patients inadequately treated. Current local anesthetics, for example, are short acting and disabling due to complete sensory and motor blockade. Opioid drugs, including morphine, are the primary treatment for, e.g., post-operative and chronic pain conditions. Long-term opioid use in treating chronic, non-cancer pain has increased dramatically over the past few decades, and opioid abuse, tolerance and dependence are major public health concerns. Indeed, side-effects of opioid administration (e.g., tolerance, drug dependence/addiction, respiration depression, constipation, nausea, pruritis, sedation, and mood swings), limit opioids' therapeutic potential, and the absence of suitable alternatives has led to an epidemic of opioid overuse, abuse, and life-threatening complications. In the United States, prescription opioid abuse costs alone were estimated at about $55.7 billion in 2007. Almost half this cost was attributed to workplace costs (e.g., lost productivity), 45% to healthcare costs (e.g., abuse treatment), and 9% to criminal justice costs. Birnbaum et al., Pain medicine 2011; 12:657-67.

Despite a considerable amount of research into pain medications, there remains a need for therapeutic options that provide analgesia while minimizing (or avoiding) the adverse effects associated with opioid use.

SUMMARY

The disclosure provides a method of treating or preventing pain in a subject (e.g., human) in need thereof. In one aspect, the method comprises administering to the subject an expression vector (e.g., a viral vector, such as an adeno-associated viral vector or a herpes simplex viral vector) comprising a nucleic acid sequence encoding carbonic anhydrase 10 or carbonic anhydrase 11 such that the nucleic acid is expressed to produce carbonic anhydrase 10 or carbonic anhydrase 11. Alternatively, the expression vector (e.g., a viral vector, such as an adeno-associated viral vector or a herpes simplex viral vector) comprises a nucleic acid sequence encoding carboxyl anhydrase 8 or a carbonic anhydrase 8 fragment. Human and mouse versions of carbonic anhydrases are contemplated (CA8/Car8, CA8/Car8 fragments, CA10/Car10 and/or CA11/Car11). It will be appreciated that descriptions herein relating to human versions of carbonic anhydrases (e.g., CA8, CA8 fragments, CA10 and/or CA11) also apply to the mouse versions (Car8, Car8 fragments, Car10, and/or Car11). The nucleic acid sequence encoding the fragment of carbonic anhydrase 8 (CA8 human or Car8 mouse) comprises (or consists essentially of or consists of) the first three exons of the carbonic anhydrase 8 coding sequence. Optionally, the nucleic acid sequence encoding the fragment of carbonic anhydrase 8 is alternative transcript CA8-204, comprising the first three exons with an elongated exon 3 and retained intron. In various aspects, the carbonic anhydrase is an antagonist of ITPR1-activation (pITPR1) and ITPR1-mediated intracellular calcium release.

In various aspects, the pain is neuropathic pain, cancer pain, or inflammatory pain. In various aspects, the method comprises administering the expression vector to the dorsal root ganglion of the subject or administering the expression vector via intraarticular injection, intradermal delivery, or intra-oral delivery.

The foregoing summary is not intended to define every aspect of the invention, and additional aspects are described in other sections, such as the Detailed Description. The entire document is intended to be related as a unified disclosure, and it should be understood that all combinations of features described herein are contemplated, even if the combination of features are not found together in the same sentence, or paragraph, or section of this document. In addition, the invention includes, as an additional aspect, all embodiments of the invention narrower in scope in any way than the variations specifically mentioned above. With respect to aspects of the invention described or claimed with "a" or "an," it should be understood that these terms mean "one or more" unless context unambiguously requires a more restricted meaning. With respect to elements described as one or more within a set, it should be understood that all combinations within the set are contemplated. If aspects of the invention are described as "comprising" a feature, embodiments also are contemplated "consisting of" or "consisting essentially of" the feature.

Although the applicant(s) invented the full scope of the claims appended hereto, the claims appended hereto are not intended to encompass within their scope the prior art work of others. Therefore, in the event that statutory prior art within the scope of a claim is brought to the attention of the applicants by a Patent Office or other entity or individual, the applicant(s) reserve the right to exercise amendment rights under applicable patent laws to redefine the subject matter of such a claim to specifically exclude such statutory prior art or obvious variations of statutory prior art from the scope of such a claim. Variations of the invention defined by such amended claims also are intended as aspects of the invention. Additional features and variations of the invention will be apparent to those skilled in the art from the entirety of this application, and all such features are intended as aspects of the invention.

BRIEF DESCRIPTION OF THE FIGURES

FIG. 8 is an amino acid sequence encoding CA10 (SEQ ID NO: 9).

FIG. 9 is a nucleotide sequence encoding CA10-203 (SEQ ID NO: 12).

FIG. 10 is a nucleotide sequence encoding a CA8 fragment, CA8-204 (SEQ ID NO: 13).

FIG. 21B provides the 5HT-3 receptor promoter sequence (SEQ ID NO: 16).

FIG. 22 provides the sequence of NPY-Y1 Receptor Promoter—exon 1A (SEQ ID NO: 17) (JBC Vol. 270, No. 45, Issue of November 10, pp. 27272-27276, 1995).

FIG. 23 provides the sequence of NPY-Y1 Receptor Promoter—exon 1B (SEQ ID NO: 18) (JBC Vol. 270, No. 45, Issue of November 10, pp. 27272-27276, 1995).

FIG. 24 provides the sequence of NPY-Y1 Receptor Promoter—exon 1C (SEQ ID NO: 19) (JBC Vol. 270, No. 45, Issue of November 10, pp. 27272-27276, 1995).

FIG. 25A provides the sequence of mouse (SEQ ID NO: 20), rat (SEQ ID NO: 21), and human (SEQ ID NO: 22) Nav1.8 Promoter SCN10A (J Neurochem. 2008 August; 106(3): 1209-1224).

FIG. 25B provides the sequence of human Nav1.8 Promoter SCN10A (SEQ ID NO: 23).

FIG. 26 provides the sequence of Nav1.7 Promoter SCN9A (SEQ ID NO: 24).

FIG. 27B provides the sequence of Trk-A promoter (SEQ ID NO: 26).

FIG. 28 provides the sequence of an Advillin promoter (SEQ ID NO: 27).

FIG. 29 provides the sequence of CGRP Receptor promoter (SEQ ID NO: 28).

FIG. 30 provides the sequence of GRIN3A promoter (SEQ ID NO: 29).

FIG. 33 depicts a gel showing that RYR1 binds to CA10 (Car10) as demonstrated by immunoprecipitation (IP) and western blotting (WB) detection.

FIGS. 34A and 34B are gels and provide bar graphs showing that Car10 and CA10 inhibited forskolin-induced pITPR1. FIG. 34A provides results for untreated controls (no forskolin). FIG. 34B provides results from treatment with 1 µM forskolin.

FIG. 35 is a bar graph showing that expression of V5-Car10 and V5-CA10 in HEK293 cells inhibits ATP-induced cytoplasmic calcium release.

FIG. 36 is a bar graph showing that 5HT-induced RYR-dependent calcium release in NBL cells is inhibited by ryanodine.

FIG. 38 shows construction of pCMV-N-flag-CA8-204$^G$ and pCMV N-flag-CA8-204$^C$.

FIG. 39 shows construction of pAAV-flag-CA8-204$^G$ (ALT G) and pAAV-flag-CA8-204$^C$ (ALT C).

FIG. 45 shows that CA8 204$^C$ inhibits forskolin induced phosphorylation of pITPR1.

DETAILED DESCRIPTION

Figure 1A:
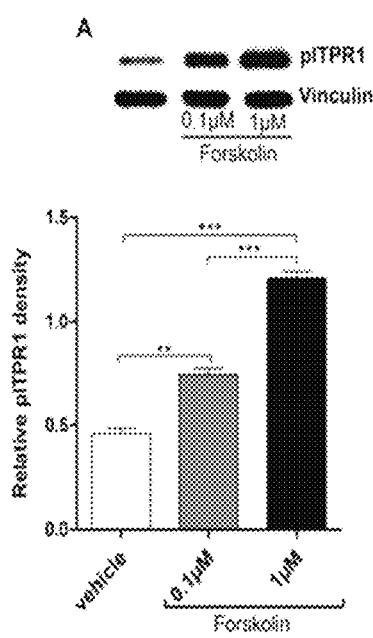
FIG. 1A-1C are bar graphs illustrating relative pITPR1 density (FIG. 1A), relative V5 density (FIG. 1B), and relative pITPR1 density (FIG. 1C). Overexpression of Car10/CA10 in HEK293 cells inhibits forskolin-induced ITPR1 phosphorylation (pITPR1). HEK293 cells were transfected with AAV-V5 vectors expressing murine (Car10) and human (CA10). Western blot analysis demonstrates that forskolin increases pITPR1 levels in a dose-dependent manner (FIG. 1A). Following V5-Car10 and V5-CA10 vector transfection, CA10 and Car10 protein overexpression was demonstrated using V5 tag on western blotting (FIG. 1B). Car10 and CA10 overexpression reduced ITPR1 phosphorylation in response to 1 micromolar forskolin stimulation in HEK293 cells (FIG. 1C). N=6, data are presented as means±SEM  $P<0.01$, * $P<0.001$, one-way ANOVA.

In various aspects, the disclosure relates to materials and methods, which provide safe and effective analgesia. This disclosure is the first to show that Carbonic anhydrase 10 (CA10 (human) and Car10 (rodent)) produces analgesia and prevents hyperalgesia, e.g., in chronic neuropathic and inflammatory pain models. In at least one aspect, the materials and methods relieve pain with minimal interference with motor and other sensory functions, thereby improving quality-of-life while minimizing the need for opioid use.

In one aspect, the disclosure provides a method of treating or preventing pain in a subject in need thereof. The method comprises administering to the subject an expression vector comprising a nucleic acid sequence encoding carbonic anhydrase 10 or carbonic anhydrase 11 such that the nucleic acid is expressed to produce carbonic anhydrase 10 or carbonic anhydrase 11 in the subject. In an alternative embodiment, the method comprises administering to the subject an expression vector comprising a nucleic acid sequence encoding a fragment of carbonic anhydrase 8 such that the nucleic acid is expressed to produce the fragment of carbonic anhydrase 8 in the subject. The nucleic acid sequence encoding fragment of carbonic anhydrase 8 comprises the first three exons of CA8, and optionally the nucleic acid sequence encoding the CA8 fragment is CA8-204 described herein. In various embodiments, the expression vector is a viral vector, such as an adeno-associated viral vector or a herpes simplex viral vector.

Aspects of the invention are described further below. The use of section headings are merely for the convenience of reading, and not intended to be limiting per se. The entire document is intended to be viewed as a unified disclosure, and it should be understood that all combinations of features described herein are contemplated.

Carbonic Anhydrases

Carbonic anhydrase 10 (CA10) is a member of the carbonic anhydrase (CA) super gene family and one of three catalytically inactive CA isoforms. While CA10 retains a central carbonic anhydrase motif, it lacks the catalytic zinc coordinating residues critical for enzymatic activity. The functions of CA10 remain were previously unknown. Sequence comparison revealed 100% identity between humans (Homo sapiens), rat (Rattus norvegicus), and mouse (Mus musculus) CA10 proteins, and 90% identity at the amino acid level with zebra fish (Danio rerio). There are nine transcripts encoding human CA10, resulting in seven functional isoforms. Nucleic acid and amino acid sequences of human CA10 are set forth in Genbank Accession Nos. NM_020178 (SEQ ID NO: 3); NP_064563 (SEQ ID NO: 4); NM_001082534 (SEQ ID NO: 5); NP_001076003 (SEQ ID NO: 6); NM_001082533 (SEQ ID NO: 7) and NP_001076002 (SEQ ID NO: 8); the amino acid sequence of human CA10 is also provided in UniProtKB Q9NS85 (SEQ ID NO: 9).

In various aspects, the expression vector comprises a nucleic acid sequence encoding a peptide comprising at least 90% identity (e.g., at least 95% identity or 100% identity) to SEQ ID NO: 2. In various aspects, the expression vector comprises a nucleic acid sequence having at least 90% identity (e.g., at least 95% or 100% identity) to SEQ ID NO: 1. As used herein, "at least 90% identity" and similar terms encompass any integer from, e.g., 90% to 100%, such as 90%, 91%, 92%, 93%, 94%, 95%, 96%, 97%, 98% or 99% and the like. Also, the term "at least [percentage] identity" encompasses any percentage that is greater than or equal to the number of identical nucleotides or amino acids divided by the total number of nucleotides or amino acids ([at least percentage identity]≥[number of identical nucleotides or amino acids]/[total number of nucleotides or amino acids]). The calculation of percent identity of aligned amino acids (or nucleotides) of two or more sequences is well understood in the art and is determined conventionally using known computer programs. For example, alignment of two or more sequences to determine percent sequence identity is optionally performed using the algorithm described by Altschul et al. (Nucleic Acids Res., 25:3389-402 (1997)) as incorporated into BLAST (basic local alignment search tool) programs, available on the National Center for Biotechnology Information website. The gene product exhibits at least one carbonic anhydrase (CA10) activity, such as analgesia or antagonist of ITPR1-activation (pITPR1) and ITPR1-mediated intracellular calcium release.

It is surprising that CA10 and Car10 display the activities described herein (e.g., analgesia) despite the considerable sequence divergence between CA8 and CA10. The amino acid sequence of CA10 demonstrates an overall percent identity of only 25-57% to other CA isozymes, with the highest percent identity to a CA11. Specifically, CA10 (NP_001076003.1) exhibits only about 33% identity with CA8 (NP_001308766.1) at the amino acid level. Indeed, CA10 most closely resembles CA11 compared CA8 or any other family member at the amino acid level, with CA10 demonstrating sequence identity of 58% with CA11 and 33% with CA8. CA10 lacks two out of three zinc-ligand binding histidine residues, suggesting a lack of CA enzymatic activity. CA11 also lacks zinc-ligand binding sites, suggesting a lack of enzymatic activity. Similar to CA8, CA10 was found to inhibit forskolin-induced phosphorylation of ITPR1 (pITPR1); and ATP-induced ITPR1 mediated intracellular calcium release in HEK293 and NBL cells. CA8 is thought to be an allosteric inhibitor of IP3 ligand binding and activation of ITPR1 leading to intracellular calcium release. Allosteric inhibition of ITPR1 activation was previously believed to depend on CA8 binding with ITPR1 (Hirota J, et al., Biochem J 372, 435-441). In distinct contrast to CA8, CA10 and Car10 do not bind ITPR1 in IP-westerns. Surprisingly, despite the lack of binding with ITPR1, CA10/Car10 and CA8-204 inhibit ITPR1 activation (pITPR1) and ATP induced intracellular calcium release, and produce profound analgesia in vivo.

In various aspects, the expression vector comprises a nucleic acid sequence encoding a CA8 fragment. The nucleic acid sequence comprises (or consists of) the first three exons of the CA8 (or Car8) coding sequence. Optionally, the nucleic acid sequence encoding the CA8 fragment is CA8-204, the sequence of which is provided herein in FIG. 10. In some embodiments, the CA8 fragment is CA8-204C, the nucleic acid sequence of which is set forth in SEQ ID NO: 32 (the amino acid sequence is set forth in SEQ ID NO: 30). In some embodiments, the CA-fragment is CA8-204G, the nucleic acid sequence of which is set forth in SEQ ID NO: 33 (the amino acid sequence is set forth in SEQ ID NO: 31). In some embodiments, the CA-8 fragment is CA8-202 (SEQ ID NO: 34) or CA-203 (SEQ ID NO: 35). In various aspects, the expression vector comprises a nucleic acid sequence having at least 90% identity (e.g., at least 95% or 100% identity) to a CA8-204 nucleic acid sequence described herein. As used herein, "at least 90% identity" and similar terms encompass any integer from, e.g., 90% to 100%, such as 90%, 91%, 92%, 93%, 94%, 95%, 96%, 97%, 98% or 99% and the like. The nucleic acid sequence of a CA8 fragment comprising exons 1-3 is provided as SEQ ID NO: 1. The nucleic acid sequence of a CA8 fragment comprising exons 1-5 is provided as SEQ ID NO: 35. The nucleic acid sequence of a CA8 fragment comprising exons 1-8 is provided as SEQ ID NO: 34. The nucleotide and amino acid sequences of CA11 are provided as SEQ ID NOs: 10 and 11. The expression product of any of the sequences described herein exhibits at least one carbonic anhydrase activity, such as analgesia or antagonist of ITPR1-activation (pITPR1) and ITPR1-mediated intracellular calcium release.

Descriptions of materials and methods concerning CA8, CA10, and CA11 also apply to the mouse (version of the proteins, Car8, Car10, and Car11, which are contemplated for use in various aspects of the disclosure.

Expression Vector

A "vector" or "expression vector" is any type of genetic construct comprising a nucleic acid (DNA or RNA) for introduction into a host cell. In various embodiments, the expression vector is a viral vector, i.e., a virus particle comprising all or part of the viral genome, which can function as a nucleic acid delivery vehicle. Viral vectors comprising exogenous nucleic acid(s) encoding a gene product of interest also are referred to as recombinant viral vectors. As would be understood in the art, in some contexts, the term "viral vector" (and similar terms) may be used to refer to the vector genome in the absence of the viral capsid. Viral vectors for use in the context of the disclosure include, for example, retroviral vectors, herpes simplex virus (HSV)-based vectors, parvovirus-based vectors, e.g., adeno-associated virus (AAV)-based vectors, AAV-adenoviral chimeric vectors, and adenovirus-based vectors. Any of these viral vectors can be prepared using standard recombinant DNA techniques described in, e.g., Sambrook et al., Molecular Cloning, a Laboratory Manual, 2d edition, Cold Spring Harbor Press, Cold Spring Harbor, N.Y. (1989); Ausubel et al., Current Protocols in Molecular Biology, Greene Publishing Associates and John Wiley & Sons, New York, N.Y. (1994); Coen D. M, Molecular Genetics of Animal Viruses in Virology, $2^{nd}$ Edition, B. N. Fields (editor), Raven Press, N.Y. (1990) and the references cited therein. Additionally, viral vectors can be prepared with a large genomic coding sequence from humans and other host species, including an entire gene including 5' and 3' regulatory sequences with the application of homologous recombination-mediated cloning and manipulation of target genomic regions using Gateway cloning (Hartley et al., Genome Res 2000, 10:1788-1795) and/or "recombineering" systems (Copeland et al., Nat Rev Genet 2001, 2:769-779).

In various embodiments, a random or semirandom library is developed in which DNAs encoding precursors of carboxyl anhydrase peptides that differ are provided. Such a library may contain hundreds or more different sequences. In various aspects, thousands or more (at least 1000 or at least 10,000) different expression cassettes differing in the sequence of DNAs encoding the precursors of carboxyl anhydrase peptides constitute the library. Such a library can be constructed by first generating a population of random or semi-random oligonucleotides encoding precursors of peptides having one or more desired characteristics (e.g., precursors of carboxyl anhydrase peptides resembling CA8, CA10 or CA11). This population of oligonucleotides then can be cloned into the cassette backbone (i.e., in frame with the preproprotein signal sequence and optional biomarker).

An example of a method for constructing random or semi-random libraries employs the GATEWAY™ system (Invitrogen, Carlsbad, Calif.). In the GATEWAY™ system, ccdB is used as a negative selectable marker that, if present, kills the bacteria cell. ccdB is replaced by a random or semi-random sequence through site specific recombination carried out by a modified lambda integrase. Two bacterial strains are used in GATEWAY™ technology, ccdB sensitive and ccdB resistant. The ccdB containing plasmid is propagated in ccdB resistant bacteria and purified. This plasmid is then used for in vitro recombination. The recombination product is transformed into a ccdB sensitive bacteria selecting for plasmids that have had the ccdB gene replaced by the gene-of-interest during the in vitro recombination. By replacing ccdB, the background in cloning and library construction is dramatically reduced or eliminated allowing the shuttling of genes into and out or a variety of plasmids at will. As a starting point the base plasmids are grown in bacteria that are resistant to the toxic effects of ccdB of which there are a very limited number of genotypes available. To employ the GATEWAY™ technology in the context of this disclosure, using a large viral vector system, a bacterial strain amenable to transformation to large DNAs (such as BACs) desirably is modified to express a gene that confers insensitivity to ccdB. A preferred strain is derived from the DH10B bacterial strain used in BAC propagation and manipulation, which also has a mutation (fhuA::IS2) that increases their proclivity to transformation by very large DNAs.

In some embodiments, the viral vector is an HSV-based vector. HSV is an enveloped, icosahedral, double-stranded DNA virus that infects mammals, including humans. Wild-type HSV infects and replicates in both terminally differentiated non-dividing cells and dividing cells. An advantage of HSV vectors is the virus's ability to enter a latent stage resulting in long-term DNA expression. Additionally, HSV preferentially infects sensory nerves, often escapes immune surveillance, doesn't spread in the CNS/PNS, and exhibits superior retrograde transport (e.g., intradermal, intra-articular or peripheral nerve). Additionally, HSV allows for large genomic inserts using Gateway and/or recombineering techniques. The sequence of HSV is available at ncbi.nlm.nih.gov:80/entrez/query.fcgi?cmd=Retrieve&db= nucleotide&list_uid-s=9629378&dopt=GenBank&term= hsv-1&qty=1.

Optionally, the HSV vector is replication-deficient, e.g., at least one HSV gene essential for replication or packaging is rendered non-functional (mutated or deleted). For instance, a replication-deficient HSV vector may lack one or more gene functions of the early regions, the immediate-early regions, or the late regions of the HSV genome. In various aspects, the HSV vector is "multiply-deficient," meaning that more than one gene function essential for viral replication has been disrupted. For example, multiply-deficient vectors may lack gene functions from two or more of the early, immediate-early, and late regions of the HSV genome. The HSV vector optionally lacks a functional immediate early gene selected from the group consisting of ICP0, ICP4, ICP22, ICP27, ICP47, and any combination thereof, for example, lacks functional ICP0, ICP4, ICP22, ICP27, and ICP47 genes (optionally rendered non-functional by deletion). Non-essential genes also may be removed from a viral vector, such as an HSV vector, to accommodate large pieces of exogenous DNA. For example, an HSV vector can essentially lack the entire HSV genome. In this respect, the vector preferably comprises the viral inverted terminal repeats (ITRs) and/or the packaging signal, although these components are not required in all aspects of the disclosure. Optionally, one or more promoters or the viral ITRs and a packaging signal are left intact (i.e., an HSV amplicon).

The nucleotide encoding CA10 (or Car10) or CA11 (or Car11) optionally replaces native virus genetic sequences that have been removed (optionally to render the vector replication-deficient). The nucleotide encoding CA8 (or Car8) or CA8 fragment (or Car8 fragment) optionally replaces native virus genetic sequences that have been removed (e.g., to render the vector replication-deficient).

The HSV vector, when made replication deficient by the deletion of multiple genomic segments, optionally includes a spacer element to provide viral growth in a complementing cell line similar to that achieved by singly replication deficient HSV vectors. The spacer element can contain any nucleic acid sequence or sequences that are of the desired length and encode the desired analgesic carbonic anhydrase molecule. The spacer element sequence can be coding or non-coding and native or non-native with respect to the HSV genome, but does not restore the replication essential function(s) to the deficient region. In addition, the inclusion of a spacer element in any or all of the deficient HSV regions will decrease the capacity of the HSV vector for large inserts.

In various embodiments, the HSV vectors are replication-defective HSV (rdHSV) vectors that are functionally deleted for all IE genes. An advantage to removing additional IE genes includes, but is not limited to, reducing toxicity in neurons and other cell types. The structure of a representative vector backbone comprises transgene cassettes inserted at, for example, two selected sites in the latency (LAT) locus that are protected against epigenetic silencing by resident insulator/chromatin boundary elements (CTRLs or CTCFs). These elements, along with the HSV LAP2 promoter, provide for long-term expression. The placement of an ectopic insulator adjacent to a transgene cassette inserted into the viral UL50-UL51 intergenic region also enhances prolonged transgene expression from this locus in primary human cells. As merely an example of a suitable vector system, HSV vector propagation reaching high titers has been demonstrated using a ICP4/ICP27/Cre-expressing U2OS cell line that eliminates the inhibitory BAC sequences present in vector constructs by Cre recombination.

It should be appreciated that the deletion of different regions of the HSV vector can alter the immune response of a host. In particular, the deletion of different regions can reduce the inflammatory response generated by the HSV vector. Furthermore, the HSV vector's protein coat can be modified so as to decrease the HSV vector's ability or inability to be recognized by a neutralizing antibody directed against the wild-type protein coat.

Base vectors, complementing cells, and engineering technology can generate safe vectors for long-term expression of CA10 (or Car10), CA11 (or Car11), CA8 (or Car8) and/or CA8 fragments (or Car8 fragments) for promoting analgesia from the following promoters within the Gateway transfer plasmid: sensory neuron specific Nav1.8 (e.g., sodium channel); neuron specific Nav1.7 (e.g., sodium channel); high affinity nerve growth factor receptor (TrkA); somatosensory-specific advillin CA8 driver; and the non-specific constitutive CMV promoter. Inducible promoter sequences, such as the tetracycline responsive promoter, also are appropriate in the context of the disclosure. Advantages of using HSV vectors to deliver human therapeutics include distinct tissue specificity, lack of immune response, and lack of latent reactivation, even in immunocompromised hosts.

In various aspects, the HSV vector comprises an HSV latency-associated transcript (LAT) insulator.

HSV-based vectors are further described in, for example, U.S. Pat. Nos. 5,837,532; 5,846,782; 5,849,572; and 5,804,413; as well as International Patent Publication Nos. WO 91/02788, WO 96/04394, WO 98/15637, and WO 99/06583, which are incorporated herein by reference in their entireties.

An example of an HSV vector for use in the context of the disclosure contains expanded ICP4, or ICP27 deletions, and preferably both. By "expanded" deletions is meant that the HSV vector contains no homologous sequences at either or both of these loci relative to the complementing cell line used for their production. Desirably, the virus has no remaining ICP4 or ICP27 (or both) coding or promoter sequences. Preferably, the deletion in ICP27 extends as well into the UL55 locus, and desirably both genes are deleted. Thus, a virus for use in the context of the disclosure contains extended deletions in ICP4, ICP27 and UL 55 such that there is no viral homology to these genes used in a complementing cell line. Desirably, the vector further does not include any homologous DNA sequences to that employed in the complementing cell line (e.g., even using different regulatory sequences and polyadenylation sequences).

It will be understood that vectors other than HSV-based vectors can be used in the context of the disclosure. For example, adenoviral, adeno-associated viral (AAV) and retroviral vectors are suitable for use in the methods and compositions of the disclosure. Construction of such vectors is known to those of ordinary skill in the art (see, e.g., U.S. Pat. Nos. 4,797,368, 5,691,176, 5,693,531, 5,880,102, 6,210,393, 6,268,213, 6,303,362, and 7,045,344). Non-viral methods can also be utilized for gene delivery and include, but are not limited to, gene-gun application of plasmids (e.g., non-viral expression vector encoding precursors of one or more carboxyl anhydrases described herein). Another non-viral method of gene delivery is electroporation. Alternative, implantable cell lines can be engineered to produce the desired peptide (or library).

In various aspects, the viral vector is an AAV vector. AAV is a DNA virus not known to cause human disease, making it a desirable gene therapy options. The AAV genome is comprised of two genes, rep and cap, flanked by inverted terminal repeats (ITRs), which contain recognition signals for DNA replication and viral packaging. AAV requires co-infection with a helper virus (i.e., an adenovirus or a herpes virus), or expression of helper genes, for efficient replication. AAV vectors used for administration of a therapeutic nucleic acid typically have a majority of the parental genome deleted, such that only the ITRs remain, although this is not required. Delivering the AAV rep protein enables integration of the AAV vector comprising AAV ITRs into a specific region of genome, if desired. Host cells comprising an integrated AAV genome show no change in cell growth or morphology. As such, prolonged expression of therapeutic factors from AAV vectors can be useful in treating persistent and chronic diseases. The AAV vector is optionally based on AAV type 1, AAV type 2, AAV type 3 (including types 3A and 3B), AAV type 4, AAV type 5, AAV type 6, AAV type 7, AAV type 8, AAV type 9, AAV type 10, or AAV type 11. The genomic sequences of AAV, as well as the sequences of the ITRs, Rep proteins, and capsid subunits are known in the art. See, e.g., International Patent Publications Nos. WO 00/28061, WO 99/61601, WO 98/11244; as well as U.S. Pat. No. 6,156,303, Srivistava et al. (1983) J Virol. 45:555; Chiorini et al (1998) J Virol. 71:6823; Xiao et al (1999) J Virol. 73:3994; Shade et al (1986) J Virol. 58:921; and Gao et al (2002) Proc. Nat. Acad. Sci. USA 99:11854.

Expression vectors typically contain a variety of nucleic acid sequences necessary for the transcription and translation of an operably linked coding sequence. For example, expression vector can comprise origins of replication, polyadenylation signals, internal ribosome entry sites (IRES), promoters, enhancers, and the like. The vector of the disclosure preferably comprises a promoter operably linked to the CA10 (or Car10) or CA11 (or Car11) coding sequence. In various aspects, the vector of the disclosure preferably comprises a promoter operably linked to the CA8 (or Car8) or CA8 fragment (or Car8 fragment) coding sequence. "Operably linked" means that a control sequence, such as a promoter, is in a correct location and orientation in relation to another nucleic acid sequence to exert its effect (e.g., initiation of transcription) on the nucleic acid sequence. A promoter can be native or non-native to the nucleic acid sequence to which it is operably linked and native or non-native to a particular target cell type, and the promoter may be, in various aspects, a constitutive promoter, a tissue-specific promoter, or an inducible promoter (e.g., a promoter system comprising a Tet on/off element, a RU486-inducible promoter, an ecdysone-inducible promoter, a rapamycin-inducible promoter, or a metallothionein promoter). For example, in various embodiments, an inducible promoter system is employed that allows the use of a small molecule to induce or stop production of analgesic peptide production.

Examples of promoters include, but are not limited to, a sensory neuron specific promoter (such as the Nav1.8 promoter), a somatosensory-specific promoter (such as the advillin promoter), the p175 promoter, or the TrkA (nerve growth factor receptor) promoter. Other promoters include, but are not limited to, TrkB, TrkC, Nav1.7, CGRP, ASIC3, NPY, NK1, 5HT, GRIN3A, or NF200 promoters. Non-limiting examples of sequences of various promoters are provided herein as FIGS. 21A-30.

Optionally, the virus coat or capsid (i.e., particle surface) is modified to adjust viral tropism. For example, the genome of one serotype of virus can be packaged into the capsid of a different serotype of virus to, e.g., evade the immune response. Alternatively (or in addition), components of the capsid can be modified to, e.g., expand the types of cells transduced by the resulting vector, avoid (in whole or in part) transduction of undesired cell types, or improve transduction efficiency of desired cell types. For example, transduction efficiency is generally determined by reference to a control (i.e., an unmodified, matched viral vector). Improvements in transduction efficiency can result in, e.g., at least about 25%, 50%, 60%, 70%, 80%, 85%, 90%, 95%, 100% improvement in transduction rate of a given cell type. If desired, the capsid can be modified such that it does not efficiently transduce non-target tissues, such as liver or germ cells (e.g., 50% or less, 30% or less, 20% or less, 10% or less, 5% or less of the level of transduction of desired target tissue(s)).

Pain

"Pain" is generally described in terms of duration, cause, and/or afflicted region of the body. The invention includes treatment of any type of pain, including neuropathic pain (e.g., pain initiated or caused by a lesion or disease in the somatosensory nervous system), inflammatory pain (e.g., pain caused by activation and/or sensitization of the nociceptive pain pathway by inflammatory mediators), and/or nociceptive pain (e.g., pain caused by insult or injury of tissues). Many pain disorders or incidents are not easily classifiable, and may entail aspects or characteristics that overlap these general classes. Pain also is classified as to location in the body; somatic pain results from the activation of pain receptors in the body surface or musculoskeletal tissues, while visceral pain is felt in internal organs and is typically caused by the activation of pain receptors in the chest, pelvis, or abdomen.

Neuropathic pain occurs when there is actual nerve damage. Primary afferent somatosensory nerves represent the sensory nerves in the periphery and communicate with second order neurons in the spinal cord dorsal horn. Second order somatosensory nerves connect the spinal cord to the brain stem and third order neurons. Trauma (e.g., injury, surgery, toxic exposures, cancer, and/or metabolic or infectious diseases) can all damage the somatosensory pathway and cause spontaneous pain. Neuropathic pain can manifest as a burning, tingling, shooting, or stinging sensation, or be associated with more severe sensations including stabbing, piercing, cutting, or drilling. This type of pain typically occurs in waves of frequency and intensity, and is typically diffuse throughout portions or all of the body. Examples of neuropathic pain conditions include, but are not limited to, spinal cord injury-mediated pain, central pain syndromes (e.g., caused by a lesion within the nervous system), pain associated with peripheral nerve damage due to entrapment syndromes (e.g., carpel tunnel syndrome, cubital tunnel syndrome, or tarsal tunnel syndrome), multiple sclerosis, fibromyalgia, herpes zoster, virus-related neuropathies, painful traumatic mononeuropathy, polyneuropathy, diabetic neuropathy, post-surgical pain syndromes (e.g., post-mastectomy syndrome, post-thoracotomy syndrome, phantom pain), and complex regional pain syndrome (e.g., reflex sympathetic dystrophy and causalgia). The causes of neuropathic pain are numerous and include, e.g., chemical exposures (e.g., chemotherapy), trauma (e.g., amputation, disc herniation, or spinal cord injury), radiation exposure, metabolic disease, infection, and cancer.

Nociceptive pain is caused by damage to body tissues and is usually described as a sharp, aching, or throbbing pain. This type of pain can result from benign pathology, or by tumors or cancer cells that proliferate and crowd other body parts near the cancer site. Nociceptive pain may also be caused by cancer spreading to the bones, muscles, or joints, or blockage of an organ or blood vessels. Nociceptive pain may be associated with inflammation that includes, e.g., arthritic pain (such as rheumatoid arthritis or osteoarthritis) and inflammation-induced visceral pain (e.g., pain associated with inflammatory bowel disease, irritable bowel syndrome IBS, and the like). Examples of nociceptive pain include, e.g., pain from sprains, bone fractures, burns, bumps, bruises, inflammation (e.g., inflammation resulting from an infection, trauma, or arthritic disorder), or obstructions, as well as myofascial pain (which may indicate abnormal muscle or tendon stresses). Cancer pain can be nociceptive or neuropathic.

In various aspects, the method includes treatment of, e.g., long term, persistent pain, chronic pain, breakthrough pain, subacute pain, acute pain, and cancer pain. Acute pain is generally a limited physiological response to a discrete bodily insult (e.g., inflammation, surgery, bone fracture, headache, sprain, strains, burn, or chemical exposure). Acute pain generally lasts three to six months in duration. Chronic pain persists longer than would be expected for healing from a discrete bodily insult, e.g., more than three months. Chronic pain is associated with disorders such as back pain, trauma (e.g., surgery or wounds) causing nerve damage (including spinal cord injury), myofascial pain, arthritis, cancer-related pain, neuropathic pain, and fibromyalgia. In some embodiments, the pain involves acute-on-chronic pain, where acute pain flashes are superimposed on persistent, chronic pain.

Efficacy in treating (i.e., reducing, easing, suppressing, or alleviating) or preventing pain in a subject in need thereof is determined using any suitable method. In animal models, analgesic efficacy is measured, for example, using the tail withdrawal test, tail flick test, bee venom test, capsaicin test, or tail-clip test. Animal pain models are well characterized in the art and described in, e.g., Lariviere et al., Pain 97 (2002) 75-86. In humans, efficacy of (or need of) treatment is monitored or determined using, e.g., a pain score, time to re-medication, and quality of life measurements. Several tools are used in clinical settings to establish a numeric rating of pain intensity (see, e.g., McCaffery et al., (1989), Pain: Clinical manual for nursing practice, Mosby St. Louis, MO) or a verbal rating scale, which classifies pain as mild, moderate or severe. A reduced pain rating (intensity, frequency) by the subject, ability to resume activity, increased ability to sleep, and reduced need for pain medications are indicative of analgesia.

The disclosure provides a method of treating pain in a subject in need thereof. "Treating" pain does not require a 100% abolition of pain in the subject. Any decrease in pain sensation or symptoms constitutes a beneficial biological effect in a subject. In various aspects, the method reduces severity (which can include reducing need for and/or amount of (e.g., exposure to) other drugs and/or therapies generally used for these conditions), duration, and/or frequency of pain. "Preventing" pain does not require a complete preclusion of pain sensation; any dampening or delay of the onset of pain or associated symptoms is contemplated. In this regard, optionally, the expression vector is administered to the subject prophylactically, prior to onset of pain.

Various embodiments of the disclosure allow targeting of pain transmitting somatosensory nerves (e.g., Nav1.7; Nav1.8; Nav1.9; Trk-A; 5HT; and the like) to safely produce analgesia. The method, in some aspects, minimizes or avoids unwanted off-target effects, such as indiscriminant loss of desirable somatosensory and/or motor functions associated with other parenteral (anti-NGF) or ion channel inhibitors. Optionally, the expression vector is contained within a viral capsid (e.g., viral particle) and capable of long term expression of CA10 and CA11 (or CA8), minimizing the need for repeated, invasive interventions currently required for long-term management.

The disclosure further provides use of an expression vector comprising a nucleic acid sequence encoding carbonic anhydrase 10 or carbonic anhydrase 11 (or carbonic anhydrase 8) in the treatment or prevention of pain in a subject in need thereof; use of an expression vector comprising a nucleic acid sequence encoding carbonic anhydrase 10 or carbonic anhydrase 11 (or carbonic anhydrase 8) in the preparation of a medicament for treating or preventing pain in a subject in need thereof; and an expression vector comprising a nucleic acid sequence encoding carbonic anhydrase 10 or carbonic anhydrase 11 (or carbonic anhydrase 8) for use in the treatment or prevention of pain in a subject in need thereof.

Analgesic Screening

The disclosure further provides a stock comprising a plurality of the gene transfer vectors encoding one or more candidate analgesic peptides. The stock can have any desired titer of vector, typically measured in plaque forming units (pfu) in the context of viral vectors. Typically the stock will have between about $10^5$ pfu/ml to about $10^8$ pfu/ml. In some embodiments, the stock is homogenous. In some embodiments, the DNA sequences encoding the candidate analgesic peptide(s) (or precursors thereof) differ between the vectors within the stock. In a various embodiments, respective DNA sequences encoding the candidate analgesic peptide(s) (or precursors thereof) among the vectors within the stock define a random or semi-random peptide library. Optionally, the DNA sequences encode precursors of carboxyl anhydrase peptides.

The disclosure provides a method for detecting a peptide having a desired analgesic property. A population of expression vectors described herein is introduced into a population of host cells (e.g., as NBL or HEK293 cells) under conditions suitable for expression of the encoded peptides. One or more host cells are then assayed for a desired effect representative of the desired analgesic property. If desired, the host cell(s) is assayed in comparison with a positive and/or negative control agent, such as those described herein for Car8/CA8. The control agent can be an agent known to precipitate the desired effect (positive control) or an agent known not to exhibit the desired effect (negative control). Optionally, the method further comprises deducing the DNA sequence encoding a peptide demonstrating the desired analgesic property.

The host cell(s) can be in vivo or in vitro. For in vitro applications, the assay is optionally conducted in multi-well plates (e.g., 96 well plates), which can facilitate high-throughput screening for desired pharmacodynamics and/or analgesic effect. For such applications, expression vectors from the library are optionally introduced into wells at a calculated titer of less than 1 vector per well (typically about 0.5 vectors per well) to minimize the statistical likelihood that more than one vector will transfect or infect the cells. In some embodiments, the expression vector is a viral vector, and in others, it is a plasmid or phage. Where a plasmid or phage (e.g., BAC) includes a viral genome, however, the cells within the wells will produce viral particles. Alternatively, a BAC system containing viral genomes (which comprise the respective DNA sequences and promoters) can be used to transform a larger number of cells, and viral particles rescued. The resultant viral particles then can be used in the assay. For example, if about 10,000 BACs containing HSV backbones that carry the random or semi-random library are introduced into host cells in a 6-well dish, after about 24 hours, about 100,000 viral particles typically can be harvested. These can be employed in the assay. Desirably, about 30,000 viral particles should be used (about three times the number of original vectors) to increase the likelihood that all members of the library are being assayed. The desired effect to be assayed can be any suitably measurable effect, such as apoptosis, antagonism of ITPR1 activation and calcium release or other aspects of this cell signaling pathway, etc. Exemplary assays and methodologies are provided in the Example, which should not be construed to be limiting.

In some embodiments, the host cell(s) are in vivo (i.e., an animal model), which is particularly suitable when the desired effect to be assayed is behavioral in nature. For example, an analgesic effect can include a decrease in hyperalgesia or allodynia brought on by, for example, an external stimulus or a medical condition. In such embodiments, the library can be clonally expanded into a plurality of random stocks of vectors (each of which is substantially homologous), and the respective stocks introduced into an animal model of pain. The vector DNA from those stocks, which decrease the pain response in the animal, can then be sequenced to identify the encoded analgesic peptide.

Formulations, Administration Regimens

In various aspects, the expression vector is provided in a composition (e.g., a pharmaceutical composition) comprising a physiologically-acceptable (i.e., pharmacologically-acceptable) carrier, buffer, excipient, or diluent. Any suitable physiologically-acceptable (e.g., pharmaceutically acceptable) carrier can be used within the context of the disclosure, and such carriers are well known in the art. The choice of carrier will be determined, in part, by the particular site to which the composition is to be administered and the particular method used to administer the composition. The composition also can comprise agents, which facilitate uptake of the expression vector into host cells. Suitable composition formulations include aqueous and non-aqueous solutions, isotonic sterile solutions, which can contain antioxidants, buffers, bacteriostats, and solutes that render the formulation isotonic with the blood, and aqueous and non-aqueous sterile suspensions that can include suspending agents, solubilizers, thickening agents, stabilizers, and preservatives. The composition can be presented in unit-dose or multi-dose sealed containers, such as ampules and vials, and can be stored in a freeze-dried (lyophilized) condition requiring only the addition of the sterile liquid carrier, for example, water, immediately prior to use. A composition comprising CA8-, CA8 fragment-, CA10- or CA11-encoding expression vectors is, in one aspect, placed within containers, along with packaging material that provides instructions regarding the use of the composition. Generally, such instructions include a tangible expression describing the reagent concentration, as well as, in certain embodiments, relative amounts of excipient ingredients or diluents (e.g., water, saline or PBS) that may be necessary to reconstitute the composition.

In various embodiments, the expression vector is incorporated into lipid vesicles (which optionally enhances uptake) or provided in the form of a nanoparticle (e.g., by incorporation with a protein, lipid, carbohydrate, or combination thereof). Physical bombardment may be utilized to increase vector uptake by cells. Optionally, the expression vector is provided with chemical-based transduction enhancers. An example of a transduction enhancer includes lipoplex technology, wherein positively charged DNA is combined with anionic and neutral lipids to construct lipoplexes to enhance uptake. Polyplexes represent another form of chemical delivery complex for expressing units. In general, polyplexes consist of cationic polymers, and fabrication is based on ionic interactions and self-assembly. Another example, cationic liposomes, interact with cell membranes to enhance uptake through endocytosis. To improve transfection efficiency, electro-neutral lipids, such as DOPE are added to enhance release into the cytoplasm and escape lysosomal degradation. In another embodiment, polymersomes are used as an alternative to liposomes. Polymersomes are synthetic versions of liposomes (vesicles with a lipid bilayer) that tend to be more stable than liposomes, mechanically stronger, and have a longer storage self-life. Endosome-lytic agents include inactivated adenovirus that facilitate nanoparticle escape from the endocytic vesicle made during uptake.

Due to their low toxicity, greater carrying capacity, and ease of fabrication, polycationic nanoparticles are an advantageous embodiment. Polyethyleneimine and chitosan are among the polymeric carriers suitable for expression vector delivery. Other polycationic carriers include poly (beta-amino esters) and polyphosphoramidate. Dendrimers are highly branched macromolecules with a spherical shape useful in aiding the cellular targeting of expressing units.

One embodiment includes the use of cationic dendrimers. These molecules naturally attract negatively charged genetic material such as DNA or RNA and this complex is taken into the target cells via endocytosis. Recently, dendrimers have been produced using kinetically driven chemistry that reduces cost and process time. "Priostar" dendrimers can carry a variety of expressing units including DNA or RNA and efficiently transfect target cells at a high efficiency with little or no toxicity.

Inorganic nanoparticles, such as gold, silica, iron oxide, and calcium phosphates represent another chemical means to deliver nucleic acid to target cells. Benefits of inorganic nanoparticles include stable prolonged storage, low cost manufacturing, minimal immunogenicity, and resistance to microbial attack. Nano-sized inorganic particles (e.g., less than 500 nm, preferably less than 250 nm, and most preferred less than 100 nm) represent another option for enhancing transduction, if desired. The nanoparticles can efficiently trap DNA or RNA and allow escape from the endosome without degradation.

Cell-penetrating peptides, also termed peptide transduction domains (PTDs), are short peptides (<40 amino acids) that efficiently pass through cell membranes while being covalently or non-covalently bound to various expressing units, facilitating their entry into cells. PTDs can be constructed to release exogenous nucleic acid to specific cell organelles by incorporating localization peptide sequences.

Some well-known physical methods of delivery of expressing units to target cells include the use of electroporation, sonoporation (ultrasonic frequencies to cavitate membranes making them more permeable to the expressing unit entry), magnetofection (expressing unit is complexed with magnetic particles enhancing the entry into target cells with a magnet), and hydrodynamic methods.

In various embodiments, the expression vector is incorporated into a viral capsid (viral particles) representing an infectious viral particle (including capsid, single or double stranded DNA, RNA, or other nucleic acid capable of coding for necessary peptide(s)), which can be advantageous to support latent infection and stable long-term analgesic peptide production. Peptide expression may be intracellular, and impact neuronal excitability and functioning in a way that produces analgesia or anti-hyperalgesia.

The expression vector (e.g., viral particle) is administered in an amount and at a location sufficient to provide some improvement or benefit to the subject, i.e., diminish or inhibit the sensation or perception of pain in the subject. Depending on the circumstances, a composition comprising the expression vector is applied or instilled into body cavities, applied directly to target tissue, and/or introduced into circulation. For example, in various circumstances, it will be desirable to deliver the composition comprising the expression vector by intravenous, intraperitoneal, intra-oral; intra-luminal (e.g., urinary bladder, gall bladder, bile ducts, pancreatic ducts, or sinus); intramuscular, intra-ocular, transcorneal, intraarterial, intraportal, intralesional, intradermal, intraarticular, intraneuronal, intraganglion, periganglion, intra-dermal, transdermal, subcutaneous, intraperitoneal, intranasal, inhalation (e.g., upper and/or lower airways), enteral, vaginal, or rectal means. In various aspects, the expression vector is administered directly to the pancreatic ducts, which is useful for, e.g., treating pain associated with pancreatic cancer or pancreatitis). In various aspects, the expression vector is administered to the trigeminal ganglia. If desired, the expression vector is administered regionally via intraarterial or intravenous administration feeding the region of interest. In various aspects, the expression vector described herein is administered directly or indirectly to peripheral somatosensory nerves. In one embodiment, the route of administration involves direct administration (e.g., injection or infusion) to dorsal root ganglion, other ganglia or somatosensory neurons, or the spinal cord. Optionally, the expression vector is administered via intra-articular injection or peripheral (e.g., sciatic) nerve injection. In various aspects, the expression vector is administered by intra-articular insertion to treat chronic nociceptive pain by, e.g., quieting the somatosensory nerves supplying an affected arthritic joint. In other embodiments, the expression vector is administered to various cavities, ducts, sinuses, or organs via a microcatheter or with direct visualization using an endoscope. Other embodiments include the use of needles to facilitate localization of expression vector to regions of pain. For example, the disclosure contemplates administration of the expression vector to sites (e.g., organ or other bodily site, such as joint) where pain arises using a catheter or needle. Still other embodiments include the use of imaging to guide the deposition of expression vector using for example, fluoroscopy, ultrasound, CT or MRI. A further embodiment includes the use of formulations that facilitate the delivery of expression vector via intradermal routes and to the gut by avoiding degradation in the stomach or upper gastrointestinal track.

In various aspects, enteric-coated encapsulation may be used to prevent degradation by gastric acid and inactivation of an expression vector. A formulation may include incorporation of a capsule composed of enteric-coated granules developed using Eudragit L30D-55 as a enteric polymer encasing expression vectors. Optimization of the capsule formulation may be achieved with an optimal protective coating with Eudragit L30D-55 demonstrating maximum viable vector count after two hours of incubation in acid medium and disintegration time of one hour in buffer pH 6.8. The amount of Eudragit L30D-55 in the capsules correlates with gastric juice resistance. Protective qualities against artificial gastric juice are observed when capsules were prepared from granules composed of vectors, corn starch, lactose monohydrate, polyvinylpyrrolidone and coated with 12.5% (m/V) of Eudragit L30D-55. Other coatings may be used to provide enteric-protective properties of a commercially available polymer EUDRAGIT®L100-55 on gelatin capsules and also on DRcaps®. Still other enteric coatings include, e.g., Vcaps® (Lonza) enteric coated capsules incorporating a polymer blend that enables effective delayed release, gastric protection, and protection of compounds with mild-to-moderate acid sensitivity; and enTRinsic Drug Delivery Technology incorporating capsule technologies described as a polymer blend that provides enteric protection to small and large molecules that are highly acid-sensitive.

Still other embodiments to provide gastric resistance to labile vectors can be also obtained by adding enteric polymeric systems to other dosage forms. Tablets, mini-tablets, pellets and granules (usually filled into capsule shells) are the most common enteric-coated dosage forms utilizing polymers noted elsewhere.

In various aspects, the expression vector is injected into a peripheral nerve (e.g., sciatic, femoral, infraorbital, trigeminal, facial, or suprascapular) or via intra-ganglion injection. In other embodiments, the expression unit may be a naked single or double stranded DNA expression unit that is circular and resistant to nuclease destruction. In other embodiments, the vector may be incorporated into lipid vesicles for better absorption. Still other embodiments include single or double stranded DNA expressing units that are incorporated into a protein, lipid, carbohydrate molecules, or combinations of these as nanoparticles. Still other embodiments include physical methods of entry into target cells. An exemplary embodiment includes the use of chemical methods to enhance the uptake of expression vector entry into target cells. Other embodiments utilize a combination of physical, chemical, and biological methods for enhanced uptake of expression vectors into target cells.

Alternatively, the composition is administered locally via implantation of a membrane, sponge, or another appropriate material onto which the composition has been absorbed or encapsulated. Where an implantation device is used, the device is, in one aspect, implanted into a suitable tissue, and delivery of the expression vector is, for example, via diffusion, timed-release bolus, or continuous administration.

A particular administration regimen for a particular subject will depend, in part, upon the amount of therapeutic administered, the route of administration, and the cause and extent of any side effects. The amount administered to a subject (e.g., a mammal, such as a human) in accordance with the disclosure should be sufficient to affect the desired response over a reasonable time frame. In various embodiments of the method of treating or preventing pain in a subject, an expression vector encoding CA8 (or Car8), CA8 (or Car8) fragments (including CA8-204, CA8-204$^C$, CA8-204$^G$, CA8-202 and CA8-203), CA10 (or Car10) or CA11 (or Car11) is administered in an amount to induce analgesia. Put another way, the dose of composition administered is sufficient to reduce, ease, suppress, or alleviate pain. Exemplary doses of viral particles in genomic equivalent titers of $10^4$-$10^{15}$ transducing units (e.g., $10^7$-$10^{12}$ transducing units), or at least about $10^5$, $10^6$, $10^7$, $10^8$, $10^9$, $10^{10}$, $10^{11}$, $10^{12}$, $10^{13}$, $10^{14}$, or $10^{15}$ transducing units or more (e.g., at least about $10^7$, $10^8$, $10^9$, $10^{10}$, $10^{11}$, $10^{12}$, $10^{13}$ or $10^{14}$ transducing units, such as about $10^{10}$ or $10^{12}$ transducing units). Some conditions require prolonged treatment, which may or may not entail multiple administrations over time. Equivalent doses of vectors in genomic equivalents are $10^4$-$10^{15}$, which can be quantified in vitro using quantitative PCR (qPCR) in term of expressing units (wherein an expressing unit is a discrete genetic unit capable of producing one peptide described herein). In various aspects, the dose comprises $10^7$-$10^{12}$ expressing units, or at least about $10^4$, $10^5$, $10^6$, $10^7$, $10^8$, $10^9$, $10^{10}$, $10^{11}$, $10^{12}$, $10^{13}$, $10^{14}$, or $10^{15}$ expressing units or more (e.g., at least about $10^7$, $10^8$, $10^9$, $10^{10}$, $10^{11}$, $10^{12}$, $10^{13}$, or $10^{14}$ expressing units, such as about $10^{10}$ or $10^{12}$ expressing units).

When appropriate, the expression vector comprising a nucleic acid encoding CA8, CA8 fragment (including CA8-204, CA8-204$^C$, CA8-204$^G$, CA8-202 and CA8-203), CA10 or CA11 (or mouse versions thereof) is administered in combination with other substances (e.g., therapeutics) and/or other therapeutic modalities to achieve an additional (or augmented) biological effect. This aspect includes concurrent administration (i.e., substantially simultaneous administration) and non-concurrent administration (i.e., administration at different times, in any order, whether overlapping or not) of the expression vector and one or more additionally suitable agents(s). It will be appreciated that different components are, in certain aspects, administered in the same or in separate compositions, and by the same or different routes of administration.

According to a further aspect of the disclosure there is provided the use or method according to any other aspect of the invention wherein the CA8, CA8 fragment (including CA8-204, CA8-204$^C$, CA8-204$^G$, CA8-202 and CA8-203), CA10 or CA11 vector is administered separately, sequentially or simultaneously in combination with one or more agents useful for pain management. Examples of further agents include, but are not limited to, an opioid analgesic (e.g., morphine, hydromorphone, oxymorphone, fentanyl, codeine, dihydrocodeine, oxycodone, or hydrocodone); a nonsteroidal antiinflammatory drug (NSAID) (e.g., aspirin, diclofenac, ibuprofen, naproxen, oxaprozin, or cyclooxygenase-2 (COX-2) inhibitor); a sedative (e.g., a barbiturate sedative); a muscle relaxant; an antidepressant; an anticonvulsant (e.g., carbamazepine or valproate); an additional anesthetic; and a corticosteroid (e.g., dexamethasone).

The invention, thus generally described, will be understood more readily by reference to the following example, which is provided by way of illustration and is not intended to limit the invention.

EXAMPLES

Example 1

This example demonstrates that carbonic anhydrase-8 (CA8 human gene symbol, Car8 rodent ortholog); carbonic anhydyrase-10 (CA10 human gene symbol; Car10 rodent ortholog), and carbonic anhydrase-11 (CA11 human gene symbol; Call rodent ortholog), regulate the ITPR1-cytosolic free calcium-signaling pathway. ITPRs are believed to transduce signals arising from metabotropic receptor activation that generate inositol 1,4,5-trisphosphate (IP3) signaling molecules and intracellular calcium release from ITPRs, which play an important role in inflammatory pain behaviors. Zhuang et al., PLoS One, 2015. Data described herein for the first time show that CA8/Car8), CA8/Car8 fragments (including CA8-204); CA10/Car10, and CA11/Car11 function to inhibit IP3 activation of the ITPR1 calcium release channel, intracellular calcium release, and, surprisingly, inhibit analgesic responses to therapeutic analgesics (e.g., morphine and clonidine) by inhibiting intracellular calcium release, yet these CA peptides produce profound analgesia and treat or prevent chronic neuropathic pain in models. Also surprisingly, CA8/Car8 fragments (including CA8-204) and CA10/Car10 do not bind to ITPR1 (as demonstrated by co-immunoprecipitation); yet, in distinct contrast to CA8 (Car8) peptides, intracellular overexpression of CA8/Car8 fragments (including CA8-204) and CA10/Car10 peptides inhibit ITPR1 activation (phosphorylation) in response to forskolin and ATP-stimulated intracellular calcium release.

Additionally, data provided herein demonstrate for the first time that overexpression of CA8 selectively inhibits nerve growth factor (NGF) that signals nearly exclusively in NBL cells through ITPR1 as shown by near complete 2-APB. CA8 also inhibits NGF-induced ITPR1 activation (pITPR1), intracellular calcium release. Surprisingly, CA8 (Car8) DRG overexpression also is demonstrated herein to prevent and treat chronic neuropathic pain after spinal nerve (SNL) root injury. The following Examples establish that DRG CA8 (Car8) and CA10 (Car10) transduction and overexpression of the CA8 (Car8) and CA10 (Car10) protein down regulates ITPR1 activation (e.g., pITPR1 at Ser-1755) and inhibits intracellular calcium release. Surprisingly, despite the lack of amino acid homology between CA8 and CA10 (Car10) proteins, they also produce profound analgesia after sciatic nerve injections preventing mechanical allodynia and thermal hyperalgesia in chronic inflammatory and neuropathic pain models (spinal nerve ligation (SNL)).

Morphine produces analgesia by triggering the release of intracellular calcium. The data provided herein demonstrate that CA overexpression inhibits morphine induced ITPR1-mediated calcium release in NBL cells. Specifically, these data show that DRG Car levels are related to the half-maximal morphine and clonidine analgesic response. Higher Car expression is associated with higher morphine and clonidine half-maximal analgesic doses (Levitt et al., 2017). These data suggest for the first time that CAs may induce analgesic tolerance shifting the dose-response to clonidine and morphine to the right (e.g., higher doses of analgesic are required to produce the same amount of analgesic response), and these effects are related to inhibition of intracellular calcium release. This is unexpected, given that morphine requires intracellular calcium release to produce an analgesic response. Thus, it is surprising that CAs produce profound analgesia, instead of producing nociceptive pain by inhibiting the calcium regulatory pathway required for opioid and clonidine analgesic response.

Materials and Methods

Animals: All experiments and procedures were performed according to the current guidelines for investigator of experimental pain in conscious animals, and were approved by the Animal Care and Use Committee of the University of Miami. Male adult C57BL/6 mice weighting 20-35 grams were obtained from Jackson Laboratories (Bar Harbor, ME) and were kept in a home cage environment with access to food and water ad libitum. Animals were housed in a 12-12 h light-dark cycle in a virus/antigen-free facility with controlled humidity and temperature. Animals were allowed to acclimatize for 7 days before surgery and familiarize with the experimental equipment before testing.

Generation of viral constructs: As an example, a methods of generating adeno-associated vectors expressing mouse or human V5-Car10 or V5-CA10 proteins is described. Car10 (mouse) and CA10 (human) cDNA were purchased from ATCC. These gene products were amplified by Eppendorf Recycler gradient (Model 5331) and cloned between the BamHI and XhoI (NEB) restriction sites of the pcDNA3.1/V5-His A (Invitrogen™ Life Technologies, Carlsbad, CA) using the forward primer: TTTGGATCCGCCAC-CATGGCT-GACCTGAGCTTCATTG and the reverse primer: TTTCTCGAGCTGAAAGGCCGCTCGGA-TG. The V5-Car10 or V5-CA10 constructs were then amplified from pcDNA3.1/V5-His A and cloned between the BamHI and BglII restriction sites of the pAAV-MCS vector, one component of AAV Helper-Free System (Agilent Technologies, SalI ta Clara, CA) using the forward primer: CTCG-GATCCGCCACCATGGC and the reverse primer: CTCG-GATCCGCCA-CCATGGC.

Recombinant AAV8-V5-Car10 and AAV8-V5-CA10 viral particles were produced. Briefly, the vector plasmids, and the packaging plasmid AAV8 733(5) and pHelper (Agilent Technologies, SalI ta Clara, CA) were co-transfected into HEK293 cells at 70% confluence using calcium phosphate precipitation method. The cells were incubated for 48 hours at 37° C. and 5% $CO_2$. After 48 hours, the cells were collected and freeze-thawed three times to release the AAV particles from the cells. After 30 min of Benzonase® Nuclease (Sigma) treatment, the crude lysate was clarified by low speed centrifugation. The supernatant was loaded on discontinuous iodixanol step gradients in OptiSeal™ tubes (Beckman Coulter) and centrifuged in a Type 70 Ti rotor (Beckman Coulter) at 69,000 rpm (350,000 g) for 1 h at 18° C. The fraction containing AAV particles was collected and further purified using an AKTA FPLC system (GE Healthcare) by column chromatography on a 5 ml HiTrap column (GE Healthcare). About 25 mL was eluted from the column using elution buffer (20 mM Tris, 215 mM NaCl, pH 8.0), and the AAV particles were concentrated and buffer exchanged to 200 µl in HBSS (Invitrogen) using an Amicon Ultra-15 50K concentrator (Millipore). The purified AAV particles were then titrated for genome contents (expressing units) using qPCR methods. Titers in the range $1-3 \times 10^{14}$ GC (Genome Copy) per mL were obtained.

Cell culture and transfections: Human neuronal-derived (e.g., NBL), human non-neuronal derived (e.g., HEK293) cells, or dispersed rodent primary DRG cells can be used. HEK293 cells (cat #CRL-1573 ATCC Manassas, VA) were cultured in Dulbecco's modified Eagle's medium (DMEM-Glutamax cat #0566; Invitrogen) supplemented with 10% fetal bovine serum, FBS (cat #16140 ThermoFisher scientific, Waltham, MA) and 1% penicillin/streptomycin (cat #15140 ThermoFisher scientific, Waltham, MA). Cells were seeded in six-well plates at density of $1.0 \times 10^5$ cells per well. The following day, cells were transfected with plasmids via lipofectamine LTX reagent and plus (cat #15338 ThermoFisher scientific, Waltham, MA). For each transfection 2 µg of AAV2-ITR (control), AAV2-V5-Car10, or AAV2-V5-CA10 vectors was used. In various embodiments of the disclosure described herein, 2 µg of expression vectors (including positive and negative controls) in instances when AAV2 is not the viral vector employed.

Sciatic nerve injection of expression vectors (adeno-associated AAV8-V5-Car10 and AAV8-V5-CA10 vectors): Mice were anesthetized by intraperitoneal injection of Ketamine, xylazine and acepromazine cocktail (VEDCO, Saint Joseph, MO). Following sciatic nerve exposure, about 1.5 µl viral particles of AAV8-null ($1.36E^{13}$ viral particles, SL100832 SignaGen Laboratories Rockville, MD), AAV8-V5-Car10 and AAV8-V5-CA10 ($1.06E^{14}$ viral particles and $1.66E^{14}$ viral particles, respectively) were injected into the sciatic nerve using a 35-gauge Nanofil needle (World Precision Instruments, Sarasota, FL). The sciatic injection site was approximately 45 mm from the tip of the third toe.

Inflammatory hyperalgesia models: Mice received a 30 µl intradermal injection of 1% carrageenan (cat #22049 Sigma, St Louis, MO) 2.5 mg/ml in sterile 0.9% saline or complete Freund's adjuvant, CFA (cat #F5881 Sigma, St Louis, MO) 0.5 mg/ml in sterile 0.9% saline into the left hind paw. Fehrenbacher et al., Curr Protoc Pharmacol. 2012; Chapter 5:Unit 54.

Neuropathic pain model: For the induction of peripheral neuropathy, mice were first anesthetized by an intraperitoneal injection of ketamine, xylazine hydrochloride and acepromazine (VEDCO, Saint Joseph, MO). Then, a tight ligation of the spinal nerve (left L5 in mouse model) was performed using a previous described procedure. Kim et al., Pain. 1992; 50(3):355-363.

Behavioral tests: Thermal and mechanical sensitivity was measured by Hargreaves test and von Frey filament threshold calculations respectively. See, e.g., Boyce-Rustay et al. Methods Mol Biol. 2010; 617:41-55; Hargreaves et al., Pain. 1988; 32(1):77-88; and Chaplan et al., J Neurosci Methods. 1994; 53(1):55-63. Tests were performed in a quiet room with daylight-like illumination. Animals were habituated to the behavioral room and apparatus for at least 60 minutes for 1 week before a blinded investigator collected data. The thermal sensitivity test was performed using an IITC Plantar Analgesia Meter apparatus (IITC Life sciences, Woodland Hills, CA) with a plastic box placed on a glass plate of constant temperature (30° C.). The mouse plantar surface was exposed to a beam of radiant heat to induced paw withdrawal. Baseline latencies were adjusted to 5-9 sec with a maximum of 20 sec as cutoff to prevent potential injury. The latency time in seconds from the onset of the intense light beam to paw withdrawal was defined as the withdrawal latency of the paw. Two consecutive tests were averaged to establish the paw withdrawal latency. The mechanical sensitivity test was performed in an inverted plastic box placed on an elevated mesh floor. The mouse hind paw was pressed with one of a series of von Frey filaments with logarithmically incrementing stiffness (Stoelting Co, Wood Dale, IL) presented perpendicular to the plantar surface of each hind paw for 1-2 seconds, the 50% threshold was determined using the Up- and Down method.

Pharmacodynamics—Bioassay of Calcium Release: Fifteen mm glass coverslips (cat #72228 Electron Microscopy Sciences, Hatfield, PA) were coated with poly-D-Lysine (Sigma) followed by Laminin and 1×105 cells were seeded on each coverslip. Twenty-four hrs later, cells were transfected with AAV2-ITR, AAV2-V5-Car10, or AAV2-V5-CA10 vectors as previously described. In embodiments wherein AAV2 is not employed, other expression vectors (including viral vectors) are used. Fura-2AM (cat #F1221 ThermoFisher scientific, Waltham, MA) was dissolved in DMSO (50 µg in 50 µl) and 1% pluronic acid-127 (cat #P2443 Sigma, St Louis, MO) as the stock solution. Forty eight hrs after seeding, cells were loaded with 2 µM Fura-2AM dye for 45 min at room temperature in the dark in a standard Ca+2 buffer solution containing: 125 mM NaCl, 2 mM MgCl, 4.5 mM KCl, 10 glucose, 20 mM HEPES, 2 mM CaCl2, pH 7.4.25. Following dye loading, coverslips were washed with $Ca^{+2}$ buffer solution. For imaging and ATP stimulation experiments, coverslips were placed in a recording chamber (cat #QR-42LP Warner instruments Hamden, CT) on a Leica DMI6000B microscope, and perfused at room temperature (~22° C.) with $Ca^{+2}$ free buffer solution containing: 125 mM NaCl, 4 mM MgCl, 4.5 mM KCl, 10 mM glucose, 20 mM HEPES, pH 7.4. For the ratiometric imaging of Fura-2AM, the excitation light was filtered through an ultra high-speed wavelength switcher to provide wavelengths of 340 and 384 nm and capture by a high-speed digital camera (Leica DFC365FX). Activation of ITPR1 channels was achieved via application of 1 μM ATP (Sigma, St Louis, MO). Data acquisition and processing was made using the LAXS software. Regions of interest over the field of view were selected and the mean pixels intensity at each frame was measured. Data was plotted as ratio fluorescence intensity versus time and subsequently converted to a relative scale.

Immunoprecipitation: Fifty μl magnetic beads (Invitrogen) were incubated with 1 μg pITPR1 antibody for 45 minutes at 4° C. The supernatant was discarded and the beads were washed with binding buffer. Sample proteins of 200-400 μg were added and incubated with the beads for 4 hrs at 4° C. Then the protein complex was washed 3 times with washing buffer, and then eluted with SDS sample buffer. Samples were then heated at 70° C. for 10 min and then subjected to western blot analysis for Car10. The method described herein also is suitable for use in connection with Car8, CA8, CA8 fragment (CA8-204), CA10, Car11 and CA11.

Immunohistochemistry (IHC): HEK293 cells were seeded in poly-L-Lysine/laminin coated glass coverslips at a density of per coverslip, 24 hrs later cells were transfected with Car10, CA10 or empty vector respectively. Cells were cultured at 37° C. for an additional 96 hrs, then treated with forskolin 1 μM (F6886 Sigma, St. Louis, MO) for 5 min, then fixed with 4% paraformaldehyde for 15 min, permeabilized with 0.1% Triton X-100 for 10 min, and blocked with 1% bovine serum albumin (BSA, sigma) for 1 h. Cells were then incubated with anti-pITPR1 (cat #8548s cell signaling technology), anti-Car10 (cat #SAB1102286 Sigma, St Louis, MO), anti-V5 (cat #R960 Invitrogen), anti-ITPR1 (cat #8568 Cell Signaling technology) antibody overnight at 4° C. The next day, cells were incubated with the corresponding second antibody (1:200) for 1 h at room temperature in the dark. Coverslips were dried and affixed to slides using a fluorescent mounting medium containing Dapi (cat #P36931 Life Technologies). It will be understood that IHC methods also are contemplated using anti-Car8, anti-CA8, anti-CA8 fragment (CA8-204), anti-CA10, anti-Car11 and anti-CA11 antibodies.

Statistical analysis: Data was expressed as means±standard error of the mean (SEM) and analyzed for statistical significant by Student's t test for two-group comparison, one-way ANOVA with Bonferroni's post hoc test for multiple comparison (three or more groups) with one variance, and two-way ANOVA with Bonferroni's post hoc test for multiple comparisons (three or more groups) with two variances. All data analysis and graphics were performed using the GraphPadPrism 5.0 software (GraphPad Inc, SalI Diego, CA).

Pharmacodynamics: Bioassays of Electrophysiology Impact of Viral Constructs—validation of reduced neuronal excitability in vitro: Neurons and other transfected cells are studied in current clamp, perforated whole-cell configuration of the patch-clamp technique, at room temperature (20-25° C.). Perforation is obtained by amphotericin B to ensure satisfactory current clamp recordings, while maintaining intact cytosolic calcium concentration and pertinent cytosolic signaling apparatus in each cell population to be studied. Patch micropipettes (resistances 3-6 M) are pulled and polished, as described previously. Sarantopoulos C, et al., J Neurosci Methods. 2004; 139(1):61-8; Sarantopoulos C, et al., Reg Anesth Pain Med. 2002; 27(1):47-57; Kawano T, et al., Mol Pain. 2009; 5:12; Sarantopoulos C D, et al., Brain Res. 2007; 1132(1):84-99; Hogan Q H, et al., Pain. 2000; 86(1-2):43-53. For recordings, a Multiclamp 700 B amplifier is used (Axon Instruments, Foster, CA, USA), and signals are digitized using a converter (DigiData 1440 A; Axon Instruments). The pCLAMP software (Axon Instruments) is used for analysis. Whole cell current clamp recordings are conducted using extracellular Tyrode's solution, and internal pipette solution, as described previously. Excitability parameters are compared between groups of cells classified by expression parameters. Recordings from cell populations differing by expression patterns (e.g., TrkA or Nav1.8 positive and negative), size (large vs. small DRG somatosensory neurons), and excitability differ depending on the viral vector are used. The following parameters are compared between groups: (1) Resting membrane potential (RMP) recorded at baseline for at least 3 min and spontaneous electrical activity (number of spontaneous action potential (AP) spikes/min). RMP for further comparison are determined after stable recording is established for at least 1 min. Neurons with a resting potential more depolarized than −45 mV, indicating large leak current, are rejected. (2) AP is evoked in response to supra-threshold stimulation by current injection. The current threshold is determined by sequential 25 pA step increments until a monomorphic AP is triggered, and each threshold will be recorded. Then, an AP is elicited by a single, 2 ms supra-threshold current pulse, and captured in subsequent recordings lasting 500 ms (to measure both AP and after-hyperpolarization (AHP) parameters). (3) Characteristics of AP are measured and compared between groups including RMP, peak AP amplitude, AP threshold and AP duration at threshold, as well as at 5% and 50% amplitude. AP threshold is measured at the beginning of the sharp upward rise of the depolarizing phase. AP is also measured from the point where a horizontal diachronic line is drawn from this AP threshold to the point where the descending, repolarizing phase crosses this line. AP amplitude is measured from RMP to the AP peak. AP duration is determined at a voltage 5% from RMP to the AP peak, as well as at the midpoint of 50% voltage from RMP to peak. AP magnitude is also expressed as area under the curve. AHP amplitude is measured from the RMP to the most hyperpolarized level of the AHP phase. AHP duration is measured at points representing 50% and 90% recovery back to RMP. AHP magnitude is also expressed as area under the curve. Two other measures of cell excitability are used including: rheobase (which is determined as the minimum current amplitude in a gradually stepwise increasing series of depolarizing 200-ms pulses that elicits an AP) and the pattern of AP spike generation during current injection steps of at least twice that of rheobase, at which cells either produce single APs or fire repetitively.

HSV TrkA and Nav1.8 Promoters Drive Robust Long Term Reporter Expression: Virus only reaches DRG cell bodies via retrograde transport in vivo. Since these are rdHSV, they cannot infect nearby glia or other DRG cells that don't project to the local injection site. After 30+ days, strong expression is observed from both the LAT and ICP4 loci in rodents. The ICP4 locus increases with time, which is why it was chosen as the site for the expression cassettes (TrkAp-CA, Nav1.8p-CA, Advillinp-CA, etc.). If, for example, sufficient expression in neurons is not demonstrated, or if expression decreases with time, expression cassettes can be relocated in the LAT locus.

Pharmacokinetics: Dose Response and Tissue Specificity—Structural and functional validation in vivo: Analgesia and motor function testing include measures of mechanical pain (von Frey), thermal pain (Hargreaves), and non-reflexive sensory and motor functions (voluntary wheel running using automated measures: wheel distance/time, wheel time; and stride). Eighteen naïve male C57BL/6J mice per assay condition is used. The initial time course of analgesic response is monitored every other day until D14 and then weekly until D28 (end-of-life point). Clinical safety assessments are made at baseline and weekly in each mouse (e.g., body wt., general appearance, food consumption, blood pressure, body temperature). Restricted neuronal expression is assessed as in these preliminary studies in skin, peripheral nerves, DRG and dorsal horn (DH) using qPCR (region) and immunohistochemistry (IHC) (cell subtype).

Assessing routes of administration: In various aspects, the expression vector is administered via direct sciatic and femoral nerves (SFN) or intra-articular (IA) injections. Biological response achieved using these routes is compared response achieved using intradermal administration. Direct sciatic nerve injections achieve profound analgesia by transduction of lumbar DRG. Sensory innervation of major joints is accessible through direct IA injection. DRG transduction is achieved with this approach, which offers rapid adoption by clinical experts, ease of access, and potentially adequate viral infectivity of all disease-affected dermatomes. While direct peripheral nerve blocks with radiofrequency ablation are easily achieved as an alternative using traditional techniques for some major joints (e.g., knee via genicular blocks, shoulder via suprascapular nerve blocks); peripheral nerve blocks for pain relief of other joints are not feasible (e.g., temporomandibular, hip, ankle, elbow, wrist, etc.). Currently, there are very limited options to treat temporomandibular joint disease (TMJ) pain; intra-articular injection of the expression vector described herein represents a transformational therapy for control of symptoms.

All measures are by individuals masked to treatment. Animals are randomly assigned to groups. Assays are conducted at approximately the same time of day. Routine clinical safety assessments are made (e.g., body wt., general appearance, food consumption, pulse, blood pressure, body temperature). The highest achievable dose (PFU) is used for SFN and IA injections and a series of dilutions (up to ten thousand fold) to optimize subsequent parameters for all expression vectors. Eighteen-naïve male C57BL/6J mice/ group are used. Analgesic response is monitored every other day until D14 and weekly thereafter until D28 (end-of-life) (analgesia, antihyeralgesia to mechanical and thermal evoked responses; automated voluntary running wheel (wheel distance/time, wheel time, wheel speed; stride). Additionally, clinical safety assessments at baseline and weekly are made in each mouse (e.g., body wt., general appearance, food consumption, blood pressure, body temperature). Restricted neuronal expression is assessed in peripheral nerves, DRG and DH using QPCR (region) and IHC (cell subtype with double staining). Direct DRG transduction may also be achieved using transforaminal epidural injection.

Figure 7:
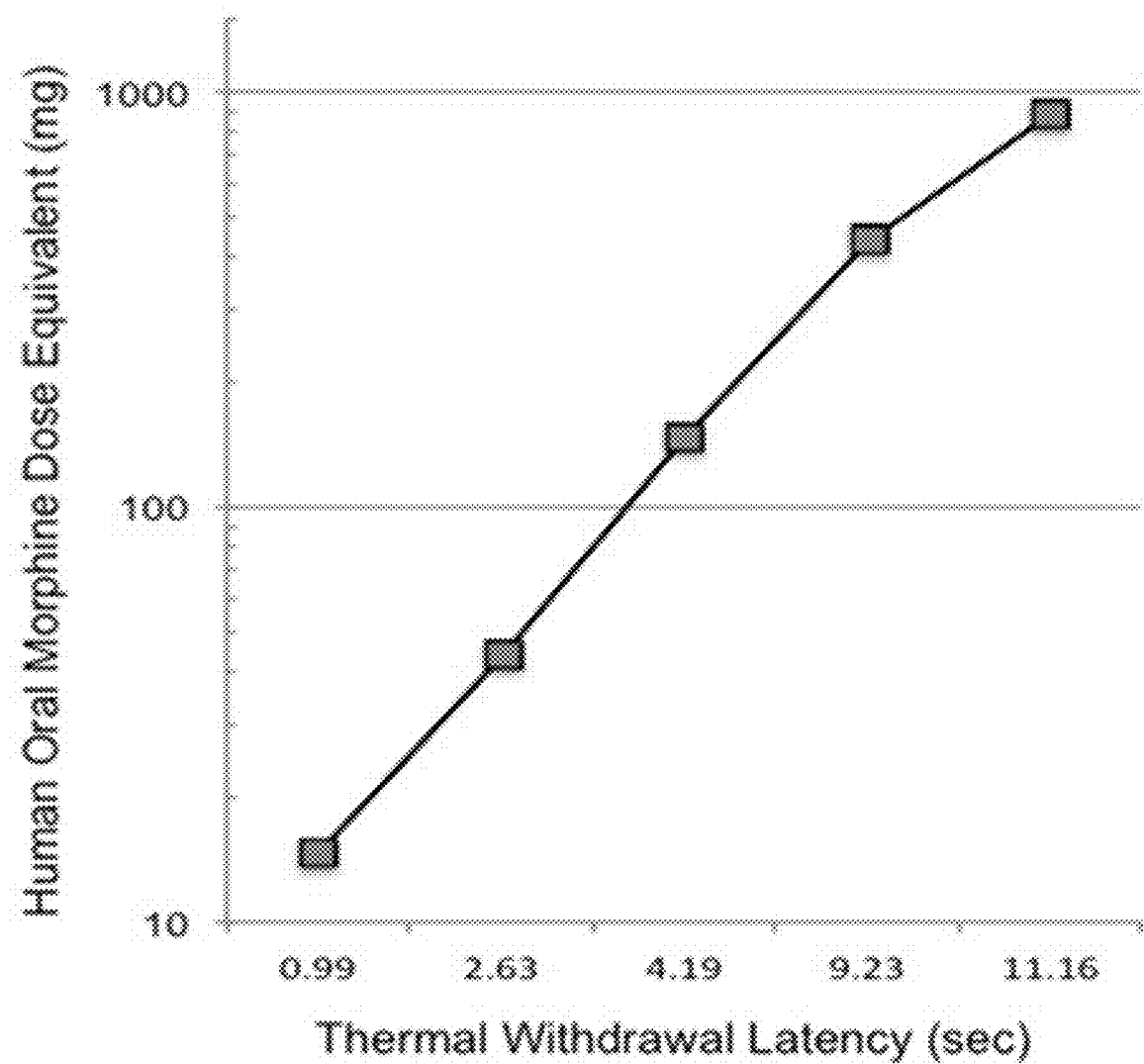
FIG. 7 is a graph illustrating the relationship between paw withdrawal latency (seconds) (x-axis), to morphine equivalents oral dose in a 60 kg human (intraperitoneal dosing assessed at approximately 30 minutes after dosing; data are extrapolated to human equivalent dosing using allometric conversion) (y-axis). The elevations in the paw withdrawal latency after transfer of V5-Car10 and V5-CA10 produces profound analgesia in these mouse models as described in FIGS. 2 through 5 when compared to the human oral equivalent dose.
Figure 11:
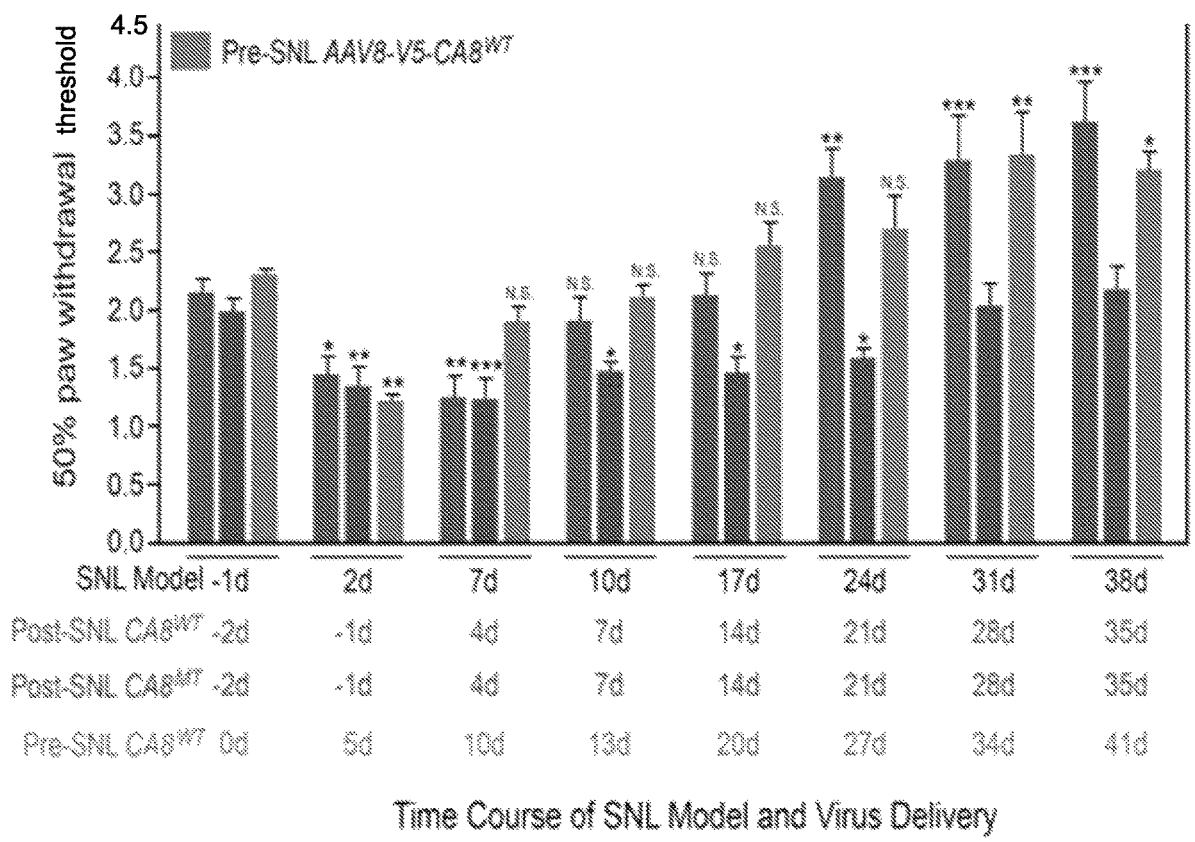
FIG. 11 is a bar graph illustrating paw withdrawal latency (seconds) (y-axis) on various days of study (x-axis), demonstrating the analgesic effect of expression of V5-CA8WT (left bar=post-SNL CA8WT; right bar=post-SNL CA8WT) and V5-CA8MT (CA8MT represents the S100P point mutation that destabilizes the protein and leads to rapid degradation by the proteasome; Turkmen S, et al., PLoS Genet 5, e1000487) (center bar=post-SNL CA8MT) in a neuropathic (Chung) mouse pain model. Mechanical withdrawal thresholds are shown following sciatic nerve injections of AAV viral particles (approximately $1.0 \times 10^{14}$ viral particles) in C57BL/6J mice. AAV8-V5-CA8WT increased mechanical withdrawal thresholds above baseline (analgesia) by Day 7 after administration, and this was maintained through Day 38 despite spinal nerve ligation on Day 3. There was no similar increase in withdrawal thresholds after administration of an expression vector encoding of AAV8-V5-CA8MT. (N=8. * $p<0.05$,  $p<0.01$, * $p<0.001$, by two way ANOVA followed by Bonferroni test). The results of the study are surprising. First, it was unclear whether CA8 would function against the mouse ITPR1 target. These data show human proteins function in mouse cells/tissue; and that in vitro bioassays described herein can be used to test pharmacodynamics of CA analgesic peptides and variants. Additionally, neuropathic pain is believed to arise from different mechanisms than inflammatory pain. Moreover, medications that work well for inflammatory pain do not produce anti-hyperalgesia or anti-allodynia in neuropathic pain models. Surprisingly CA8 is effective in preventing and treating neuropathic pain.
Figure 12A:
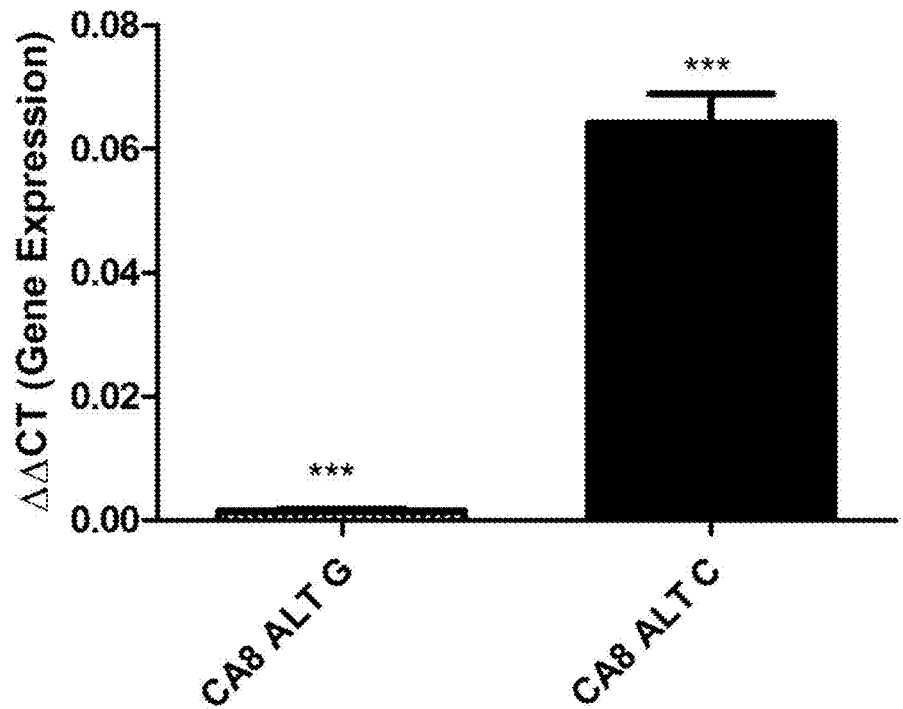
FIG. 12A is a bar graph illustrating gene expression for CA8 fragments encoded by the first three exons of the CA8 coding sequence: an alternative splice fragment "CA ALT G" ("G" allele at SNP rs6471859) and wildtype CA8 "CA ALT C" (C allele for SNP rs6471859) as measured by qPCR in NBL cells. The wildtype CA8 splices normally, and NBL cells produce this fragment encoded by the first three exons of CA8, almost exclusively. Expression of the "G" allele at SNP rs6471859 leads to alternative splicing, and there is almost no detectable CA8-204 product with an extended exon three with a retained intron in NBL cells. Thus, essentially all CA8 transcript and protein fragment encoded by the first three exons of CA8 is produced and stable in NBL cells.
Figure 12B:
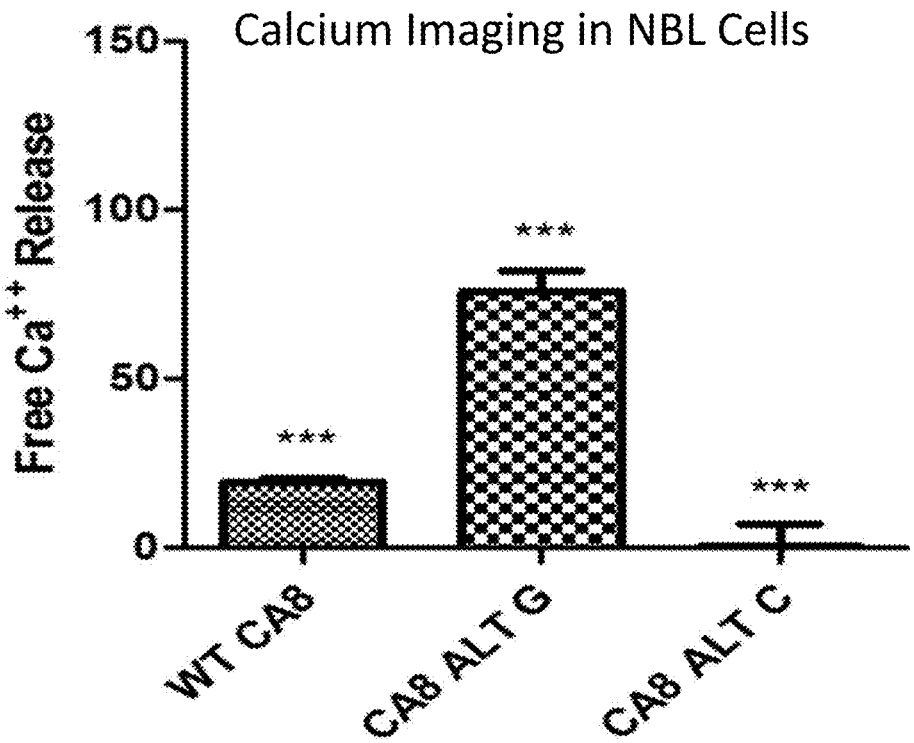
FIG. 12B is a bar graph demonstrating that this CA8 fragment (encoded by the first three exons only) inhibits ATP-stimulated calcium release in NBL cells. The wildtype CA8 (C allele for SNP rs6471859) splices normally, and this fragment of the wildtype gene product is produced in NBL cells. Expression of the "G" allele at SNP rs6471859 leads to alternative splicing, and production of CA8-204 protein is minimal in NBL cells. This fragment mediates no inhibition in these cells as compared to the vectors expressing CA8-201 (wildtype protein, left bar) or the truncated CA8 fragment produced by the "C" allele (right bar).
Figure 13A:
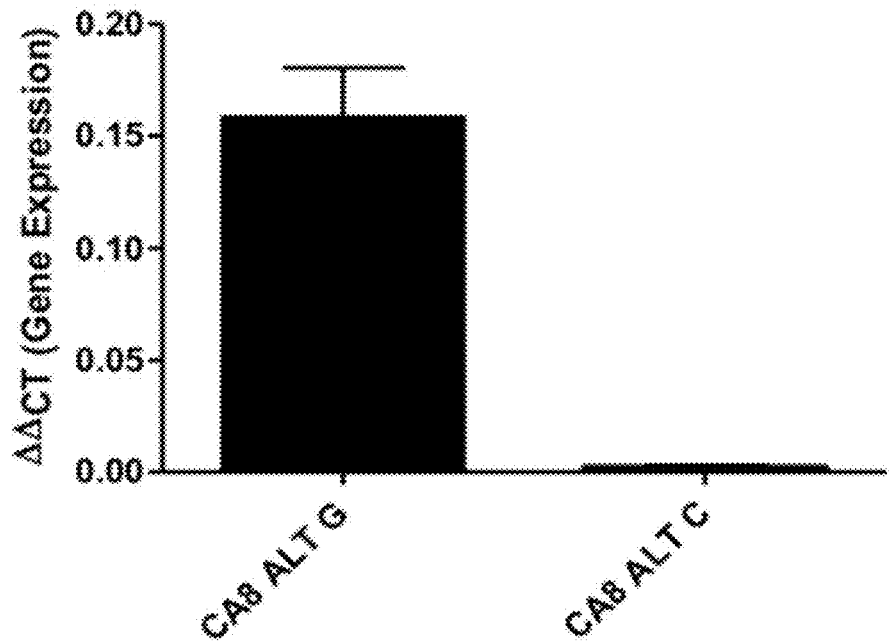
FIG. 13A is a bar graph illustrating expression of CA8 fragments in HEK293 cells as measured by qPCR. Expression of the "G" allele at SNP rs6471859 leads to alternative splicing in these cells, producing the CA8-204 product with an extended exon 3 with a retained intron in HEK293 cells (left bar). There is essentially no detectable wildtype CA8 (C allele for SNP rs6471859) in HEK293 cells (right bar), which produces a fragment corresponding to the first three exons of CA8. Thus, essentially all vector expression in HEK293 cells is the CA8-204 alternative transcript.
Figure 13B:
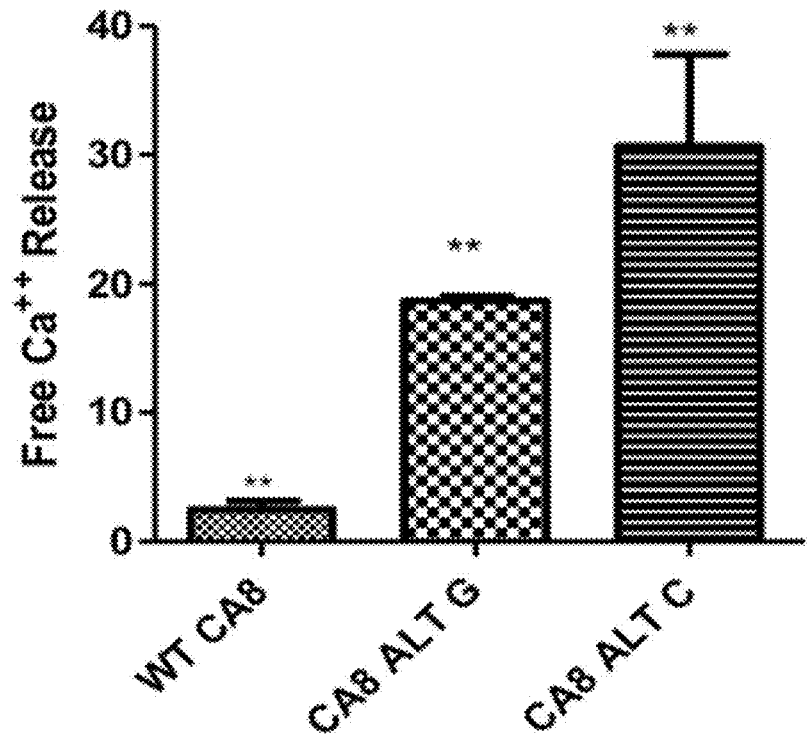
FIG. 13B is a bar graph demonstrating that CA8-204 inhibits ATP-stimulated calcium release in HEK293 cells. The vector expressing the "G" allele at SNP rs6471859 leads to alternative splicing and production of CA8-204 protein found in HEK293 cells, which inhibits ATP-induced calcium release compared to the vectors expressing wildtype CA8 (CA8-201) and the fragment coded for by the "C" allele.
Figure 14:
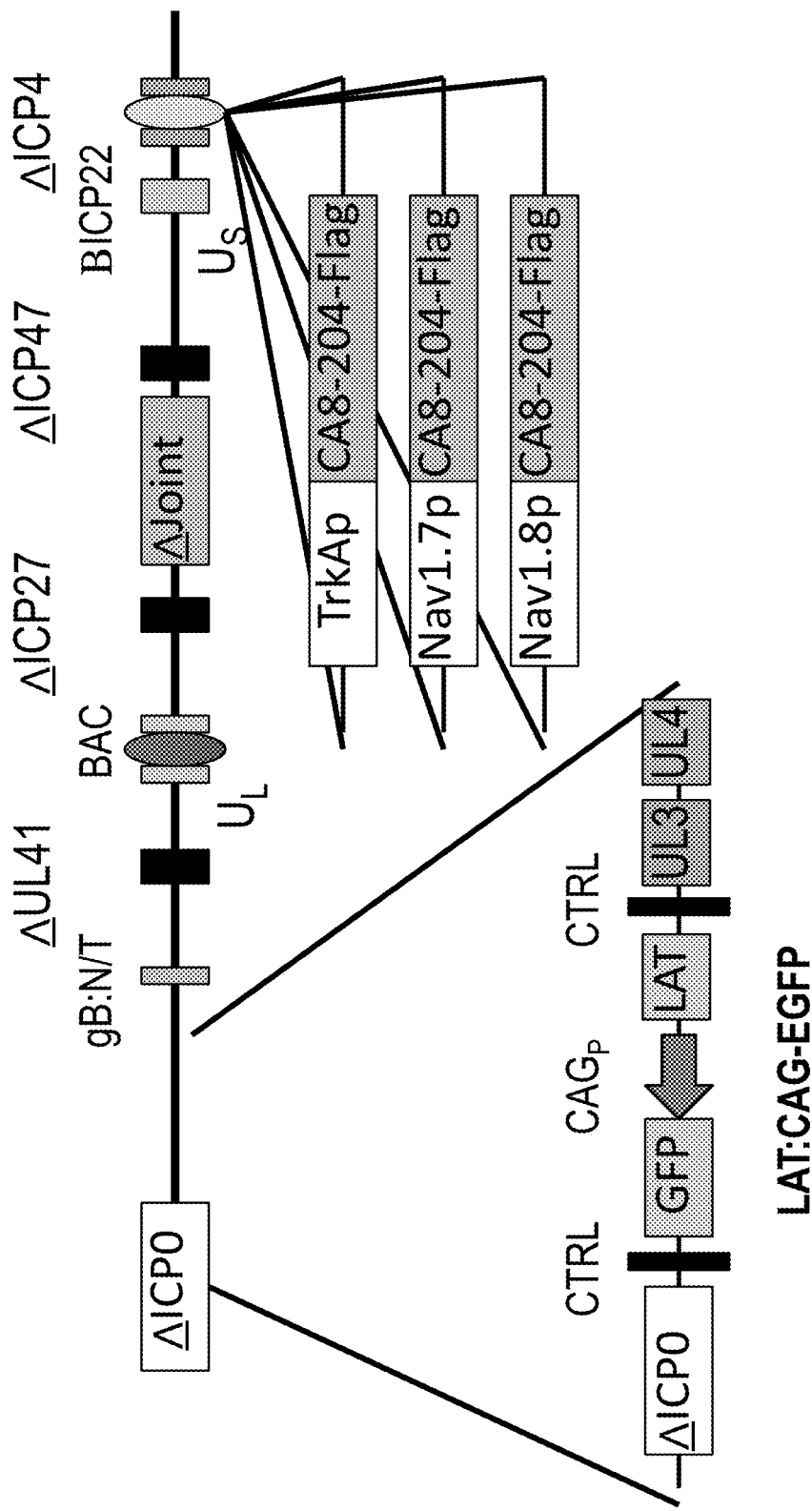
FIG. 14 is a diagram of an exemplary HSV expression vector for CA8 delivery. TrkAp-CA8-Flag, Nav1.7p-CA8-204-Flag, Nav1.8p-CA8-204-Flag, and (not shown) Tet-Advillin-CA8-204-Flag) cassettes may be incorporated into the ICP4 locus. The base vector is optionally deleted for ICP0, ICP4 IE regulatory genes, Joint region, ICP27, ICP47, ICP22 IE genes "TAATGARAT", and the UL41 vhs gene. A gB:N/T mutation may be present (which in various embodiments enhances cell entry), and BAC sequences are located between loxP sites in intergenic regions. The vector construct is also suitable for delivery of CA8 fragments.
Figure 15:
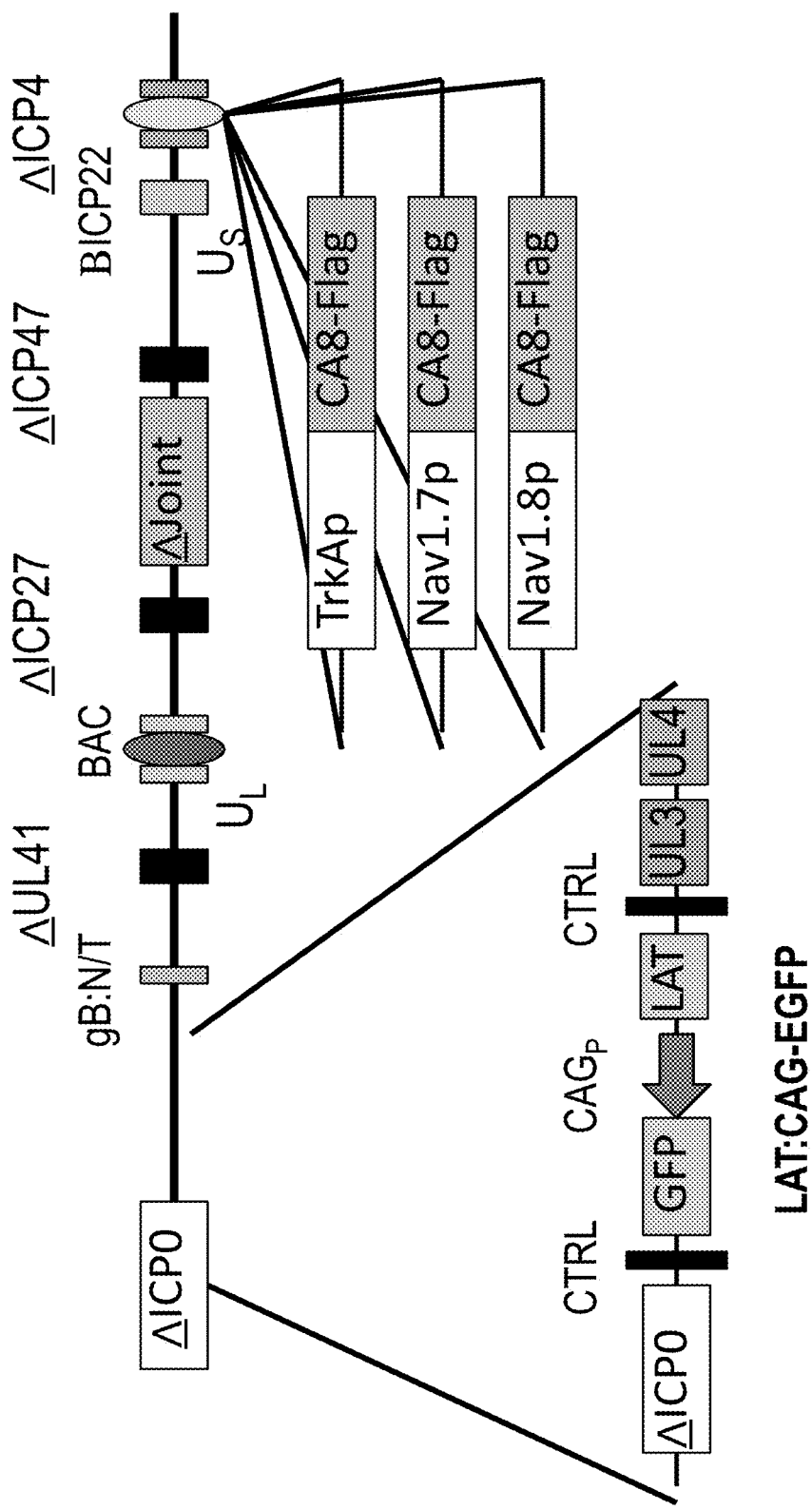
FIG. 15 is a diagram of an exemplary HSV expression vector for CA8 delivery. TrkAp-CA8-Flag, Nav1.7p-CA8-Flag, Nav1.8p-CA8-Flag, and (not shown) Tet-Advillin-CA8-Flag cassettes may be incorporated into the ICP4 locus. The base vector is deleted for ICP0, ICP4 IE regulatory genes, Joint region, ICP27, ICP47, ICP22 IE genes "TAATGARAT"; and UL41 vhs gene. A gB:N/T mutation enhances cell entry, and BAC sequences are located between loxP sites in intergenic regions.
Figure 16:
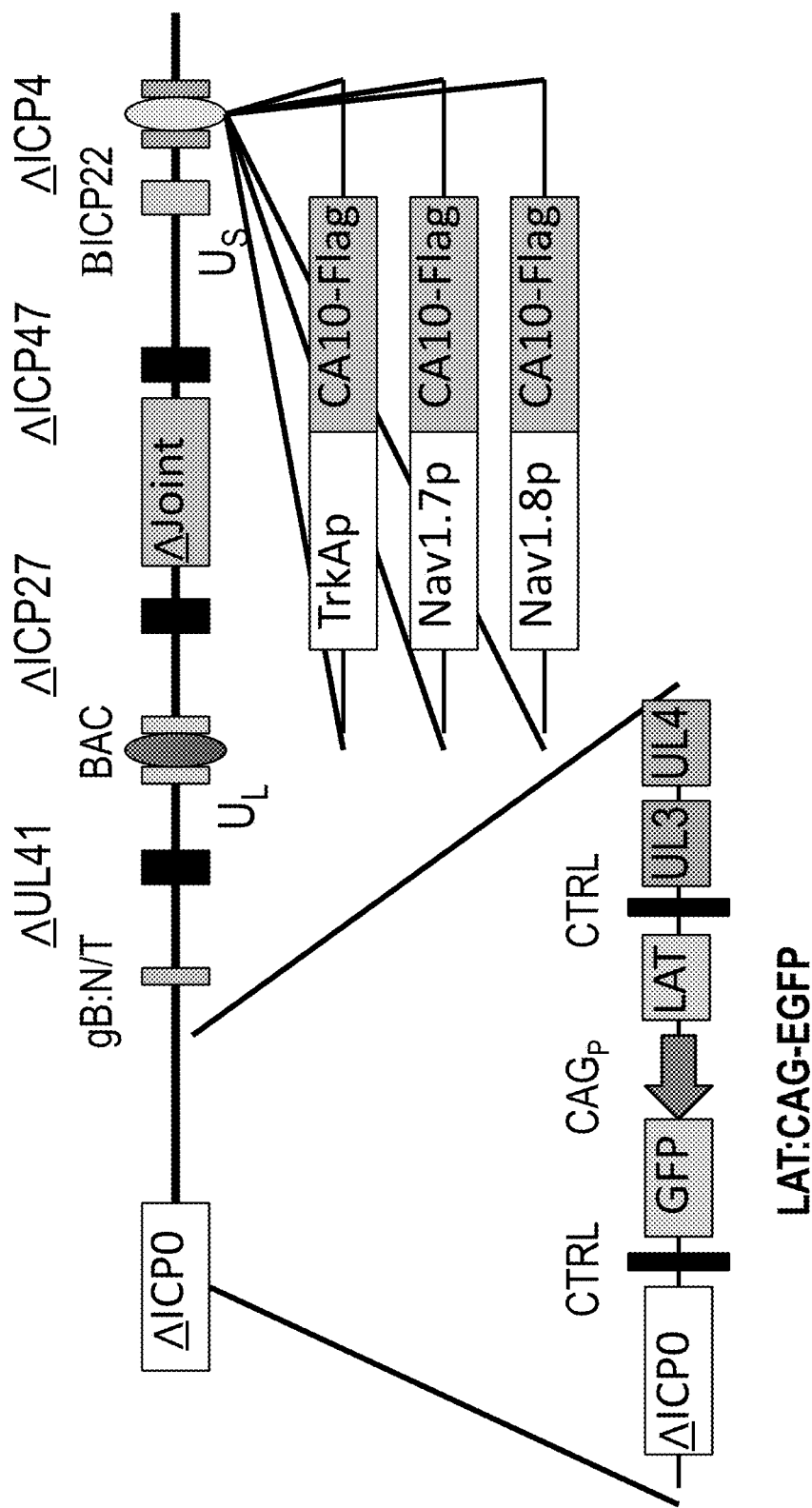
FIG. 16 is a diagram of an exemplary HSV expression vector for CA10 Biotherapeutic delivery. Diagram of TrkAp-CA10-Flag, Nav1.7p-CA10-Flag, Nav1.8p-CA10-Flag, and (not shown) Tet-Advillin-CA10-Flag cassettes may be incorporated into the ICP4 locus. The base vector is deleted for ICP0, ICP4 IE regulatory genes, Joint region, ICP27, ICP47, ICP22 IE genes "TAATGARAT"; and UL41 vhs gene. A gB:N/T mutation enhances cell entry, and BAC sequences are located between loxP sites in intergenic regions.
Figure 17:
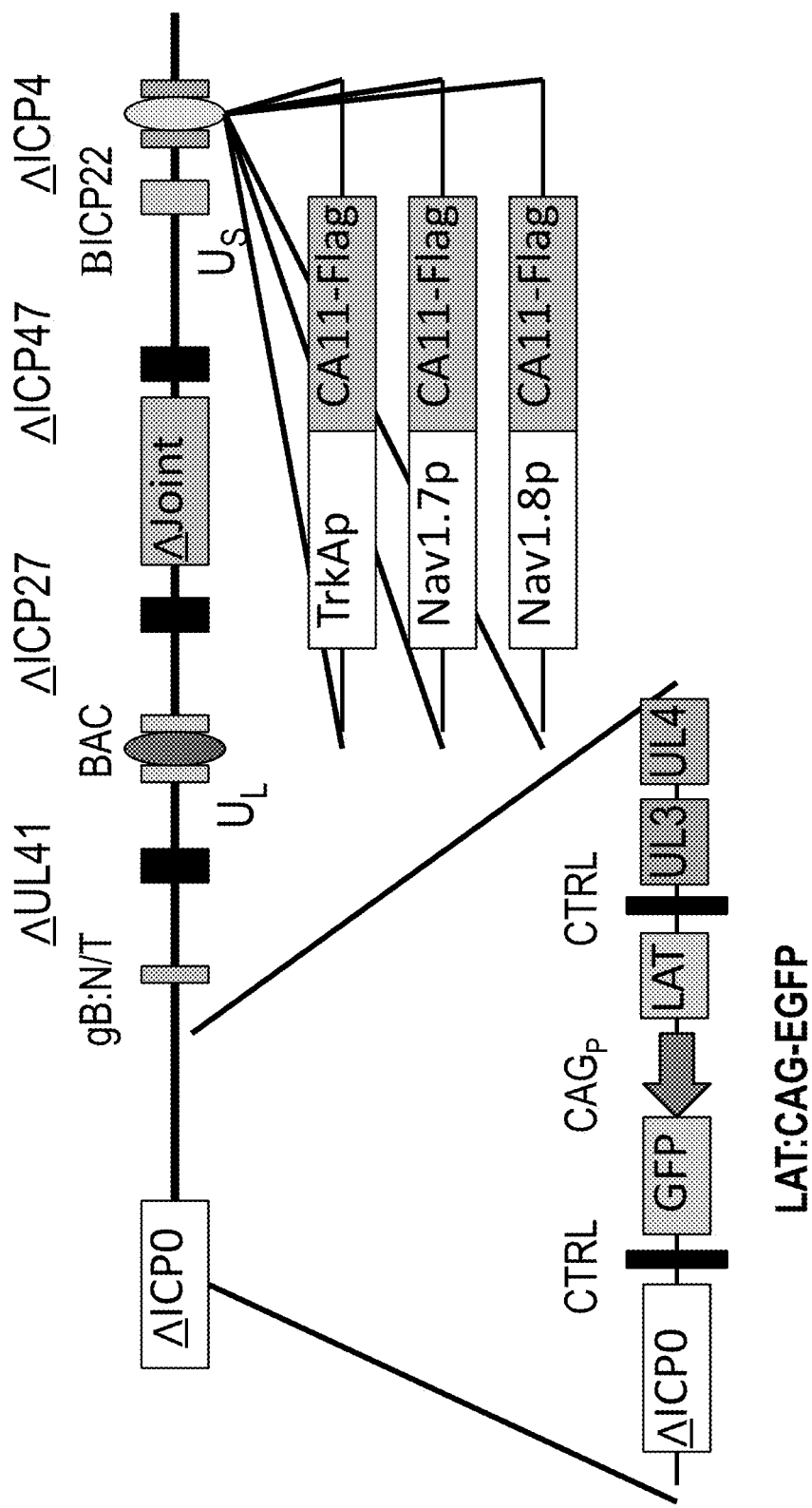
FIG. 17 is a diagram of an exemplary HSV expression vector for CA11 delivery. TrkAp-CA11-Flag, Nav1.7p-CA11-Flag, Nav1.8p-CA11-Flag, and (not shown) Tet-Advillin-CA11-Flag cassettes that represent inducible promoter systems may also be incorporated into the ICP4 locus. The base vector is deleted for ICP0, ICP4 IE regulatory genes, Joint region, ICP27, ICP47, ICP22 IE genes "TAATGARAT"; and UL41 vhs gene. A gB:N/T mutation enhances cell entry, and BAC sequences are located between loxP sites in intergenic regions.
Figure 18:
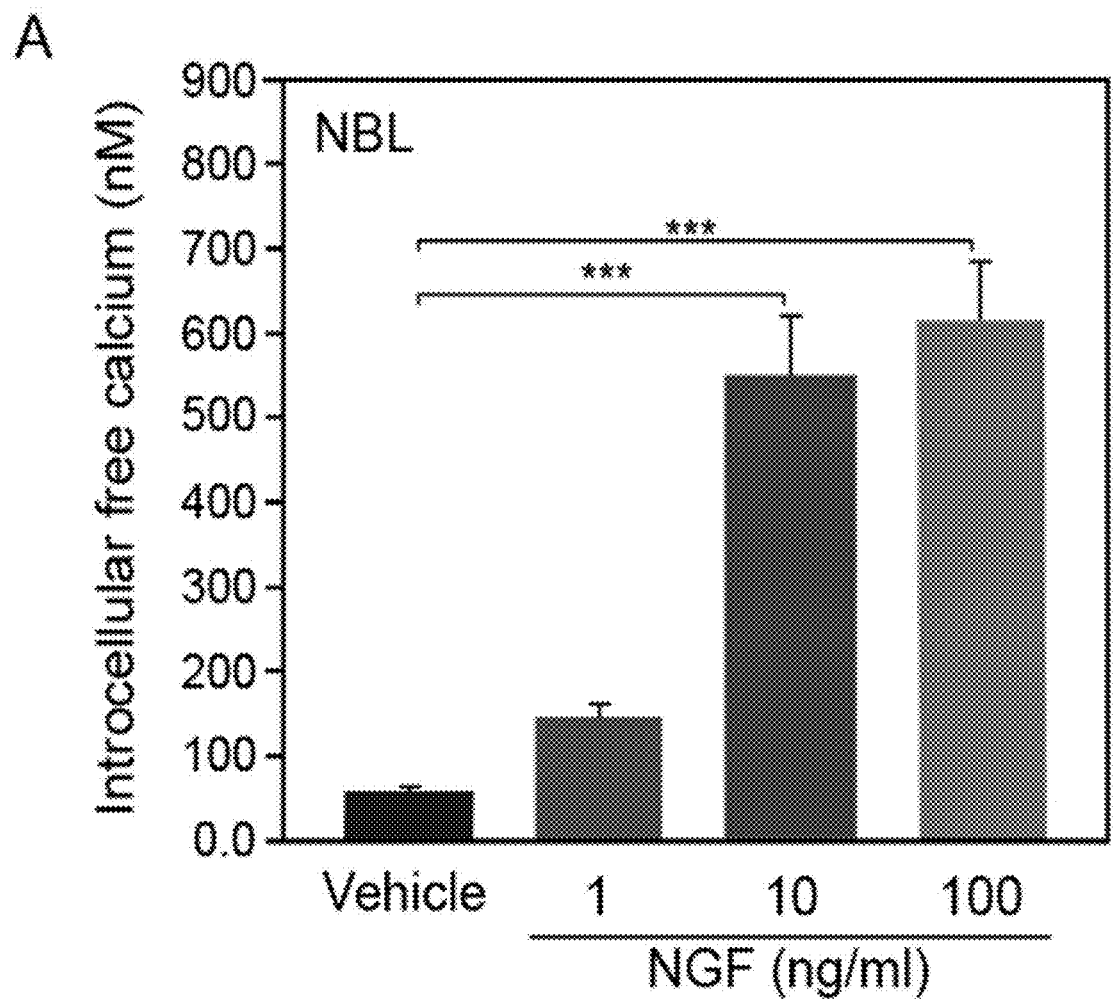
FIG. 18 is a bar graph illustrating NGF-induced intracellular calcium release (y-axis) in NBL cells in response to various doses of NGF (1, 10, 100 ng/mL) (x-axis). HEK293 cells also respond to NGF with increased intracellular calcium release (data not shown).
Figure 19:
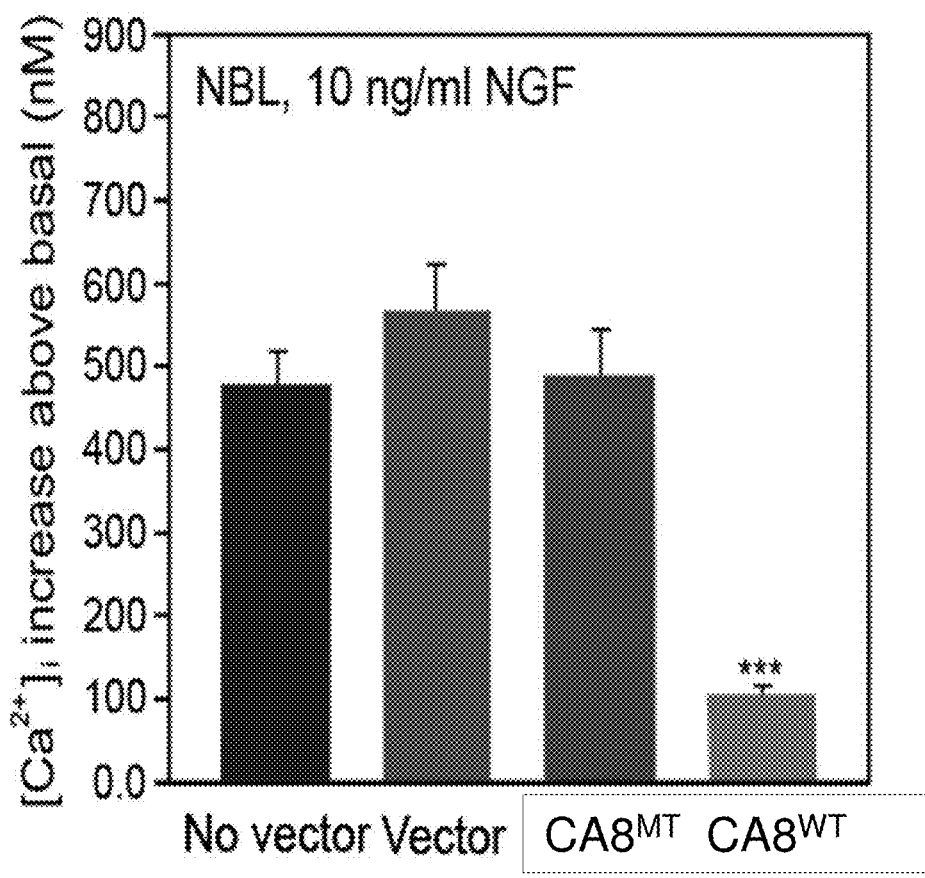
FIG. 19 is a bar graph illustrating that NGF-induced intracellular calcium release (y-axis) in NBL cells is nearly completely by overexpression of wildtype CA8, but not overexpression of a mutant form of CA8. ATP induced intracellular calcium release is also inhibited by CA10 overexpression [data not shown].
Figure 20:
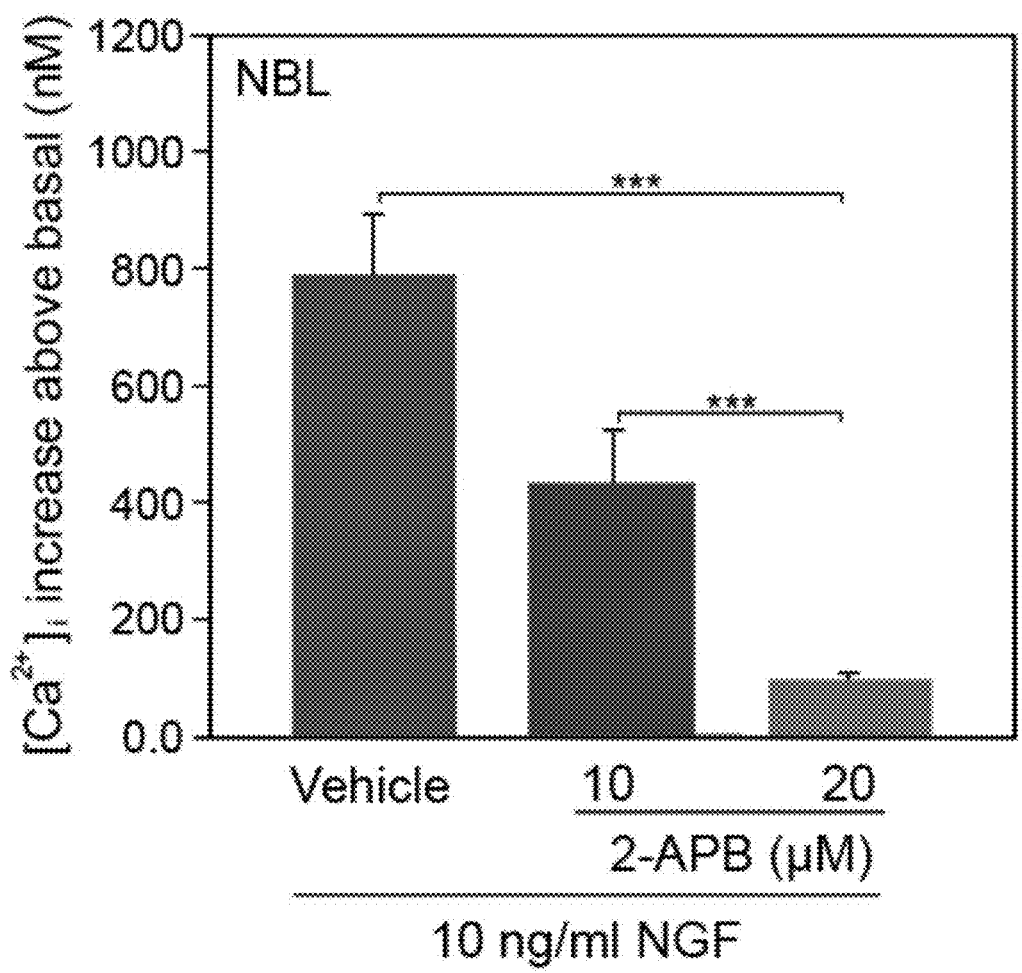
FIG. 20 is a bar graph illustrating blockage of NGF-induced intracellular calcium release by the selective ITPR1 inhibitor 2-APB in NBL cells. Thus, NGF signaling in NBL cells is almost exclusively through ITPR1 and nearly completely inhibited by this ITPR1 selective inhibitor. Similar inhibition by 2-APB was also observed in HEK293 cells [data not shown].
Figure 21A:
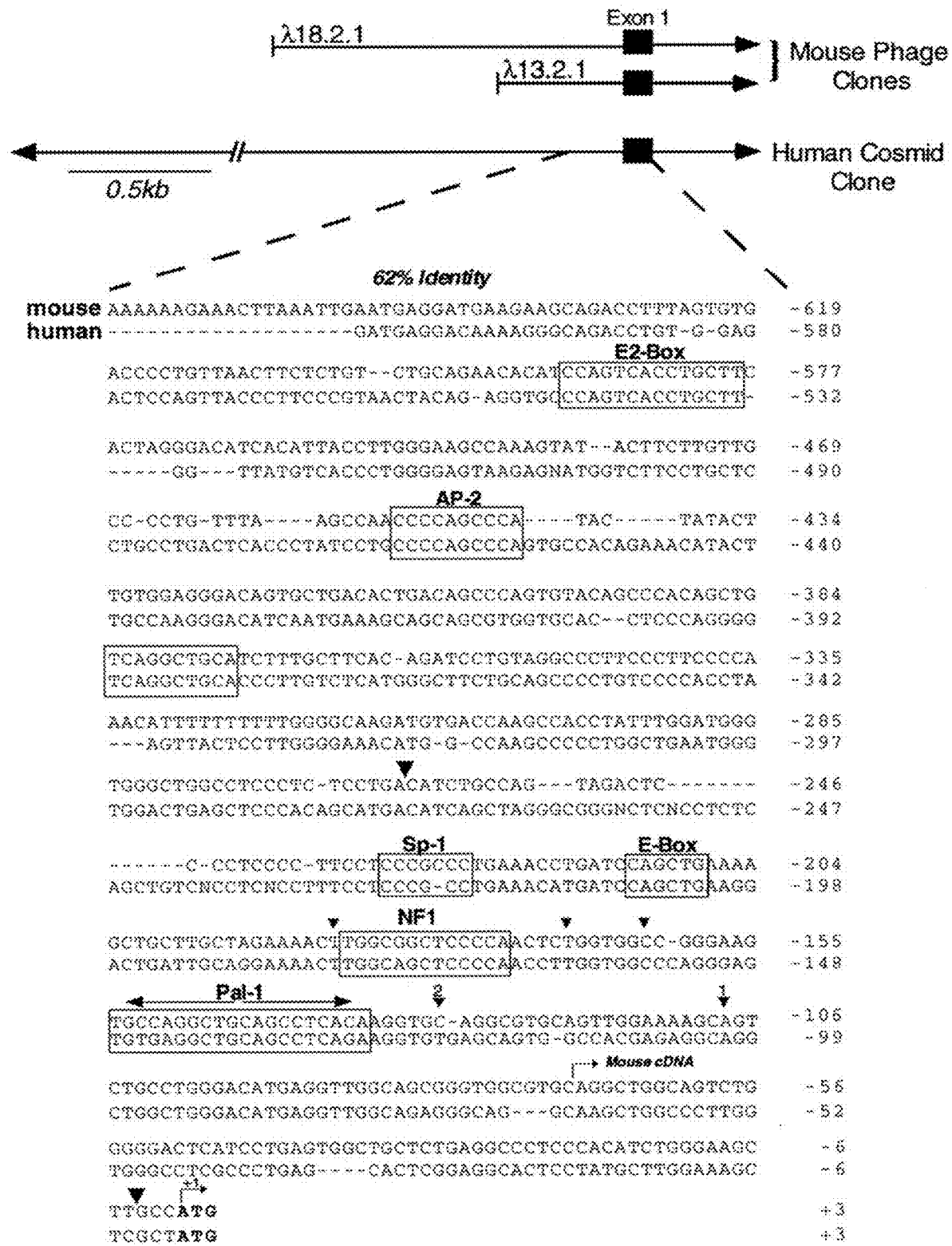
FIG. 21A is a schematic of the 5HT-3 receptor promoter and comparison of mouse (SEQ ID NO: 14) and human sequences (SEQ ID NO: 15) (Journal of Neuroscience 15, August 1998, 18(16) 6186-6194).
Figure 27A:
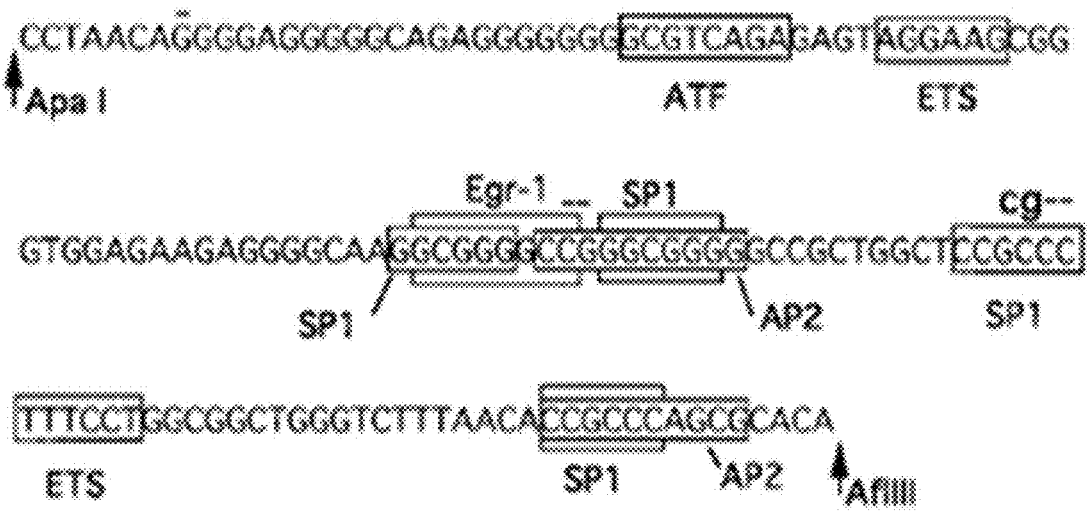
FIG. 27A provides the sequence of human Trk-A promoter (SEQ ID NO: 25) (J. Biol. Chem. 1998, 273:39-44). Potential DNA binding protein binding sites are marked by boxes.

Pharmacodynamics: Bioassays of Analgesia and Antihyperalgesia: Both chronic inflammatory and chronic neuropathic pain models are employed. These studies include protection (prevention) trials for CFA (expression vector injected prior to pain) and protection and treatment trials for SNL and OA (expression vector is injected after the nerve injury occurs and assessed over time). Direct sciatic nerve injection prevents and treats chronic neuropathic pain in the SNL model (see FIG. 7). Preliminary short and long-term safety-related-to-mechanism studies and off-target toxicity may be performed in two models. All measures are recorded individuals masked to treatment. Animals are randomly assigned to groups. Assays will be conducted at approximately the same time of day. Clinical pathology, gross inspection, organ weights, and histopathology will be assessed; and CA8, CA8-204, CA10, CA11, ITPR1, pITPR1 measured using DRG, spinal cord, CSF and blood. DRG neuronal and glial apoptosis is examined. In addition to efficacy assessments, clinical safety assessments are made (e.g., body wt., general appearance, food consumption, blood pressure, body temperature). Based on the time course of response, a "treatment" design is employed wherever feasible. The direct nerve "block" approach is potentially applicable to a variety of pain disorders including chronic headache, trigeminal neuralgia, and other craniofacial pain disorders. If desired, the route is altered based on the specific model and potential clinical application. For example, the IA route is particularly relevant to a TMJD. Because this technique is challenging in mice, the knee OA model may be employed as a surrogate because this is both feasible and a chronic prevalent clinical condition. Advanced OA, like TMJD may cause pain at rest (i.e., spontaneous or neuropathic pain) that is generally resistant to non-steroidal anti-inflammatory drugs (NSAIDs), and therefore characterized by both neuropathic and nociceptive pain. The well-established monosodium iodoacetate (MIA) intra-articular injection model of OA that elicits weight-bearing asymmetry due to joint osteolysis, cartilage erosion, and referred tactile and thermal hypersensitivity in mice is useful in this regard. This model was previously shown to produce spontaneous pain unrelieved with diclofenac, TRPV1 and TRPA1 antagonists, but entirely relieved with intra-articular lidocaine. IA injection of expression vector mediating Nav1.8 specific LALA (Nav being the target of lidocaine and other short-acting local anesthetics) will be efficacious in this model.

Promoters: Promoter sequences useful in the context of the studies described herein include, but are not limited to: TrkB, TrkC, Nav1.9, other Nav gene promoters, NMDA promoter, advillin, CGRP, 5HT, NK1, ASIC3, NPY or NF200 to drive expression of CA expressing sequences including CA8, CA8 fragment (such as CA8-204), CA10, CA11 and the non-human orthologs including Car8, Car10 and Car11.

Results

Figure 1B:
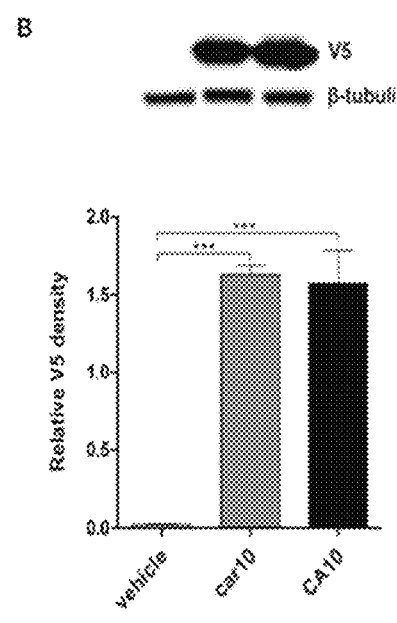
Figure 1C:
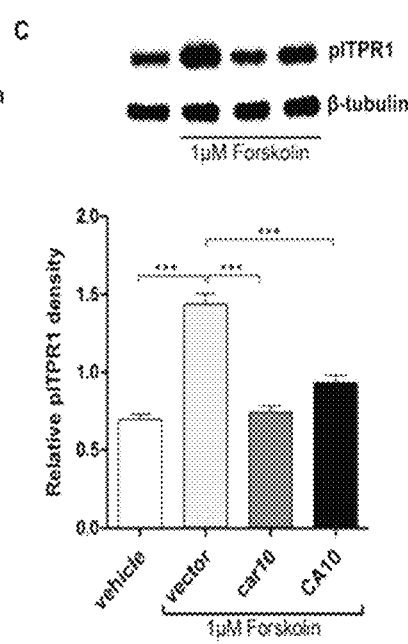

V5-Car10 and V5-CA10 protein overexpression inhibits forskolin-induced pITPR1 in vitro: Results described herein demonstrate, e.g., use of pharmacodynamics bioassays to examine the effects of Car10 on the regulation of ITPR1 activation by phosphorylation (pITPR1) that enhances the response of ITPR1 to the IP3 ligand. HEK293 cells were transfected using AAV8-V5 vectors overexpressing Car10 and CA10, an empty vector and vehicle served as controls. A V5 sequence was inserted at the Car10 or CA10 C-terminal region in order to differentiate between exogenous and endogenous CA10/Car10 expression. Western blot analysis demonstrated that forskolin increases pITPR1 levels in a dose-dependent manner (FIG. 1A). Using the V5 tag, protein overexpression was detected following V5-Car10 and V5-CA10 vector transfection (FIG. 1B). Car10 and CA10 overexpression reduced forskolin-induced ITPR1 phosphorylation in HEK293 cells, whereas empty vector did not alter ITPR1 phosphorylation (FIG. 1C).

Using IHC, increased pITPR1 was observed in HEK293 cells in response to 1 µM forskolin after transfection with empty vector (AAV-null), but after transfection with V5-Car10 and V5-CA10, there was no increase in pITPR1. These data demonstrate that Car10 and CA10 are sufficient to inhibit modulatory domain phosphorylation at Ser-1755 in HEK293 cells, critical to ITPR1 activation and IP3-induced calcium release.

Overexpression of V5-Car10 and V5-CA10 inhibits ATP-induced free calcium release in vitro: ITPR1 contains functionally distinct domains, including the 'modulatory' domain responding to intracellular modulators such as calcium, calmodulin, ATP, and carbonic anhydrase-8 (Car8). ATP increases ITPR1-dependent calcium release by increasing the open probability of the channel in the presence of activating concentrations of IP3 and calcium. It is believed that Car8-mediated inhibition of ITPR1 activation and ATP-mediated calcium release requires binding to this modulatory domain. Therefore, the ability of CA8 fragments (e.g., CA8-204), Car10 and CA10 to bind to ITPR1 and pITPR1 was examined. Co-immunoprecipitation of each protein with antibodies to V5 tag with ITPR1 and pITPR1 before and after forskolin stimulation of HEK293 cells was conducted. Western blotting shows that CA8-204, Car10 and CA10 do not bind to ITPR1. Surprisingly, in the functional bioassay evaluating ITPR1 activation (e.g., pITPR1), co-immunoprecipitation of these proteins shows all of these nonbinding proteins inhibit ITPR1 activation, showing a reduction in pITPR1.

Figure 2:
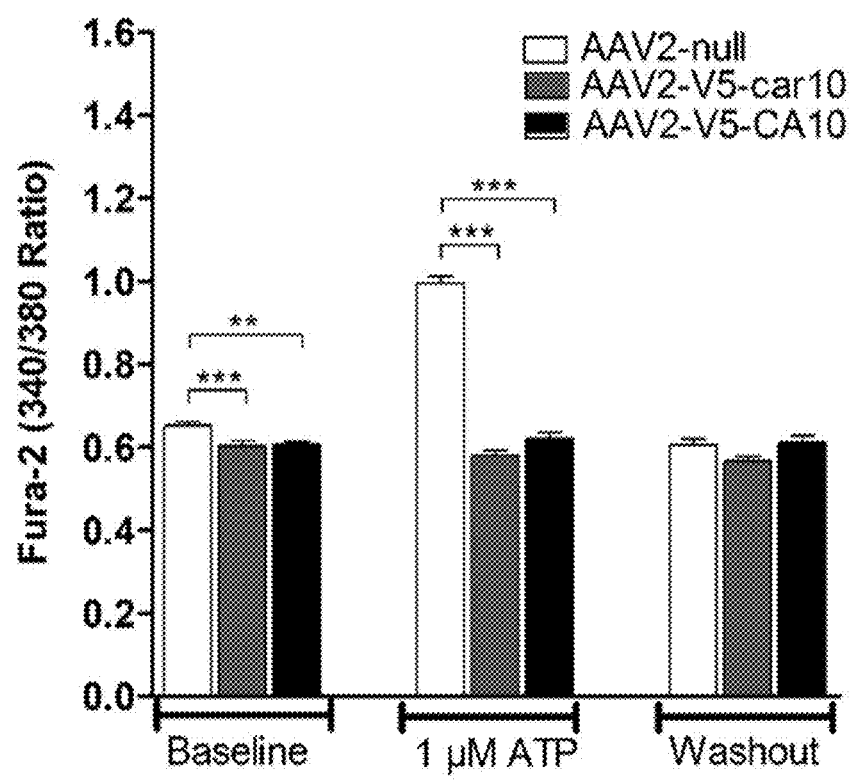
FIG. 2 is a bar graph illustrating that overexpression of AAV-V5-Car10 and AAV-V5-CA10 in HEK293 cells inhibited 1 µM ATP-induced cytoplasmic calcium release (as indicated by Fura-2 (340/380 ratio) (y-axis). Calcium imaging data demonstrated that car10 and CA10 protein overexpression inhibited 1 µM ATP-induced cytoplasmic calcium release in HEK293 cells when compared to empty vector control. Car10 and CA10 overexpression significantly inhibited free calcium release ($P<0.001$). N=4 coverslips and a total of 200 cells per sample  $P<0.01$, * $P<0.001$, by two way ANOVA followed by Bonferroni test.

To further examine whether FLAG-CA8-204 (data not shown), V5-Car10 and V5-CA10 overexpression can inhibit ATP-induced calcium release, HEK293 cells were infected with each if these constructs and real-time intracellular calcium concentrations at baseline and in response to ATP stimulation were measured (FIG. 2). ATP stimulated calcium release and an increase in cytosolic free calcium levels in a dose-dependent manner. Cytoplasmic free calcium levels after AAV-null transfection were increased in response to 1 µM ATP compared to baseline in HEK293 cells. In contrast, free calcium concentrations were unchanged in response to 1 µM ATP after transfection with AAV-FLAG-CA8-204, AAV-V5-Car10 and AAV-V5-CA10 and compared to baseline and AAV-V5-CA8. These data demonstrate that CA8-204, Car10 and CA10 can inhibit ITPR1 activation and thereby reduce ATP-stimulated cytoplasmic free calcium levels in these cells.

Figure 3:
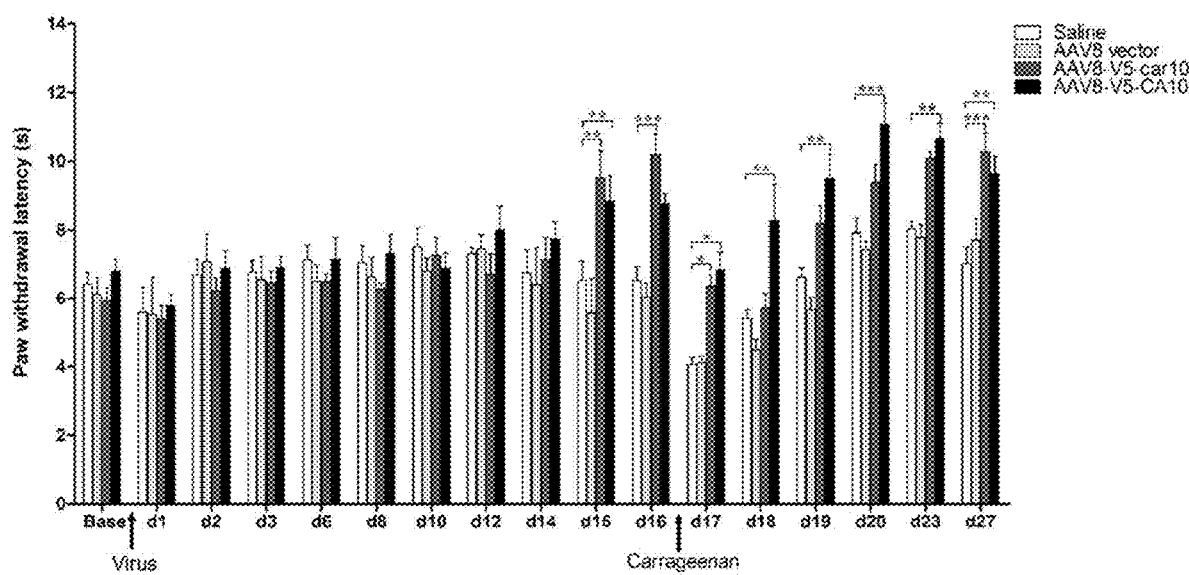
FIG. 3 is a bar graph illustrating paw withdrawal latency (seconds) (y-axis) on various days of study (x-axis), demonstrating that gene transfer of V5-Car10 and V5-CA10 results in thermal anti-hyperalgesia in a carrageenan inflammatory pain mouse model. Thermal responses following overexpression of V5-Car10 and V5-CA10 via sciatic nerve injections of saline, AAV8-null, AAV8-V5-Car10 and AAV8-V5-CA10 viral particles ($1.06E^{14}$ viral particles and $1.66E^{14}$ viral particles, respectively) in C57BL/6J mice. Basal thermal latencies increased by day 15 after injection of AAV8-V5-Car10 and AAV8-V5-CA10 viral particles but not after saline or viral particles containing empty vector. Following carrageenan injections at the end of day 16, the saline and AAV8-null containing viral particles showed a significant reduction from baseline thermal latencies. However, AAV8-V5-Car10 and AAV8-V5-CA10 injected groups did not differ from baseline (N=8. * $P<0.05$,  $P<0.01$, * $P<0.001$, by two way ANOVA followed by Bonferroni Post-hoc test).

Car10 and CA10 sciatic nerve gene therapy produces analgesia and inhibits inflammatory pain behaviors: Both AAV8-V5-Car10 and AAV8-V5-CA10 produce analgesia (increase in thermal latencies from baseline) after sciatic nerve injections in C57BL/6 mice as compared to controls by Day 15 after injections. Intraplantar injections of carrageenan on Day 16 (after thermal testing) produced acute thermal hypersensitivity in saline and AAV8-null control groups on Days 17 and 18. However, both AAV8-V5-Car10 and AAV8-V5-CA10 showed no hypersensitivity (thermal latencies below baseline) after carrageenan injections on Day 16. Analgesia recurred in both AAV8-V5-Car10 and AAV8-V5-CA10 groups after Day 18, and was maintained through Day 27. No similar finding was observed in the control groups. See FIG. 3.

Figure 4:
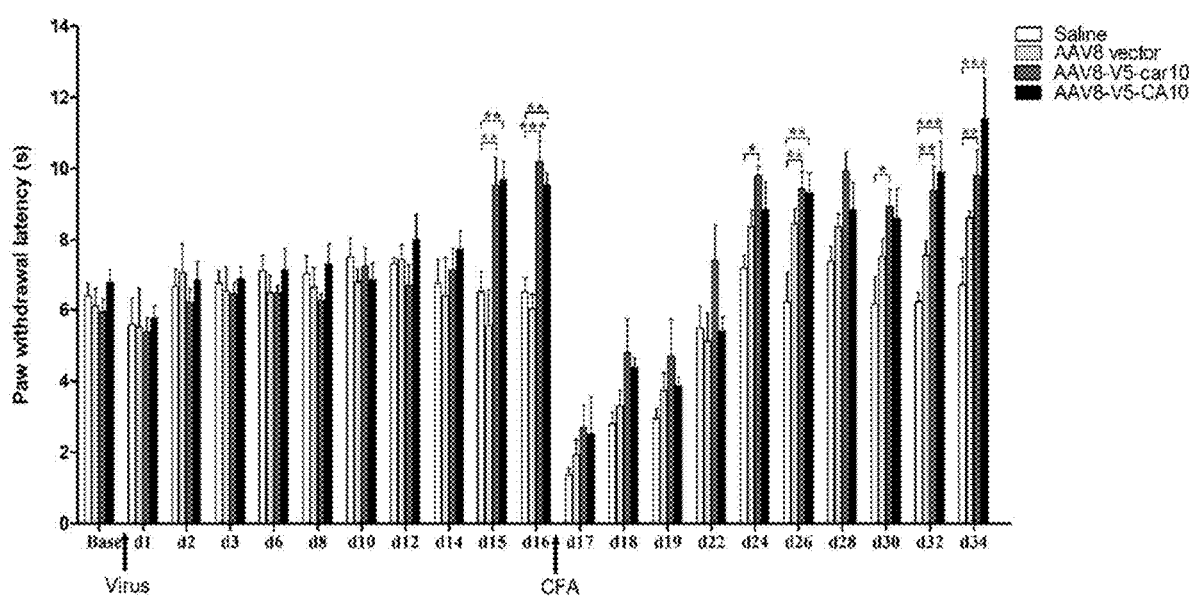
FIG. 4 is a bar graph illustrating paw withdrawal latency (seconds) (y-axis) on various days of study (x-axis), demonstrating that gene transfer of V5-Car10 and V5-CA10 results in thermal anti-hyperalgesia in a Complete Freund's adjuvant (CFA) chronic inflammatory pain mouse model. Thermal responses are shown following sciatic nerve injections of saline, AAV8-null, AAV8-V5-Car10 and AAV8-V5-CA10 viral particles ($1.06E^{14}$ viral particles and $1.66E^{14}$ viral particles, respectively). Basal thermal latencies increased by day 15 after injection of AAV8-V5-Car10 and AAV8-V5-CA10 viral particles, but not after saline or viral particles containing empty vector. Following CFA injections at the end of day 16 (after thermal latencies were measured), all groups had a significant reduction from baseline. Starting from Day 24 the AAV8-V5-Car10 and AAV8-V5-CA10 injected groups showed analgesia (thermal latencies above baseline, similar to Days 15 and 16 after viral injections), while the control groups were unchanged from prior to CFA injection. (N=8. * $P<0.05$,  $P<0.01$, * $P<0.001$, by two way ANOVA followed by Bonferroni Post-hoc test).

Similarly, both AAV8-V5-Car10 and AAV8-V5-CA10 produce analgesia (increase in thermal latencies from baseline) after sciatic nerve injections in C57BL/6 mice as compared to controls by Day 15 after viral injections in a Complete Freund's adjuvant (CFA) chronic inflammatory pain mouse model. Intraplantar injections of CFA on Day 16 (after thermal testing) produced acute thermal hypersensitivity in all groups on Days 17-19. Both the AAV8-V5-Car10 and AAV8-V5-CA10 groups appeared to recover by Day 24, demonstrating analgesia through Day 34, similar to that observed on Day 16 before CFA injections. See FIG. 4.

Figure 5:
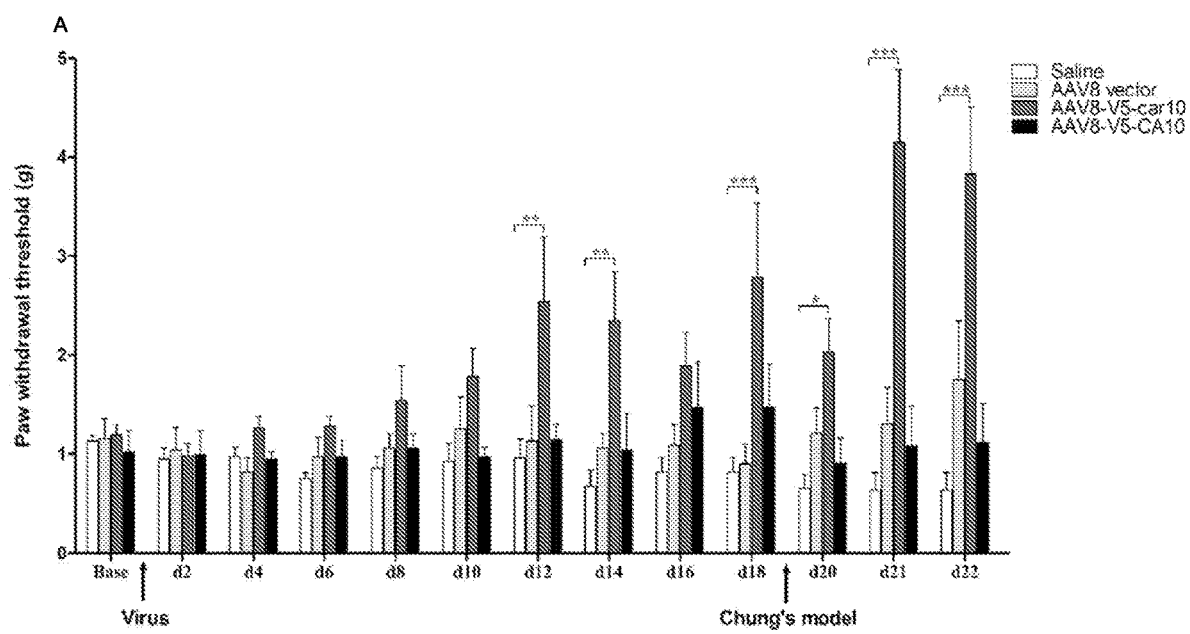
FIG. 5 is a bar graph illustrating paw withdrawal latency (seconds) (y-axis) on various days of study (x-axis), demonstrating that gene transfer of V5-Car10 and V5-CA10 prevents mechanical hyperalgesia in a neuropathic (Chung) mouse pain model. Mechanical withdrawal thresholds are shown following sciatic nerve injections of saline, AAV8-null, AAV8-V5-Car10 and AAV8-V5-CA10 viral particles ($1.06E^{14}$ viral particles and $1.66E^{14}$ viral particles, respectively) in C57BL/6J mice. AAV8-V5-Car10 increased mechanical withdrawal thresholds above baseline (analgesia) on Day 12 after viral injections, and this was maintained through Day 22 despite spinal nerve ligation on Day 19. There was no similar increase in withdrawal thresholds in the other groups. (N=8. * $p<0.05$,  $p<0.01$, * $p<0.001$, by two way ANOVA followed by Bonferroni test).
Figure 6:
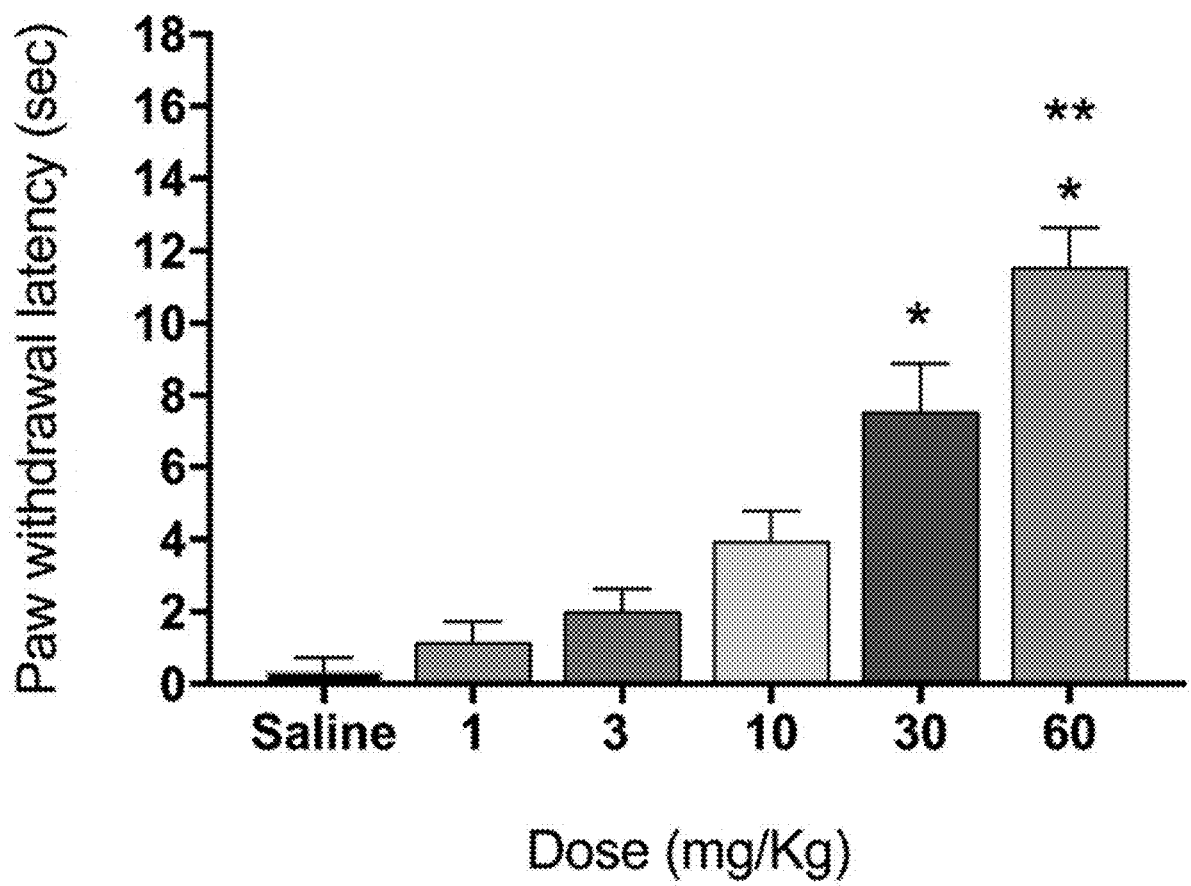
FIG. 6 is a bar graph illustrating the relationship between paw withdrawal latency (seconds) (y-axis) at approximately 30 minutes after the morphine dose was given (intraperitoneal dosing)(x-axis). Elevations were significant when compared with saline at 10, 30, and 60 mg/kg doses.

Car10 gene therapy produces analgesia and inhibits neuropathic pain behaviors: The effect of administration of the viral vector of the disclosure in the prevention of neuropathic pain was examined using the Chung mouse model. Chaplan et al., J Neurosci Methods. 1994; 53(1):55-63. AAV8-V5-Car10 produced analgesic responses in mechanical withdrawal thresholds on Day 12 through Day 22, despite spinal nerve ligation on Day 19. There was no similar increase in withdrawal thresholds in any other group (FIG. 5).

Discussion

The data described herein demonstrate for the first time that (1) overexpression of a CA8 fragment (CA8-204), CA10, and Car10 proteins in vitro inhibits modulatory domain phosphorylation of ITPR1 at Ser-1755 in response to forskolin; (2) overexpression of a CA8 fragment (CA8-204), CA10, and Car10 inhibits ATP-stimulated intracellular calcium release in vitro; (3) and gene transfer of AAV8-V5-CA10 and AAV8-V5-Car10 to nociceptors via sciatic nerve injections into C57BL/6J mice produces profound analgesia and prevents anti-hyperalgesia using inflammatory and neuropathic pain models. These findings establish for the first time that a CA8 fragment (CA8-204), CA10, and Car10 regulate the ITPR1-cytosolic free calcium-signaling pathway, critical to nociception and pain.

CA10 may participate in other functions including regulation of chondrocytes. Loss of CA10 expression could potentially lead to chondroblastoma formation through dysregulation of the ITPR1-cytosolic free calcium-signaling pathway. Therefore, treatment of chondroblastoma may be derived by overexpression of CA10, CA8, or CA8 fragments using viral vectors.

Osteoarthritis (OA) is characterized by cartilage degradation. Akkiraju et al., J Dev Biol. 2015; 3(4):177-192. Interestingly, recent genome-wide association between copy number variants (CNV) with OA susceptibility in a Korean population also demonstrated strong association between OA and CA10. Moon et al., BMC Musculoskelet Disord. 2015; 16:76. Furthermore, Mori et al., described genetic association between single nucleotide polymorphisms in CA8 and CA10 with spine and femoral bone mineral density (BMD) associated with osteoporosis in Japanese women. Mori et al., J Bone Miner Metab. 2009; 27(2):213-216. These investigators suggested that genetic variants at the CA8 and CA10 loci might be important determinants of osteoporosis in these and potentially other women. If these relationships hold true in the broader population, it would be reasonable to test whether functional variants at the CA8 and CA10 loci are associated with OA disease severity, pain and disability. Moreover, it seems relevant to test the role of the ITPR1-cytosolic free calcium-signaling pathway and whether functional variants in CA8, CA10, and CA11 may impact ITPR1 mediated calcium release differently in osteoclast and chondrocyte regulation and thereby influence osteoporosis and osteoarthritis differently.

Finally, mental health disorders are frequently comorbid with chronic pain. Trinucleotide repeat expansion is associated with the heritability of fragile-X syndrome, Huntington's disease, myotonic dystrophy and spinocerebellar ataxia. Akkiraju et al., J Dev Biol. 2015; 3(4):177-192. Additionally, unstable repeats have also been implicated in schizophrenia and bipolar disorder. Vincent et al., Psychiatr Genet. 2016; 26(4):156-165. Subsequent studies show that much of the signal in psychiatric disease originates from three regions harboring large repeats on chromosome 13q21.33, 17q21.33-q22, and 18q21.2. The 17q trinucleotide expansion is located within an intron of the CA10 gene. Vincent et al., supra; Ikeuchi et al., Genomics. 1998; 49(2):321-326. Given the new potential roles for CA10 described herein, it is worthwhile to revisit the relationship between loss of function due to CA10 functional variants, including this unstable trinucleotide repeat and osteoarthritis, osteoporosis, chronic pain conditions and the use of CA10 overexpression in these affected individuals using compositions and methods described herein to treat these disorders.

In summary, this Example demonstrates the utility of PK/PD bioassays and animal models and routes of administration of viral vectors encoding CA8, CA8 fragment (CA8-204) fragment, and CA10 to treat pain. In particular, these data establish that the materials and methods described herein produce analgesia and inhibit both inflammatory and neuropathic pain.

Example 2

The following Example demonstrates that administration of an adeno-associated viral vector encoding CA8 fragments described herein (AAV8-FLAG-CA8$^{204}$C (CA8$^{204C}$) and the AAV8-FLAG-CA8$^{204G}$ (CA8$^{204G}$) produces analgesia anti-hyperalgesia in a clinically relevant animal model, the carrageenan inflammatory pain model.

Construction of pAAV-flag-CA8-204$^G$ (ALT G) and pAAV-flag-CA8-204$^C$ (ALT C). SalI and KpnI sites containing primers were designed for constructing full length alternatively spliced variant (CA8-204) with "G" or "C" at SNP rs6471859. The pAAV-MCS expression construct is shown to the right (vector map on right). See FIG. 39.

Figure 31:
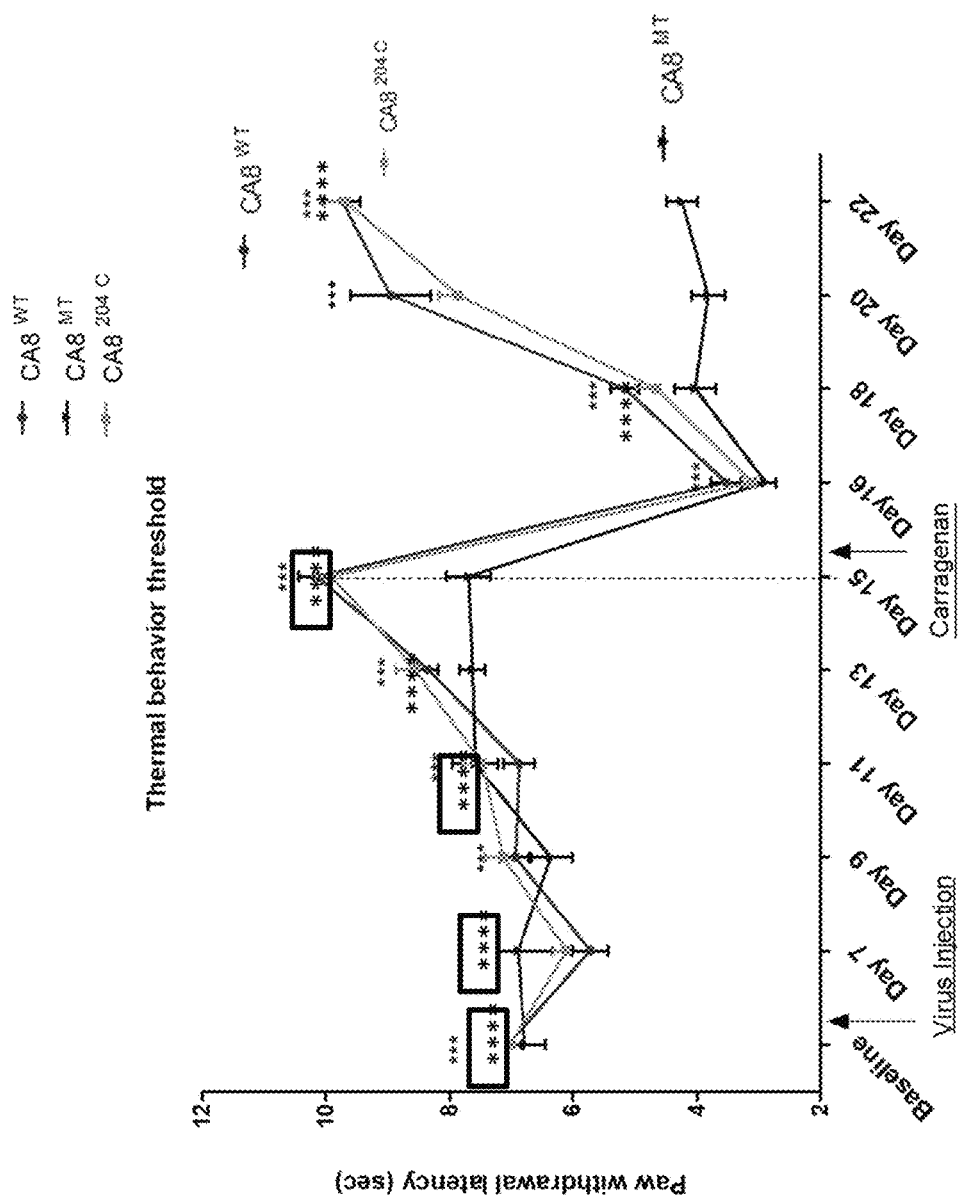
FIG. 31 is a graph showing the gene transfer of CA fragment $CA8^{204C}$ in an inflammatory pain animal model produced analgesia anti-hyperplasia.
Figure 32:
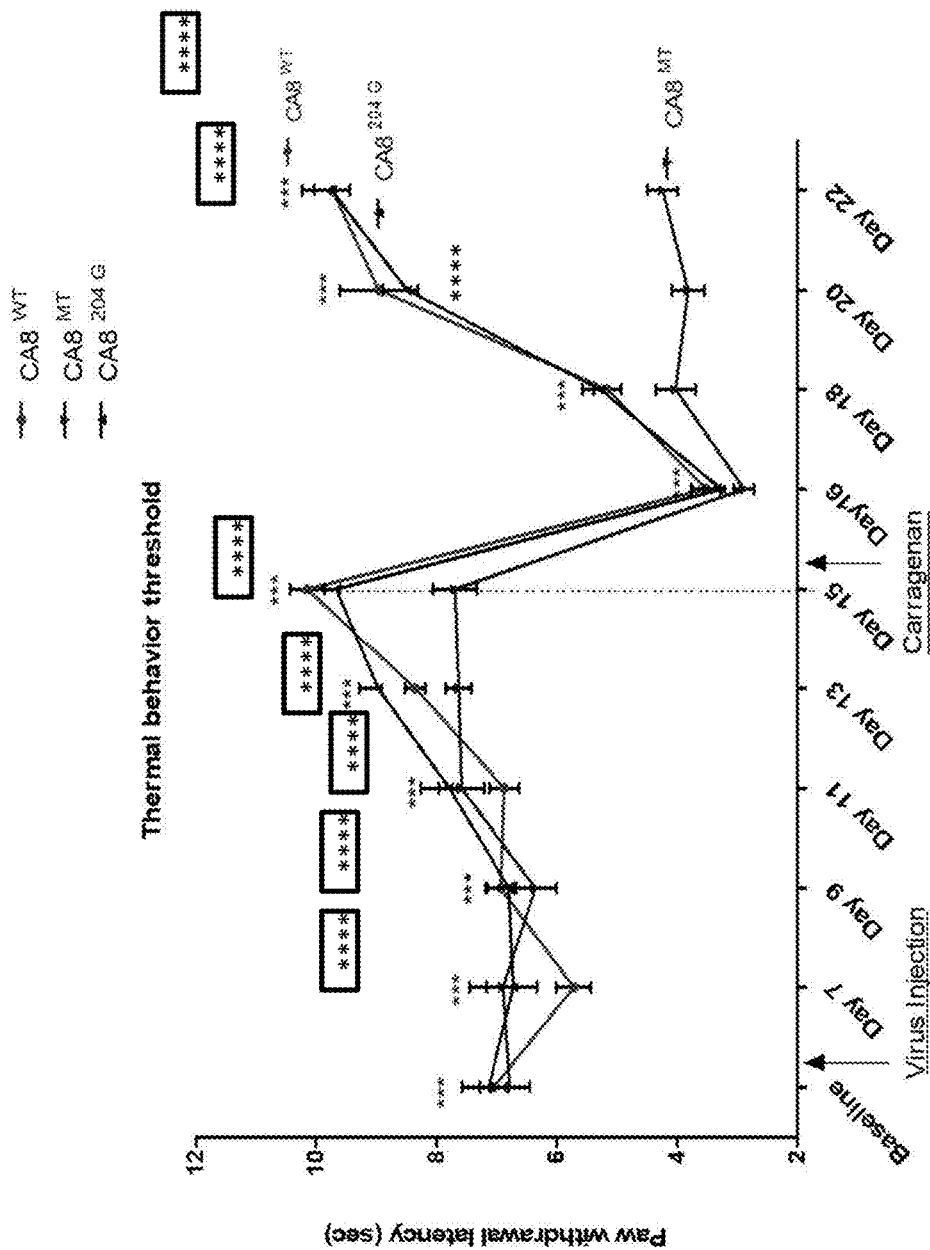
FIG. 32 is a graph showing the gene transfer of CA fragment $CA8^{204G}$ in an inflammatory pain animal model produced analgesia anti-hyperplasia.

Paw withdrawal thermal latencies were measured at the baseline, and various days following viral vector administration (sciatic nerve injection (SN)) and/or carrageenan injection (left paw). Seven days following administration, mice (n=8 mice per group) that received SN injections of AAV8-FLAG-CA8$^{204C}$ (CA8$^{204C}$) or AAV8-FLAG-CA8$^{204G}$ (CA8$^{204G}$) (1.5 µl, 1×10$^{13}$ genome copies/ml) had increasing paw withdrawal latencies, compared to mice administered AAV8-V5-CA8 WT (CA8 WT; positive control) and AAV8-V5-CA8 MT (CA8 mutant; negative control). At day 15 post-viral vector administration, after receiving carrageenan injections, mice in the CA8 MT (negative control) group showed markedly reduced paw withdrawal on days 16 to 18, indicating failure to recuperate from inflammatory pain induced by carrageenan. The mice in both CA8 WT, CA8$^{204G}$ and CA8$^{204C}$ groups, however, demonstrated enhanced paw withdrawal latency, indicating the anti-hyperalgesia protection provided by the CA8 WT, CA8$^{204G}$ and CA8$^{204C}$ (N=8, ** P<0.0001*P<0.001, two way Anova statistical group test GraphPad). See FIGS. 31 and 32.

Example 3

This Example demonstrates that CA10 binds to RYR and pRYR, as demonstrated by co-immunoprecipitation. NBL cells were transfected with AAV-V5-CA10 and AAV-V5-Car10 using Lipofectamin (LTX). Cellular protein was extracted 48 h after transfection.

Immunoprecipitation (IP) and western blotting (WB) was utilized to detect binding. Rabbit anti-RYR1 was used for IP and chicken anti-V5 was used for WB analyses. About ⅒ of the IP protein was used for WB to show the V5 labeled CA10 or Car10 by WB. B-actin was used as a loading control. See FIG. 33, which establishes co-immunoprecipitation of CA10 and RYR. Similar results were obtained with CA10 and ITPR1.

These data suggest for the first time that CA10 may also possibly regulate RYR-dependent calcium release through binding to RYR1 and RYR3.

Example 4

This Example demonstrates that V5-CA10 protein overexpression inhibits forskolin-induced pITPR1 in vitro.

In order to examine the role of CA10 in the regulation of ITPR1 phosphorylation (pITPR1) that enhances the response of ITPR1 to the IP3 ligand, HEK293 cells were transfected with AAV8-V5-CA10 vectors. Transfection with empty vectors or application of vehicle served as controls. A V5 sequence was inserted at the C-terminal region of CA10 in order to differentiate between exogenous and endogenous expression of the native protein in tissues or cell lines. Cells were stained for nuclei with DAPI or pITPR1 and merged.

Using the V5 tag, protein overexpression was observed following AAV-V5-CA10 (and murine V5-Car10-encoding vectors) transfections using Western blot analyses (FIG. 34A). CA10 and Car10 overexpression reduced forskolin-induced ITPR1 phosphorylation in HEK293 cells, whereas empty vector did not alter pITPR1 levels (FIG. 34B). These experiments indicate that overexpression of CA10 (and murine Car10) in NBL cells in vitro inhibits modulatory domain phosphorylation of ITPR1 at Ser-1755 in response to forskolin.

Example 5

The following Example demonstrates that CA10 overexpression inhibits ITPR1- and RYR-mediated calcium release in response to pain mediators. Surprisingly, the studies described herein demonstrate that, in NBL cells, 5HT-mediated RYR-dependent calcium release in nearly completely inhibited by ryanodine. Moreover, V5-CA10 overexpression in NBL cells was observed to also inhibit 5HT-mediated calcium release. Therefore, 5HT-mediated signaling in NBL cells appears to be largely through RYR.

Next, it was determined that overexpression of V5-Car10 and V5-CA10 in HEK293 cells inhibits ATP-induced cytoplasmic calcium release. Fura2 calcium imaging data demonstrated that Car10 and CA10 protein overexpression inhibits ITPR1-mediated cytoplasmic calcium release to 1 µM ATP in HEK293 cells when compared to empty vector control (P<0.001). (N=4 coverslips and a total of 200 cells per sample P<0.01, *P<0.001, by two way ANOVA followed by Bonferroni test.) See FIG. 35.

It was also determined that 5HT-induced RYR-dependent calcium release in NBL cells is inhibited by ryanodine. Fura2 calcium imaging data demonstrated that 50 µM 5HT-induced cytoplasmic calcium release in NBL cells was significantly inhibited by ryanodine in a dose-dependent manner, when compared to vehicle control (P<0.001). (N=4 coverslips and a total of 200 cells per sample P<0.01, *P<0.001, by two way ANOVA followed by Bonferroni test). See FIG. 36.

These findings suggest that CA10 regulates the ITPR1-cytosolic free calcium-signaling pathway, critical to nociception and pain behaviors. Additionally, the data showed that 5HT stimulates calcium release that is nearly completely inhibited by ryanodine, suggesting serotonin through RYR and not ITPR1.

Figure 37:
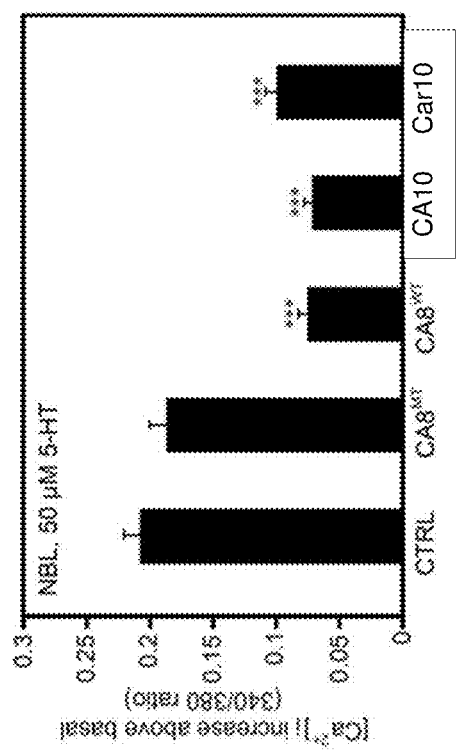
FIG. 37 is a bar graph showing that overexpression of V5-Car10 and V5-CA10 in NBL cells inhibits 50 µM 5HT-induced cytoplasmic calcium release.

Next, it was determined that overexpression of V5-Car10 and V5-CA10 in NBL cells inhibits 50 μM 5HT-induced cytoplasmic calcium release. See FIG. 37. Fura2 calcium imaging data demonstrated that 50 μM 5HT-induced cytoplasmic calcium release in NBL cells was nearly completely inhibited by 10 nM ryanodine when compared to vehicle control (P<0.001). Additionally, 5HT-induced cytoplasmic calcium release in NBL cells was also inhibited by V5-Car10 and V5-CA10 protein overexpression in NBL cells when compared to empty vector control (P<0.001). (N=4 coverslips and a total of 200 cells per sample P<0.01, *P<0.001, by two way ANOVA followed by Bonferroni test).

Example 6

Construction of pCMV-N-flag-CA8-204$^G$ and pCMV N-flag-CA8-204$^C$. SalI and KpnI sites containing primers were designed for constructing full length alternative variant (CA8-204) with "G" at rs6471859 SNP, into pCMV-N-flag vector (Clontech). Site directed mutagenesis (Invitrogen) was utilized to construct pCMV-N-flag-CA8-204$^C$ producing a novel fragment ending at exon 3 with "C" allele at rs647859. See FIG. 38.

Figure 40:
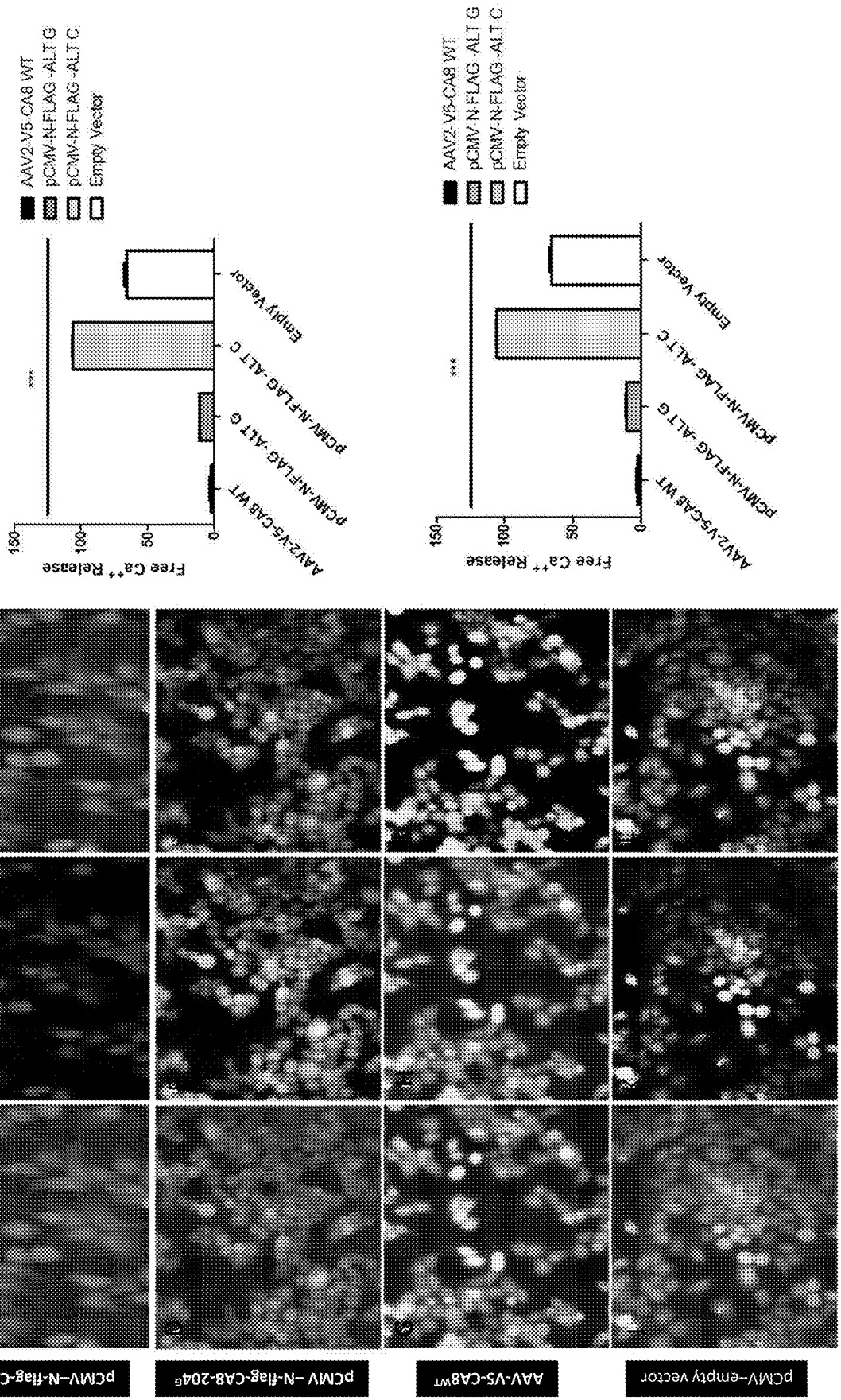
FIG. 40 shows that CA8-204$^G$ inhibition of calcium release ($Ca^{2+}$ Fura2 imaging) in NBL cells.

CA8-204$^G$ inhibition of calcium release (Ca$^{2+}$ Fura2 imaging) in HEK293 cells. HEK293 cells transfected with pCMV-N-flag-CA8-204$^G$ (1,695 bp), pCMV-N-flag-CA8-204$^C$, AAV2-V5-CA8$^{WT}$ (positive control), or empty vector (negative control)·(n=6,number of coverslips in each experiment, number of experiments=3, P-value <0.001, comparison between three groups was carried out by Tukey's multiple comparison test (GraphPad Prism Software). See FIG. 40.

Figure 41:
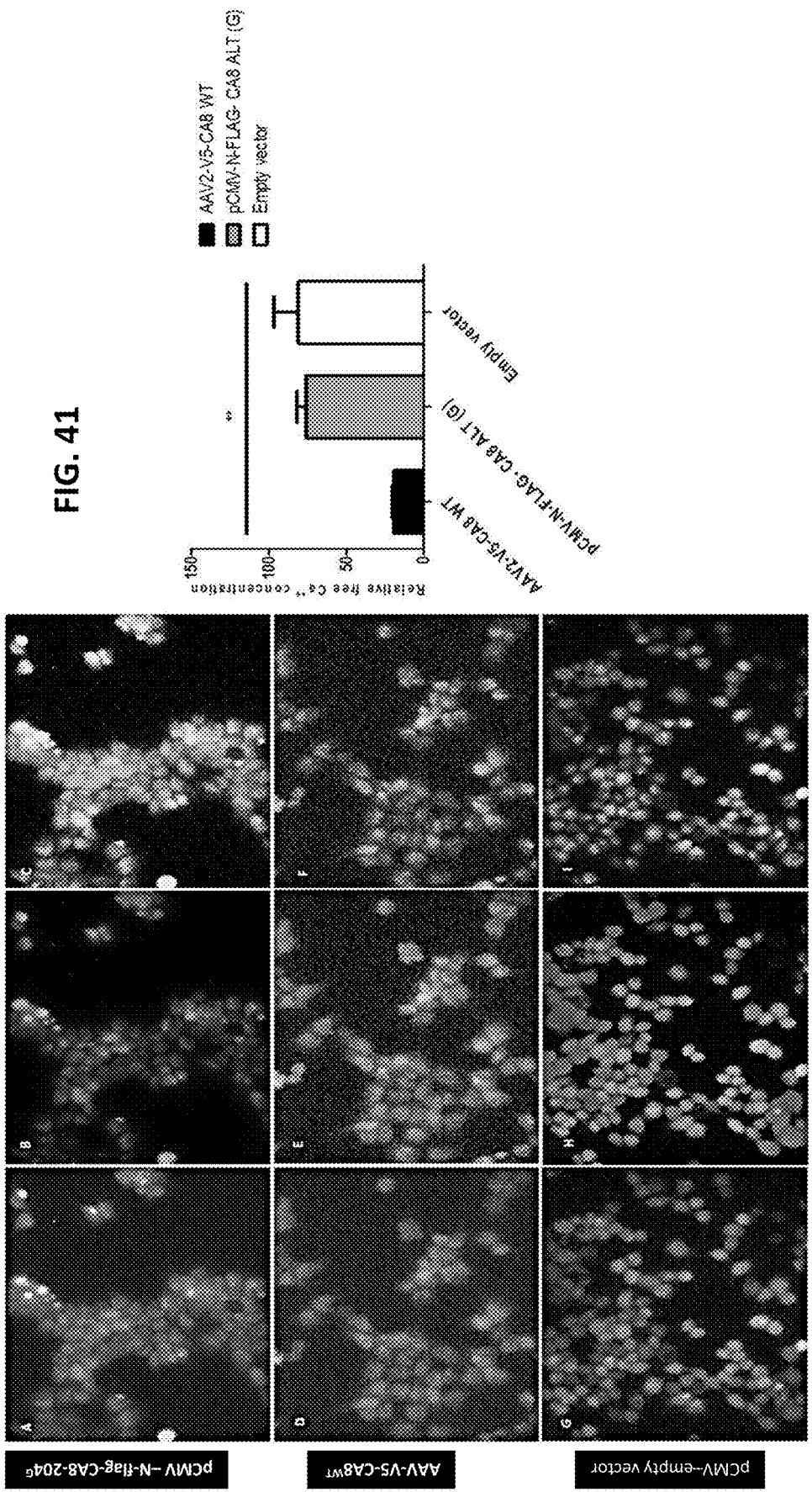
FIG. 41 shows that differential tissue expression of CA8 ALT(G) (CA8-204$^G$) and CA8 ALT(C) (CA8-204$^C$) in HEK293 (FIG. 41A) and NBL (FIG. 41B) cells.

Differential tissue expression of CA8 ALT (G) and CA8 ALT (C) in HEK293 and NBL cells. Quantitative RT-PCR (Real Time PCR, Applied Biosystems) from (a) HEK293 cells and (b) Neuronal cells (NBL) after transfections with alternative variant pCMV-FLAG-N CA8 ALTG with "G" allele at rs6471859 (bp 1417 of CA8-204) or pCMV-FLAG-N CA8 ALTC ("C" allele at rs 6471859). Quantities of respective vectors were normalized using beta Actin (ACTB) gene product. The primers used were designed covering the 3'UTR ewgion of CA8-204. The HK cells do not express detectable CA8-002 transcript with the C genotype at variant rs6471859. N=3, number of experiments=3 (Statistical analysis was done using GraphPad Prism Software, =p-Value <0.001, *=p-Value <0.0001, One Way Anova was applied followed by Tukey group comparison. See FIGS. 41A and 41B.

Figure 42A:
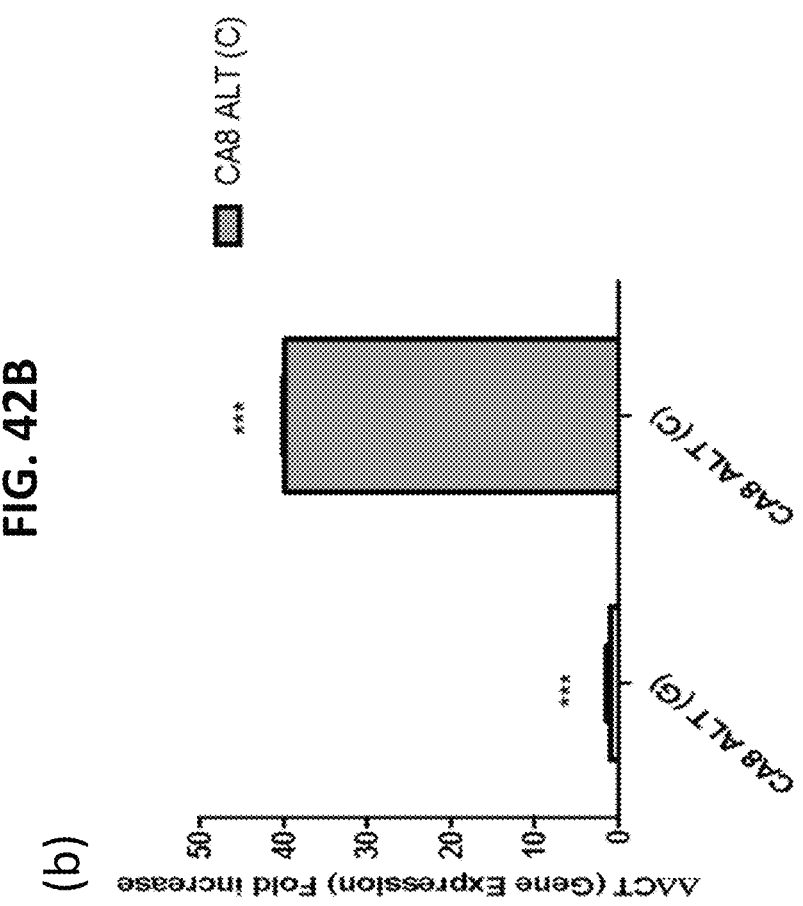
FIG. 42 is a graph showing that CA8-204$^C$ and CA8-204$^G$ fragments have variable tissue expression.
Figure 42B:
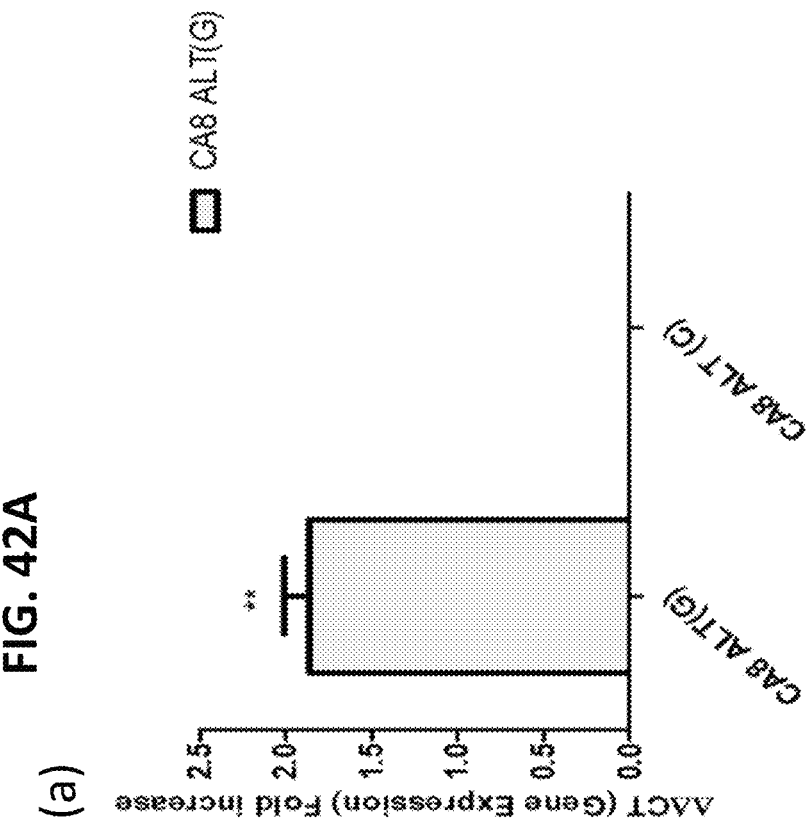

CA8-204$^C$ and CA8-204$^G$ fragments show variable tissue expression. HEK 293 (non-neuronal cells) and NBL (neuronal cells) were transfected with vectors expressing CA8-204$^C$ and CA8-204$^G$ transcripts and subjected to quantitative RT-PCR (QPCR—Applied Biosystems) using SyBr green (AB), normalized using beta-actin as an internal control. The primers were designed to flank the 3'UTR region of the CA8-204$^C$ and CA8-204$^G$ sequences expressed selectively in these cell lines. We observe a marked difference of CA8 fragment splicing and expression where the CA8-204$^C$ is expressed predominantly in NBL cells and the CA8-204$^G$ is expressed predominantly in the HEK293 cells consistent with cell specific splicing factors dictating expression of each fragment. (N=4, ***P-Value <0.001, one way ANOVA was applied followed by post-hoc Tukey's test). See FIG. 42.

Figure 43:
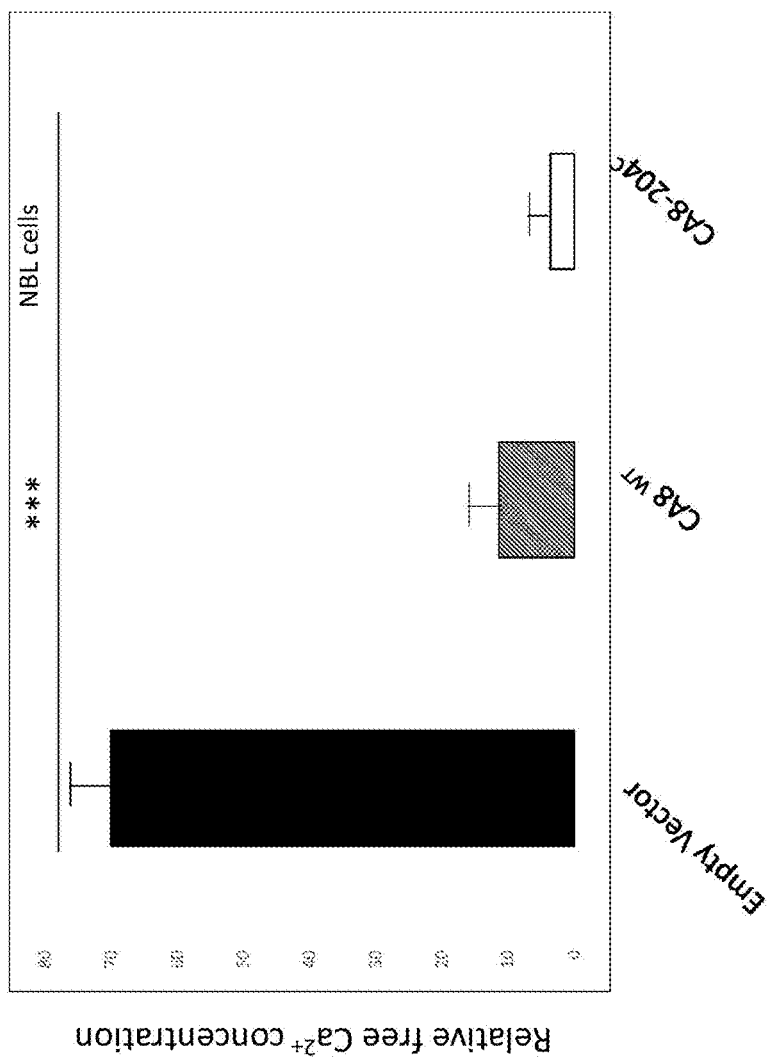
FIG. 43 shows that CA8-204$^C$ fragment inhibits ATP stimulated calcium release in NBL cells.

CA8-204$^C$ fragment inhibits ATP stimulated calcium release in NBL cells. NBL cells were transfected with vectors with nucleotide inserts expressing CA8-204$^C$, CA8-201 (CA8 wildtype positive control) or empty vector (negative control) and were subjected to calcium imaging (Fura2, Leica Micro Systems), using 1 μM ATP as a stimulant for intracellular calcium release. CA8-204$^C$ and CA8-201 were able to inhibit Ca$^{2+}$ release in NBL cells in vitro. Inhibition of calcium release by CA8-204$^C$ exceeded that of CA8-201 (wildtype full length transcript/peptide). In contrast, empty vector (negative control) failed to inhibit calcium release in this assay. (N=6, ***P<0.001, statistical analysis led by one way ANOVA, group comparison through Tukey's post-hoc test, GraphPad Prism). See FIG. 43.

Figure 44:
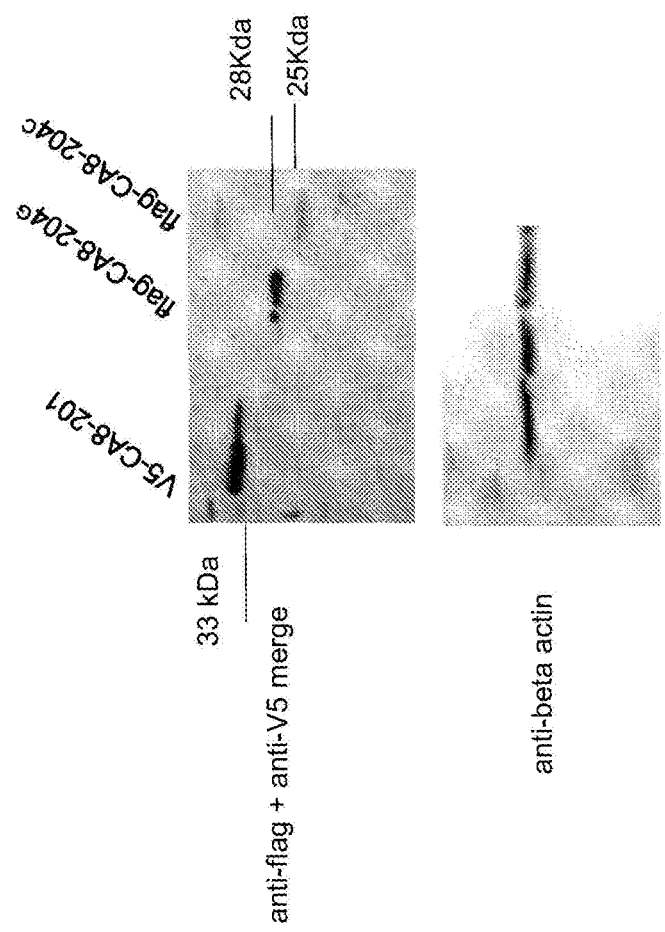
FIG. 44 is a gel showing that CA8-204$^G$ or CA8-204$^C$ peptide fragments are 28 or 26 kDa as expressed selectively in HEK293 or NBL cells.

CA8-204$^G$ or CA8-204$^C$ peptide fragments are 28 or 26 kDa as expressed selectively in HEK293 or NBL cells. Proteins were extracted from HEK293 (middle) or NBL cells (right) transfected with vectors expressing either flag-CA8-204$^G$, flag-CA8-204$^C$, or V5-CA8-201 (wildtype full length CA8) transcripts, run on the same gel and immunoblotted with either anti-flag or anti-V5 antibodies. Only flag-CA8-204$^G$ peptide fragment was detected at 28 kDa in HEK293 cells and only flag-CA8-204$^C$ peptide fragment at 26 kDA was detected in NBL cells. Data was merged after immunoblotting. Data was normalized with beta actin (control). See FIG. 44.

CA8$^{204\ C}$ inhibits forskolin induced phosphorylation of pITPR1. HEK 293 cells were transfected with vectors containing CA8$^{WT}$, CA8$^{204\ C}$ or empty vectors (vehicle). Vehicle was used as a negative control. Data was normalized with vinculin as internal control. See FIG. 45.

All publications, patents and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed:

1. A method of treating or preventing pain in a subject in need thereof, the method comprising administering to the subject an expression vector comprising a nucleic acid sequence encoding a fragment of human carbonic anhydrase 8, wherein the fragment of carbonic anhydrase 8 is CA8-202, CA8-203 or CA8-204.

2. The method of claim 1, wherein the pain is neuropathic pain.

3. The method of claim 1, wherein the pain is inflammatory pain.

4. The method of claim 1, wherein the pain is caused by cancer or spinal cord injury.

5. The method of claim 1, comprising administering the expression vector to the dorsal root ganglion of the subject.

6. The method of claim 1, comprising administering the expression vector via intraarticular injection.

7. The method of claim 1, comprising administering the expression vector orally.

8. The method of claim 1, comprising administering the expression vector to the trigeminal ganglia.

9. The method of claim 1, comprising administering the expression vector via peripheral nerve injection.

10. The method of claim 1, comprising administering the expression vector via catheter to a site where pain arises.

11. The method of claim 1, comprising administering the expression vector via needle to a site where pain arises.

12. The method of claim 1, comprising use of imaging to administer the expression vector.

13. The method of claim 1, wherein the expression vector is a viral vector.

14. The method of claim 1, wherein the nucleic acid sequence encoding a fragment of carbonic anhydrase 8 is operably linked to a promoter selected from the group consisting of CMV promoter, TrkA promoter, TrkB promoter, TrkC promoter, Nav1.9 promoter, Nav1.7 promoter, Nav1.8 promoter, NMDA promoter, advillin promoter, CGRP promoter, 5HT promoter, NK1 promoter, ASIC3 promoter, NPY promoter, and NF200 promoter.

15. The method of claim 1, wherein the fragment of human carbonic anhydrase 8 is CA8-204C or CA8-204G.

16. The method of claim 1, wherein the fragment of human carbonic anhydrase 8 is CA8-202 or CA8-203.

17. The method of claim 1, comprising administering the expression vector via needle to the epidural space.

18. The method of claim 1, comprising administering the expression vector via needle via the transforaminal epidural space.

19. The method of claim 1, comprising administering the expression vector via needle to the ganglia of spinal nerves transmitting pain.

20. A vector comprising a nucleic acid encoding a fragment of human carbonic anhydrase 8, wherein the fragment of carbonic anhydrase 8 is CA8-202, CA8-203 or CA8-204.

21. The vector of claim 20, wherein the nucleic acid encodes an amino acid sequence that is at least 95% identical to SEQ ID NO: 32 (CA8-204C) or SEQ ID NO: 33 (CA8-204G).

22. The vector of claim 20, wherein the nucleic acid encodes the amino acid sequence set forth in SEQ ID NO: 32 (CA8-204C).

23. The vector of claim 20, wherein the nucleic acid encodes the amino acid sequence set forth in SEQ ID NO: 33 (CA8-204G).

* * * * *